United States Patent
Barnes et al.

(10) Patent No.: US 7,700,633 B2
(45) Date of Patent: Apr. 20, 2010

(54) ORGANIC COMPOUNDS

(75) Inventors: David Barnes, Waban, MA (US); Gregory Raymond Bebernitz, Stow, MA (US); Gary Mark Coppola, Budd Lake, NJ (US); Travis Stams, Stow, MA (US); Sidney Wolf Topiol, Fair Lawn, NJ (US); Thalaththani Ralalage Vedananda, Shrewsbury, MA (US); James Richard Wareing, Stow, MA (US); Katsumasa Nakajima, Winchester, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/096,439

(22) PCT Filed: Dec. 6, 2006

(86) PCT No.: PCT/US2006/046545

§ 371 (c)(1),
(2), (4) Date: Jun. 6, 2008

(87) PCT Pub. No.: WO2007/067615

PCT Pub. Date: Jun. 14, 2007

(65) Prior Publication Data

US 2008/0262050 A1 Oct. 23, 2008

Related U.S. Application Data

(60) Provisional application No. 60/748,573, filed on Dec. 8, 2005.

(51) Int. Cl.
*A61K 31/433* (2006.01)
*C07D 285/10* (2006.01)

(52) U.S. Cl. ...................................... 514/362; 548/135

(58) Field of Classification Search ................. 548/135; 514/362

See application file for complete search history.

(56) References Cited

U.S. PATENT DOCUMENTS

| 7,291,635 | B2 | 11/2007 | Coppola et al. |
| 2008/0293776 | A1 | 11/2008 | Barnes et al. |
| 2008/0293782 | A1 | 11/2008 | Barnes et al. |
| 2009/0181928 | A1 | 7/2009 | Neubert et al. |

FOREIGN PATENT DOCUMENTS

| WO | 03082841 A | 10/2003 |
| WO | 04041799 A | 5/2004 |
| WO | 04050646 A | 6/2004 |

OTHER PUBLICATIONS

Black, et al. Bioorganic & Medicinal Chem. Letters, vol. 15, No. 10 (2005), pp. 2503-2507.*
Black, et al. "Structure-based design of protein tyrosine phosphatase-1B inhibitors." Bioorganic and medicinal chemistry letters. vol. 15, No. 10, Apr. 16, 2005, pp. 2503-2507. p. 2504, Scheme 1.
Elchebly, et al. "Increased Insulin Sensitivity and Obesity Resistance in Mice Lacking the Protein Tyrosine Phosphatase-1B Gene." Science, vol. 283, Mar. 5, 1999, pp. 1544-1548.
Johnson, et al. "Protein Tyrosine Phosphatase 1B Inhibitors for Diabetes" Nature, vol. 1, Sep. 2002, pp. 696-709.
Unpublished U.S. Appl. No. 12/096,432, filed Dec. 6, 2006, in the name of Novartis AG.
Unpublished U.S. Appl. No. 12/515,519, filed Nov. 30, 2007, in the name of Novartis AG.

* cited by examiner

*Primary Examiner*—Kamal A Saeed
*Assistant Examiner*—Janet L Coppins
(74) *Attorney, Agent, or Firm*—Theresa Devlin

(57) ABSTRACT

Compounds of the formula (I)

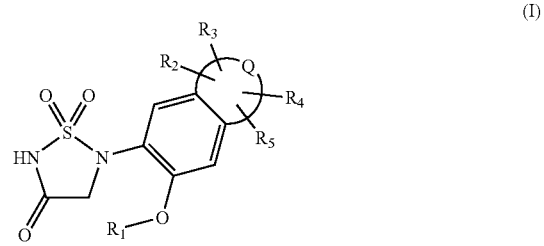

are inhibitors of protein tyrosine phosphatases (PTPases) and, thus, may be employed for the treatment of conditions mediated by PTPase activity. The compounds of the present invention may also be employed as inhibitors of other enzymes characterized with a phosphotyrosine binding region such as the SH2 domain. The compounds of formula (I) may be employed for prevention and/or treatment of insulin resistance associated with obesity, glucose intolerance, diabetes mellitus, hypertension and ischemic diseases of the large and small blood vessels, conditions that accompany type-2 diabetes, including hyperlipidemia, hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat and/or prevent cancer, osteoporosis, neurodegenerative and infectious diseases, and diseases involving inflammation and the immune system.

33 Claims, No Drawings

ORGANIC COMPOUNDS

This application is the National Stage of Application No. PCT/US2006/046545, filed on Dec. 6, 2006, which claims benefit under 35 U.S.C. §119(e) of U.S. Provisional Application No. 60/748,573, filed Dec. 8, 2005, the contents of which are incorporated herein by reference in their entirety.

The present invention relates to thiadiazolidinone derivatives, pharmaceutical compositions containing such compounds, methods of making such and methods of treating conditions mediated by protein tyrosine phosphatases by employing such compounds.

Accordingly, the present invention provides compounds of the formula

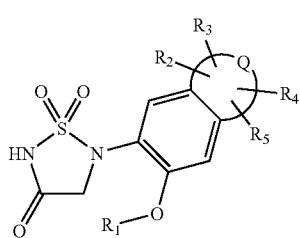

(I)

wherein

Q combined together with the carbon atoms to which it is attached form an aromatic, or a partially or fully saturated nonaromatic 5- to 8-membered carbocyclic or heterocyclic ring;

$R_1$ is hydrogen, —C(O)$R_6$, —C(O)N$R_7R_8$ or —C(O)O$R_9$ in which $R_6$ and $R_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_8$ and $R_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_2$, $R_3$, $R_4$ and $R_5$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or ($C_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_2$ and $R_3$ combined are alkylene which together with the ring atoms to which they are attached form a 3- to 7-membered fused ring; or $R_2$ and $R_3$ combined are alkylene which together with the carbon atom to which they are attached form a 3- to 7-membered spirocyclic ring;

or a pharmaceutically acceptable salt thereof.

The compounds of the present invention are inhibitors of protein tyrosine phosphatases (PTPases), in particular, the compounds of formula (I) inhibit PTPase-1B (PTP-1B) and T-cell PTPase (TC PTP) and, thus, may be employed for the treatment of conditions mediated by PTPase activity. Accordingly, the compounds of formula (I) may be employed for treatment of insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

The present invention also concerns the use of the compounds of formula (I) may be employed for treatment of insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

Listed below are definitions of various terms used to describe the compounds of the instant invention. These definitions apply to the terms as they are used throughout the specification unless they are otherwise limited in specific instances either individually or as part of a larger group. In general, whenever an alkyl group is referred to as a part of the structure, an optionally substituted alkyl is also indended.

Accordingly, the term "optionally substituted alkyl" refers to unsubstituted or substituted straight or branched chain hydrocarbon groups having 1 to 20 carbon atoms, preferably 1 to 8 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halogen, hydroxy, cycloalkyl, cycloalkoxy, acyl, acyloxy, alkoxy, alkyloxyalkoxy, alkanoyloxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaraloxy, heterocyclyl and heterocyclyloxy including indolyl, imidazolyl, furyl, thienyl, thiazolyl, pyrrolidyl, pyridyl, pyrimidyl, piperidyl, morpholinyl and the like.

The term "lower alkyl" refers to any of the above alkyl groups as described above having 1 to 7, preferably 1 to 4 carbon atoms.

The term "halogen" or "halo" refers to fluorine, chlorine, bromine and iodine.

The term "alkenyl" refers to any of the above alkyl groups having at least 2 carbon atoms and containing a carbon to carbon double bond at the point of attachment. Groups having 2 to 8 carbon atoms are preferred.

The term "alkynyl" refers to any of the above alkyl groups having at least two carbon atoms and containing a carbon to carbon triple bond at the point of attachment. Groups having 2 to 8 carbon atoms are preferred.

The term "alkylene" refers to a straight-chain bridge of 1-6 carbon atoms connected by single bonds, e.g., —$(CH_2)_x$—, wherein x is 1-6, which may be interrupted with one or more heteroatoms selected from O, S, S(O), $S(O)_2$ or NR", wherein R" may be hydrogen, alkyl; cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or $(C_{1-8})$alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl, heterocyclyloxy and the like.

The term "cycloalkyl" refers to optionally substituted monocyclic, bicyclic or tricyclic hydrocarbon groups of 3 to 12 carbon atoms, each of which may be substituted by one or more substituents such as alkyl, halo, oxo, hydroxy, alkoxy, alkanoyl, acylamino, carbamoyl, alkylamino, dialkylamino, thiol, alkylthio, nitro, cyano, carboxy, carboxyalkyl, alkoxycarbonyl, sulfonyl, sulfonamido, sulfamoyl, heterocyclyl and the like.

Exemplary monocyclic hydrocarbon groups include but are not limited to cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "alkanoyloxy" refers to alkyl-C(O)—O—.
The terms "alkylamino" and "dialkylamino" refer to alkyl-NH— and $(alkyl)_2N$—, respectively.
The term "alkanoylamino" refers to alkyl-C(O)—NH—.
The term "alkylthio" refers to alkyl-S—.
The term "alkylaminothiocarbonyl" refers to alkyl-NHC(S)—.
The term "trialkylsilyl" refers to $(alkyl)_3Si$—.
The term "trialkylsilyloxy" refers to $(alkyl)_3SiO$—.

The term "alkylthiono" refers to alkyl-S(O)—.
The term "alkylsulfonyl" refers to alkyl-$S(O)_2$—.
The term "alkoxycarbonyl" refers to alkyl-O—C(O)—.
The term "alkoxycarbonyloxy" refers to alkyl-O—C(O)O—.
The term "carboxycarbonyl" refers to HO—C(O)C(O)—.
The term "carbamoyl" refers to $H_2NC(O)$—, alkyl-NHC(O)—, $(alkyl)_2NC(O)$—, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)— and the like.
The term "sulfamoyl" refers to $H_2NS(O)_2$—, alkyl-$NHS(O)_2$—, $(alkyl)_2NS(O)_2$—, aryl-$NHS(O)_2$—, alkyl(aryl)-$NS(O)_2$—, $(aryl)_2NS(O)_2$—, heteroaryl-$NHS(O)_2$—, aralkyl-$NHS(O)_2$—, heteroaralkyl-$NHS(O)_2$— and the like.
The term "sulfonamido" refers to alkyl-$S(O)_2$—NH—, aryl-$S(O)_2$—NH—, aralkyl-$S(O)_2$—NH—, heteroaryl-$S(O)_2$—NH—, heteroaralkyl-$S(O)_2$—NH—, alkyl-$S(O)_2$—N(alkyl)-, aryl-$S(O)_2$—N(alkyl)-, aralkyl-$S(O)_2$—N(alkyl)-, heteroaryl-$S(O)_2$—N(alkyl)-, heteroaralkyl-$S(O)_2$—N(alkyl)- and the like.
The term "sulfonyl" refers to alkylsulfonyl, arylsulfonyl, heteroarylsulfonyl, aralkylsulfonyl, heteroaralkylsulfonyl and the like.
The term "sulfonate" or "sulfonyloxy" refers to alkyl-$S(O)_2$—O—, aryl-$S(O)_2$—O—, aralkyl-$S(O)_2$—O—, heteroaryl-$S(O)_2$—O—, heteroaralkyl-$S(O)_2$—O— and the like.
The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carboxycarbonyl, carbamoyl, alkylaminothiocarbonyl, arylaminothiocarbonyl and the like.
The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to five substituents such as alkyl, trifluoromethyl, halo, hydroxy, alkoxy, acyl, alkanoyloxy, optionally substituted amino, thiol, alkylthio, nitro, cyano, carboxy, carboxyalkyl, alkoxycarbonyl, carbamoyl, alkylthiono, sulfonyl, sulfonamido, sulfonate, heterocyclyl and the like.
The term "monocyclic aryl" refers to optionally substituted phenyl as described under aryl.
The term "aralkyl" refers to an aryl group bonded directly through an alkyl group, such as benzyl.
The term "aralkanoyl" refers to aralkyl-C(O)—.
The term "aralkylthio" refers to aralkyl-S—.
The term "aralkoxy" refers to an aryl group bonded directly through an alkoxy group.
The term "arylsulfonyl" refers to aryl-$S(O)_2$—.
The term "arylthio" refers to aryl-S—.
The term "aroyl" refers to aryl-C(O)—.
The term "aroylamino" refers to aryl-C(O)—NH—.
The term "aryloxycarbonyl" refers to aryl-O—C(O)—.
The term "heterocyclyl" or "heterocyclo" refers to an optionally substituted, aromatic, or a partially or fully saturated nonaromatic cyclic group, for example, which is a 4- to 7-membered monocyclic, 7- to 12-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, benzodiazepinyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxoquinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups that are substituted with 1, 2 or 3 substituents selected from the group consisting of the following:

(a) optionally substituted alkyl;
(b) hydroxy (or protected hydroxy);
(c) halo;
(d) oxo (i.e. =O);
(e) optionally substituted amino, alkylamino or dialkylamino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl or sulfonamido;
(o) alkylcarbonyloxy;
(p) arylcarbonyloxy;
(q) arylthio;
(r) aryloxy;
(s) alkylthio;
(t) formyl;
(u) carbamoyl;
(v) aralkyl; and
(w) aryl substituted with alkyl, cycloalkyl, alkoxy, hydroxy, amino, acylamino, alkylamino, dialkylamino or halo.

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl, and the like, optionally substituted by e.g. lower alkyl, lower alkoxy or halo.

The term "heteroarylsulfonyl" refers to heteroaryl-$S(O)_2$—.

The term "heteroaroyl" refers to heteroaryl-C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heteroaralkanoylamino" refers to heteroaralkyl-C(O)NH—.

The term "acyl" refers to alkanoyl, cycloalkanoyl, aroyl, heteroaroyl, aralkanoyl, heteroaralkanoyl and the like.

The term "acyloxy" refers to alkanoyloxy, cycloalkanoyloxy, aroyloxy, heteroaroyloxy, aralkanoyloxy, heteroaralkanoyloxy and the like.

The term "acylamino" refers to alkanoylamino, cycloalkanoylamino, aroylamino, heteroaroylamino, aralkanoylamino, heteroaralkanoylamino and the like.

The term "esterified carboxy" refers to optionally substituted alkoxycarbonyl, cycloalkoxycarbonyl, aryloxycarbonyl, aralkoxycarbonyl, heterocyclooxycarbonyl and the like.

Pharmaceutically acceptable salts of any compound of the present invention refer to salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris(hydroxymethyl)-methyl-ammonium salts, and salts with amino acids.

Similarly acid addition salts, such as those formed with mineral acids, organic carboxylic acids and organic sulfonic acids e.g. hydrochloric acid, maleic acid and methanesulfonic acid, are possible provided a basic group, such as pyridyl, constitutes part of the structure.

As described herein above, the present invention provides 1,1-dioxo-1,2,5-thiadiazolidin-3-one derivatives of formula (I), pharmaceutical compositions containing the same, methods for preparing such compounds and methods of treating and/or preventing conditions associated with PTPase activity, in particular, PTP-1B and TC PTP activity, by administration of a therapeutically effective amount of a compound of the present invention, or a pharmaceutical composition thereof.

Preferred are the compounds of formula (I), designated as the A group, wherein

Q combined together with the carbon atoms to which it is attached form an aromatic, or a partially or fully saturated 5- to 6-membered carbocyclic ring;

or a pharmaceutically acceptable salt thereof.

Preferred are compounds in the A group having the formula

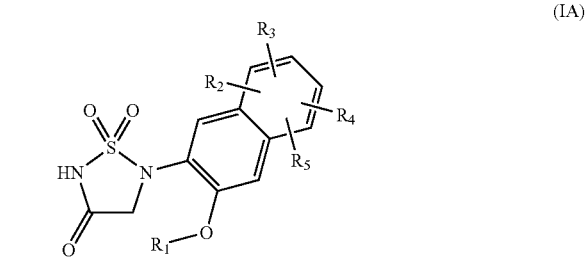

(IA)

wherein
  $R_1$ is hydrogen, —$C(O)R_6$, —$C(O)NR_7R_8$ or —$C(O)OR_9$ in which
    $R_6$ and $R_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
    $R_8$ and $R_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
  $R_2$, $R_3$, $R_4$ and $R_5$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or $(C_{1-8})$alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or
  $R_2$ and $R_3$ combined are alkylene which together with the ring atoms to which they are attached form a 5- to 7-membered fused ring; or or a pharmaceutically acceptable salt thereof.

Preferred are compounds of formula (IA) wherein
  $R_4$ and $R_5$ are hydrogen;

or a pharmaceutically acceptable salt thereof.

Further preferred are compounds of formula (IA) having the formula

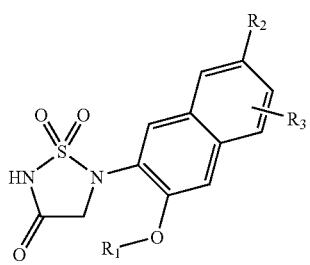

(IB)

wherein
  $R_1$ is hydrogen, —$C(O)R_6$, —$C(O)NR_7R_8$ or —$C(O)OR_9$ in which
    $R_6$ and $R_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
    $R_8$ and $R_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
  $R_2$ and $R_3$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or $(C_{1-8})$alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

or a pharmaceutically acceptable salt thereof.

Preferred are compounds of formula (IB) wherein
  $R_2$ is —Y—$(CH_2)_n$—$CR_{10}R_{11}$, —$(CH_2)_m$—X in which
    Y is oxygen or $S(O)_q$ in which q is zero or an integer of 1 or 2; or
    Y is trans CH=CH; or
    Y is absent;
    n is an integer from 1 to 6;
    $R_{10}$ and $R_{11}$ are, independently from each other, hydrogen or lower alkyl; or
    $R_{10}$ and $R_{11}$ combined are alkylene which together with the carbon atom to which they are attached form a 3- to 7-membered ring;
    m is zero or an integer of 1 or 2;
    X is hydroxy, alkoxy, cycloalkyl, cycloalkoxy, acyl, acyloxy, carbamoyl, cyano, trifluoromethyl, free or esterified carboxy, monocyclic aryl or heterocyclyl;

or a pharmaceutically acceptable salt thereof.

Further preferred are compounds of formula (IB) wherein
  $R_3$ is hydrogen;

or a pharmaceutically acceptable salt thereof.

Further preferred are also compounds of formula (IB) wherein
  n is an integer of 2 or 3;
  $R_{10}$ and $R_{11}$ are, independently from each other, hydrogen or lower alkyl;
  m is zero or 1;
  X is hydroxy, carbamoyl, cyano, trifluoromethyl, free or esterified carboxy, monocyclic aryl or heterocyclyl;

or a pharmaceutically acceptable salt thereof.

More preferred are compounds of formula (IB) wherein
  Y is absent;

or a pharmaceutically acceptable salt thereof.

Even more preferred are compounds of formula (IB) wherein
  n is 3;
  $R_{10}$ and $R_{11}$ are lower alkyl;
  m is zero or 1;
  X is hydroxy, cyano or free or esterified carboxy;

or a pharmaceutically acceptable salt thereof.

Most preferred are compounds of formula (IB) wherein
R$_{10}$ and R$_{11}$ are methyl;

or a pharmaceutically acceptable salt thereof.

Especially preferred are compounds of formula (IB) wherein
R$_1$ is hydrogen or —C(O)R$_6$ in which R$_6$ is monocyclic aryl;

or a pharmaceutically acceptable salt thereof.

Preferred are also compounds in the A group having the formula

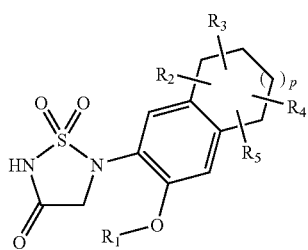

(IC)

wherein
R$_1$ is hydrogen or —C(O)R$_6$, —C(O)NR$_7$R$_8$ or —C(O)OR$_9$ in which
R$_6$ and R$_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_8$ and R$_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_2$, R$_3$, R$_4$ and R$_5$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or R$_2$ and R$_3$ combined are alkylene which together with the ring atoms to which they are attached form a 3- to 7-membered fused ring; or R$_2$ and R$_3$ combined are alkylene which together with the carbon atom to which they are attached form a 3- to 7-membered spirocyclic ring;

p is zero or 1;

or a pharmaceutically acceptable salt thereof.

Preferred are compounds of formula (IC) wherein
R$_4$ and R$_5$ are hydrogen;

or a pharmaceutically acceptable salt thereof.

Preferred are also compounds of formula (IC) wherein
R$_2$ and R$_3$ are, independently from each other, hydrogen, halogen or (C$_{1-4}$)alkyl optionally substituted by at least one halogen;

or a pharmaceutically acceptable salt thereof.

Preferred are also compounds of formula (IC) wherein
p is 1;

or a pharmaceutically acceptable salt thereof.

Further preferred are compounds of formula (IC) having the formula

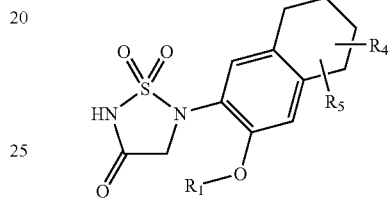

(ID)

wherein
R$_1$ is hydrogen or —C(O)R$_6$, —C(O)NR$_7$R$_8$ or —C(O)OR$_9$ in which
R$_6$ and R$_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_8$ and R$_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

R$_2$, R$_3$, R$_4$ and R$_5$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or (C$_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or R$_2$ and R$_3$ combined are alkylene which together with the carbon atom to which they are attached form a 3- to 7-membered spirocyclic ring;

or a pharmaceutically acceptable salt thereof.

Preferred are compounds of formula (ID) wherein
R$_4$ and R$_5$ are hydrogen;

or a pharmaceutically acceptable salt thereof.

Preferred are also compounds of formula (ID), designated as the B group, wherein
$R_2$ and $R_3$ are, independently from each other, hydrogen, halogen or $(C_{1-4})$alkyl optionally substituted by at least one halogen;

or a pharmaceutically acceptable salt thereof.
Preferred are compounds in the B group wherein
$R_1$ is hydrogen or —C(O)$R_6$ in which $R_6$ is monocyclic aryl;

or a pharmaceutically acceptable salt thereof.
Preferred are also compounds of formula (ID), designated as the C group, wherein
$R_2$ and $R_3$ combined are alkylene which together with the carbon atom to which they are attached form a 3- to 5-membered spirocyclic ring;

or a pharmaceutically acceptable salt thereof.
Preferred are compounds in the C group, wherein
$R_1$ is hydrogen or —C(O)$R_6$ in which $R_6$ is monocyclic aryl;

or a pharmaceutically acceptable salt thereof.
Preferred are also compounds of formula (ID), designated as the D group, wherein
$R_2$ is —Y—(CH$_2$)$_n$—CR$_{10}$R$_{11}$—(CH$_2$)$_m$—X in which
Y is oxygen or S(O)$_q$ in which q is zero or an integer of 1 or 2; or
Y is trans CH=CH; or
Y is absent;
n is an integer from 1 to 6;
$R_{10}$ and $R_{11}$ are, independently from each other, hydrogen or lower alkyl; or
$R_{10}$ and $R_{11}$ combined are alkylene which together with the carbon atom to which they are attached form a 3- to 7-membered ring;
m is zero or an integer of 1 or 2;
X is hydroxy, alkoxy, cycloalkyl, cycloalkoxy, acyl, acyloxy, carbamoyl, cyano, trifluoromethyl, free or esterified carboxy, monocyclic aryl or heterocyclyl;

or a pharmaceutically acceptable salt thereof.
Preferred are compounds in the D group wherein
$R_3$ is hydrogen;

or a pharmaceutically acceptable salt thereof.
Further preferred are compounds in the D group wherein
n is an integer of 2 or 3;
$R_{10}$ and $R_{11}$ are, independently from each other, hydrogen or lower alkyl;
m is zero or 1;
X is hydroxy, carbamoyl, cyano, trifluoromethyl, free or esterified carboxy, monocyclic aryl or heterocyclyl;

or a pharmaceutically acceptable salt thereof.
More preferred are compounds in the D group wherein
Y is absent;

or a pharmaceutically acceptable salt thereof.
Even more preferred are compounds in the D group wherein
n is 3;
$R_{10}$ and $R_{11}$ are lower alkyl;
m is zero or 1;
X is hydroxy, cyano or free or esterified carboxy;

or a pharmaceutically acceptable salt thereof.
Most preferred are compounds in the D group wherein
$R_{10}$ and $R_{11}$ are methyl;

or a pharmaceutically acceptable salt thereof.

Especially preferred are compounds in the D group wherein
$R_1$ is hydrogen or —C(O)$R_6$ in which $R_6$ is monocyclic aryl;

or a pharmaceutically acceptable salt thereof.
Particular embodiments of the invention are:
5-(3,6-Dihydroxynaphthalen-2-yl)-1,1-dioxo-1,2,5-thiadiazolidin-3-one;
5-(3,7-Dihydroxynaphthalen-2-yl)-1,1-dioxo-1,2,5-thiadiazolidin-3-one potassium salt;
5-(7-Bromo-3-hydroxynaphthalen-2-yl)-1,1-dioxo-1,2,5-thiadiazolidin-3-one;
5-(7-Ethyl-3-hydroxynaphthalen-2-yl)-1,1-dioxo-1,2,5-thiadiazolidin-3-one;
5-{3-Hydroxy-7-[2-(4-methoxyphenyl)-ethyl]-naphthalen-2-yl}-1,1-dioxo-1,2,5-thiadiazolidin-3-one;
5-{3-Hydroxy-7-[2-(4-trifluoromethylphenyl)-ethyl]-naphthalen-2-yl}-1,1-dioxo-1,2,5-thiadiazolidin- 3-one;
5-{3-Hydroxy-7-[2-(3-methoxyphenyl)-ethyl]-naphthalen-2-yl}-1,1-dioxo-1,2,5-thiadiazolidin-3-one;
5-[3-Hydroxy-7-(4-methylpentyl)-naphthalen-2-yl]-1,1-dioxo-1,2,5-thiadiazolidin-3-one;
{3-[6-Hydroxy-7-(1,1,4-trioxo-1,2,5-thiadiazolidin-2-yl)naphthalen-2-yl]-phenyl}-acetic acid;
5-(3-Hydroxy-7-phenylnaphthalen-2-yl)-1,1-dioxo-1,2,5-thiadiazolidin-3-one;
3-[6-Hydroxy-7-(1,1,4-trioxo-1,2,5-thiadiazolidin-2-yl)-naphthalen-2-yl]-benzoic acid;
5-[3-Hydroxy-7-(3-trifluoromethoxyphenyl)-naphthalen-2-yl]-1,1-dioxo-1,2,5-thiadiazolidin-3-one;
{3-[6-Hydroxy-7-(1,1,4-trioxo-1,2,5-thiadiazolidin-2-yl)naphthalen-2-yl]-phenyl}acetonitrile;
5-[3-Hydroxy-7-(3-hydroxymethylphenyl)-naphthalen-2-yl]-1,1-dioxo-1,2,5-thiadiazolidin-3-one;
3-{3-[6-Hydroxy-7-(1,1,4-trioxo-thiadiazolidin-2-yl)-naphthalen-2-yl]-phenyl}-propionic acid;
6-Hydroxy-7-(1,1,4-trioxo-1,2,5-thiadiazolidin-2-yl)-naphthalene-2-carbonitrile;
3-[6-Hydroxy-7-(1,1,4-trioxo-1,2,5-thiadiazolidin-2-yl)-naphthalen-2-yl]-benzonitrile;
5-[7-(3,3-Dimethylbutyl)-3-hydroxynaphthalen-2-yl]-1,1-dioxo-1,2,5-thiadiazolidin-3-one;
5-[3-Hydroxy-7-(3-trifluoromethylphenyl)-naphthalen-2-yl]-1,1-dioxo-1,2,5-thiadiazolidin-3-one;
3-[6-Hydroxy-7-(1,1,4-trioxo-1,2,5-thiadiazolidin-2-yl)-naphthalen-2-yl]-benzoic acid ethyl ester;
5-[3-Hydroxy-7-(3-methanesulfonylphenyl)-naphthalen-2-yl]-1,1-dioxo-1,2,5-thiadiazolidin-3-one;
3-{3-[6-Hydroxy-7-(1,1,4-trioxo-1,2,5-thiadiazolidin-2-yl)-naphthalen-2-yl]-phenyl}-propionitrile;
5-[3-Hydroxy-7-(3-methoxymethylphenyl)-naphthalen-2-yl]-1,1-dioxo-1,2,5-thiadiazolidin-3-one;
5-(7-Furan-3-yl-3-hydroxynaphthalen-2-yl)-1,1-dioxo-1,2,5-thiadiazolidin-3-one;
N-{3-[6-Hydroxy-7-(1,1,4-trioxo-1,2,5-thiadiazolidin-2-yl)-naphthalen-2-yl]-phenyl}-methanesulfonamide;
5-[7-(2-Fluorophenyl)-3-hydroxynaphthalen-2-yl]-1,1-dioxo-1,2,5-thiadiazolidin-3-one;
5-(3-Hydroxy-7-o-tolyinaphthalen-2-yl)-1,1-dioxo-1,2,5-thiadiazolidin-3-one;
5-(3-Hydroxy-7-pentylnaphthalen-2-yl)-1,1-dioxo-1,2,5-thiadiazolidin-3-one;
5-(3-Hydroxy-7-propylnaphthalen-2-yl)-1,1-dioxo-1,2,5-thiadiazolidin-3-one;
5-[3-Hydroxy-7-(tetrahydrofuran-3-yl)-naphthalen-2-yl]-1,1-dioxo-1,2,5-thiadiazolidin-3-one;

{3-[6-Hydroxy-7-(1,1,4-trioxo-1,2,5-thiadiazolidin-2-yl)-naphthalen-2-yl]-phenyl}-acetic acid ethyl ester;
3-{3-[6-Hydroxy-7-(1,1,4-trioxo-1,2,5-thiadiazolidin-2-yl)-naphthalen-2-yl]-phenyl}-propionic acid ethyl ester;
5-[6-Hydroxy-7-(1,1,4-trioxo-1,2,5-thiadiazolidin-2-yl)-naphthalen-2-yl]-pentanoic acid ethyl ester;
4-[6-Hydroxy-7-(1,1,4-trioxo-1,2,5-thiadiazolidin-2-yl)-naphthalen-2-yl]-2,2-dimethyl-butyric acid;
5-[3-Hydroxy-7-((S)-4-hydroxypentyl)-naphthalen-2-yl]-1,1-dioxo-1,2,5-thiadiazolidin-3-one;
4-[6-Hydroxy-7-(1,1,4-trioxo-1,2,5-thiadiazolidin-2-yl)-naphthalen-2-yl]-2-methylbutyronitrile;
5-[6-Hydroxy-7-(1,1,4-trioxo-1,2,5-thiadiazolidin-2-yl)-naphthalen-2-yl]-2-methylpentanoic acid ethyl ester;
5-[3-Hydroxy-7-(3-methylbutyl)-naphthalen-2-yl]-1,1-dioxo-1,2,5-thiadiazolidin-3-one;
5-[6-Hydroxy-7-(1,1,4-trioxo-1,2,5-thiadiazolidin-2-yl)-naphthalen-2-yl]-2,2-dimethylpentanenitrile;
5-[6-Hydroxy-7-(1,1,4-trioxo-1,2,5-thiadiazolidin-2-yl)-naphthalen-2-yl]-pentanoic acid;
5-[3-Hydroxy-7-(5-hydroxypentyl)-naphthalen-2-yl]-1,1-dioxo-1,2,5-thiadiazolidin-3-one;
2-Hydroxy-6-{2-[6-hydroxy-7-(1,1,4-trioxo-1,2,5-thiadiazolidin-2-yl)-naphthalen-2-yloxy]-ethoxy}-N,N-dimethylbenzamide;
2-Hydroxy-6-{4-[6-hydroxy-7-(1,1,4-trioxo-1,2,5-thiadiazolidin-2-yl)-naphthalen-2-yl]-butoxy}-N,N-dimethylbenzamide;
5-{3-Hydroxy-7-[3-(2-hydroxyethoxy)-propyl]-naphthalen-2-yl}-1,1-dioxo-1,2,5-thiadiazolidin-3-one;
5-{3-Hydroxy-7-[2-(2-methoxyphenyl)-ethyl]-naphthalen-2-yl}-1,1-dioxo-1,2,5-thiadiazolidin-3-one;
5-[3-Hydroxy-7-(5-oxohexyl)-naphthalen-2-yl]-1,1-dioxo-1,2,5-thiadiazolidin-3-one;
5-{7-[3-(3,5-Dimethylpyrazol-1-yl)-propyl]-3-hydroxy-naphthalen-2-yl}-1,1-dioxo-1,2,5-thiadiazolidin-3-one;
5-{3-Hydroxy-7-[3-(2-oxocyclohexyl)-propyl]-naphthalen-2-yl}-1,1-dioxo-1,2,5-thiadiazolidin-3-one;
5-{3-Hydroxy-7-[4-hydroxy-4-(tetrahydrofuran-2-yl)-butyl]-naphthalen-2-yl}-1,1-dioxo-1,2,5-thiadiazolidin-3-one;
5-{3-Hydroxy-7-[1-(2-oxopyrrolidin-1-yl)-ethyl]naphthalen-2-yl}-1,1-dioxo-1,2,5-thiadiazolidin-3-one;
5-[3-Hydroxy-7-(3-phenylpropyl)-naphthalen-2-yl]-1,1-dioxo-1,2,5-thiadiazolidin-3-one;
5-[3-Hydroxy-7-(3-pentafluorophenylpropyl)-naphthalen-2-yl]-1,1-dioxo-1,2,5-thiadiazolidin-3-one;
2-{3-[6-Hydroxy-7-(1,1,4-trioxo-1,2,5-thiadiazolidin-2-yl)-naphthalen-2-yl]-propyl}benzonitrile;
5-[3-Hydroxy-7-((R)-4-hydroxypentyl)-naphthalen-2-yl]-1,1-dioxo-1,2,5-thiadiazolidin-3-one;
5-[3-Hydroxy-7-(4-hydroxypentyl)-naphthalen-2-yl]-1,1-dioxo-1,2,5-thiadiazolidin-3-one;
5-[3-Hydroxy-7-(4-hydroxy-3-methylbutyl)-naphthalen-2-yl]-1,1-dioxo-1,2,5-thiadiazolidin-3-one;
5-[7-(4-Ethyl-4-hydroxyhexyl)-3-hydroxynaphthalen-2-yl]-1,1-dioxo-1,2,5-thiadiazolidin-3-one;
5-[3-Hydroxy-7-(4-hydroxyheptyl)-naphthalen-2-yl]-1,1-dioxo-1,2,5-thiadiazolidin-3-one;
5-{3-Hydroxy-7-[3-(1-hydroxycyclohexyl)-propyl]-naphthalen-2-yl}-1,1-1,2,5-thiadiazolidin-3-one;
5-[6-Hydroxy-7-(1,1,4-trioxo-1,2,5-thiadiazolidin-2-yl)-naphthalen-2-yl]-2,2-dimethylpentanoic acid;
5-{3-Hydroxy-7-[2-((1S,2R)-2-hydroxycyclopentyl)-ethyl]-naphthalen-2-yl}-1,1-dioxo-1,2,5-thiadiazolidin-3-one;
5-[6-Hydroxy-7-(1,1,4-trioxo-1,2,5-thiadiazolidin-2-yl)-naphthalen-2-yl]-pentanenitrile;
5-{3-Hydroxy-7-[3-(2-hydroxycyclohexyl)-propyl]-naphthalen-2-yl}-1,1-dioxo-1,2,5-thiadiazolidin-3-one;
5-[6-Hydroxy-7-(1,1,4-trioxo-1,2,5-thiadiazolidin-2-yl)-naphthalen-2-yl]-2,2-dimethylpentanoic acid methyl ester;
5-[3-Hydroxy-7-(5,5,5-trifluoro-4-hydroxy-4-methylpentyl)-naphthalen-2-yl]-1-dioxo-1,2,5-thiadiazolidin-3-one;
Acetic acid 4-[6-hydroxy-7-(1,1,4-trioxo-1,2,5-thiadiazolidin-2-yl)-naphthalen-2-yl]-2-methyl butyl ester;
5-[3-Hydroxy-7-(5,5,5-trifluoro-4-hydroxypentyl)-naphthalen-2-yl]-1,1-dioxo-1,2,5-thiadiazolidin-3-one;
5-[3-Hydroxy-7-(4-hydroxy-4-methylpentyl)-naphthalen-2-yl]-1,1-dioxo-1,2,5-thiadiazolidin-3-one;
5-(7-Cyclopentyl-3-hydroxynaphthalen-2-yl)-1,1-dioxo-1,2,5-thiadiazolidin-3-one;
5-(7-Cyclohexyl-3-hydroxynaphthalen-2-yl)-1,1-dioxo-1,2,5-thiadiazolidin-3-one;
5-[3-Hydroxy-7-(3-methylsulfanylphenyl)-naphthalen-2-yl]-1,1-dioxo-1,2,5-thiadiazolidin-3-one;
5-[3-Hydroxy-7-((E)-4-hydroxy-4-methylpent-1-enyl)-naphthalen-2-yl]-1,1-dioxo-1,2,5-thiadiazolidin-3-one;
5-[6-Hydroxy-7-(1,1,4-trioxo-1,2,5-thiadiazolidin-2-yl)-naphthalen-2-yl]-thiophene-2-carbonitrile;
{3-[6-Hydroxy-7-(1,1,4-trioxo-1,2,5-thiadiazolidin-2-yl)-naphthalen-2-yl]-benzyl}-carbamic acid methyl ester;
(E)-5-[6-Hydroxy-7-(1,1,4-trioxo-1,2,5-thiadiazolidin-2-yl)-naphthalen-2-yl]-pent-4-enenitrile;
(E)-5-[6-Hydroxy-7-(1,1,4-trioxo-1,2,5-thiadiazolidin-2-yl)-naphthalen-2-yl]-2-methylpent-4-enoic acid ethyl ester;
(E)-5-[6-Hydroxy-7-(1,1,4-trioxo-1,2,5-thiadiazolidin-2-yl)naphthalen-2-yl]-2-methylpent-4-enoic acid;
(E)-5-[6-Hydroxy-7-(1,1,4-trioxo-1,2,5-thiadiazolidin-2-yl)-naphthalen-2-yl]-pent-4-enoic acid;
5-[6-Hydroxy-7-(1,1,4-trioxo-1,2,5-thiadiazolidin-2-yl)-naphthalen-2-yl]-pentanoic acid isopropyl ester;
5-[6-Hydroxy-7-(1,1,4-trioxo-1,2,5-thiadiazolidin-2-yl)-naphthalen-2-yl]-2-methylpentanoic acid methyl ester;
5-[6-Hydroxy-7-(1,1,4-trioxo-1,2,5-thiadiazolidin-2-yl)-naphthalen-2-yl]-2-methylpentanoic acid;
5-[7-(4,5-Dihydroxy-4,5-dimethylhex-1-enyl)-3-hydroxynaphthalen-2-yl]-1,1-dioxo-1,2,5-thiadiazolidin-3-one;
5-[7-(4,5-Dihydroxy-4,5-dimethylhexyl)-3-hydroxynaphthalen-2-yl]-1,1-dioxo-1,2,5-thiadiazolidin-3-one;
5-[7-(4,4-Dimethylpentyl)-3-hydroxynaphthalen-2-yl]-1,1-dioxo-1,2,5-thiadiazolidin-3-one;
Benzoic acid 6-(3-cyano-3-methylpropyl)-3-(1,1,4-trioxo-1,2,5-thiadiazolidin-2-yl)-naphthalen-2-yl ester;
2,2-Dimethylpropionic acid 6-(3-cyano-3-methylpropyl)-3-(1,1,4-trioxo-1,2,5-thiadiazolidin-2-yl)-naphthalen-2-yl ester;
Propionic acid 6-(3-cyano-3-methylpropyl)-3-(1,1,4-trioxo-1,2,5-thiadiazolidin-2-yl)-naphthalen-2-yl ester;
2-Ethylbutyric acid 6-(3-cyano-3-methylpropyl)-3-(1,1,4-trioxo-1,2,5-thiadiazolidin-2-yl)-naphthalen-2-yl ester;
Hexanoic acid 6-(3-cyano-3-methylpropyl)-3-(1,1,4-trioxo-1,2,5-thiadiazolidin-2-yl)-naphthalen-2-yl ester;
2-Acetoxy-benzoic acid 6-(3-cyano-3-methylpropyl)-3-(1,1,4-trioxo-1,2,5-thiadiazolidin-2-yl)-naphthalen-2-yl ester;
Pentanoic acid 6-(3-cyano-3-methylpropyl)-3-(1,1,4-trioxo-1,2,5-thiadiazolidin-2-yl)-naphthalen-2-yl ester;
Acetic acid 6-(3-cyano-3-methylpropyl)-3-(1,1,4-trioxo-1,2,5-thiadiazolidin-2-yl)-naphthalen-2-yl ester;
3-Methylbenzoic acid 6-(3-cyano-3-methylpropyl)-3-(1,1,4-trioxo-1,2,5-thiadiazolidin-2-yl)-naphthalen-2-yl ester;
2-Methylbenzoic acid 6-(3-cyano-3-methylpropyl)-3-(1,1,4-trioxo-1,2,5-thiadiazolidin-2-yl)-naphthalen-2-yl ester;

4-Butylbenzoic acid 6-(3-cyano-3-methylpropyl)-3-(1,1,4-trioxo-1,2,5-thiadiazolidin-2-yl)-naphthalen-2-yl ester;
Cyclohexanecarboxylic acid 6-(3-cyano-3-methylpropyl)-3-(1,1,4-trioxo-1,2,5-thiadiazolidin-2-yl)-naphthalen-2-yl ester;
4-tert-Butylbenzoic acid 6-(3-cyano-3-methylpropyl)-3-(1,1,4-trioxo-1,2,5-thiadiazolidin-2-yl)-naphthalen-2-yl ester;
2,2-Dimethylpropionic acid 6-(3-cyanophenyl)-3-(1,1,4-trioxo-1,2,5-thiadiazolidin-2-yl)-naphthalen-2-yl ester;
Benzoic acid 6-(4-ethoxycarbonylbutyl)-3-(1,1,4-trioxo-1,2,5-thiadiazolidin-2-yl)-naphthalen-2-yl ester;
Benzoic acid 6-(3-methylbutyl)-3-(1,1,4-trioxo-1,2,5-thiadiazolidin-2-yl)-naphthalen-2-yl ester;
Benzoic acid 6-((E)-4-hydroxy-4-methylpent-1-enyl)-3-(1,1,4-trioxo-1,2,5-thiadiazolidin-2-yl)-naphthalen-2-yl ester;
Benzoic acid 6-methyl-3-(1,1,4-trioxo-1,2,5-thiadiazolidin-2-yl)-naphthalen-2-yl ester;
Benzoic acid 6-(5-hydroxy-4,4-dimethylpentyl)-3-(1,1,4-trioxo-1,2,5-thiadiazolidin-2-yl)-naphthalen-2-yl ester;
5-[3-Hydroxy-7-(5-hydroxy-4,4-dimethylpentyl)-naphthalen-2-yl]-1,1-dioxo-1,2,5-thiadiazolidin-3-one;
5-(3-Hydroxy-5,6,7,8-tetrahydronapthalen-2-yl)-1,1-dioxo-1,2,5-thiadiazolidin-3-one;
5-(3,6-Dihydroxy-5,6,7,8-tetrahydronaphthalen-2-yl)-1,1-dioxo-1,2,5-thiadiazolidin-3-one;
5-(3-Hydroxy-6-methoxy-5,6,7,8-tetrahydronaphthalen-2-yl)-1,1-dioxo-1,2,5-thiadiazolidin-3-one;
5-(6-Ethoxy-3-hydroxy-5,6,7,8-tetrahydronaphthalen-2-yl)-1,1-dioxo-1,2,5-thiadiazolidin-3-one;
5-(3-Hydroxy-7-methyl-5,6,7,8-tetrahydronaphthalen-2-yl)-1,1-dioxo-1,2,5-thiadiazolidin-3-one;
5-(3-Hydroxy-7,7-dimethyl-5,6,7,8-tetrahydronaphthalen-2-yl)-1,1-dioxo-1,2,5-thiadiazolidin-3-one;
5-(3-Hydroxy-7-trifluoromethyl-5,6,7,8-tetrahydronaphthalen-2-yl)-1,1-dioxo-1,2,5-thiadiazolidin-3-one;
5-(3-Hydroxy-7-isopropyl-5,6,7,8-tetrahydronaphthalen-2-yl)-1,1-dioxo-1,2,5-thiadiazolidin-3-one;
5-(7-Ethyl-3-hydroxy-5,6,7,8-tetrahydronaphthalen-2-yl)-1,1-dioxo-1,2,5-thiadiazolidin-3-one;
5-(7,7-Diethyl-3-hydroxy-5,6,7,8-tetrahydronaphthalen-2-yl)-1,1-dioxo-1,2,5-thiadiazolidin-3-one;
5-(3-Hydroxy-7,7-dipropyl-5,6,7,8-tetrahydronaphthalen-2-yl)-1,1-dioxo-1,2,5-thiadiazolidin-3-one;
5-(6'-Hydroxy-3',4'-dihydro-1'H-spiro[cyclopentane-1,2'-naphthalen]-7'-yl) 1,2,5-thiadiazolidin-3-one 1,1-dioxide;
5-((S)-7-Ethyl-3-hydroxy-5,6,7,8-tetrahydronaphthalen-2-yl)-1,1-dioxo-1,2,5-thiadiazolidin-3-one;
5-[6-Hydroxy-7-(1,1,4-trioxo-1,2,5-thiadiazolidin-2-yl)-1,2,3,4-tetrahydronaphthalen-2-yl]-2,2-dimethylpentanoic acid methyl ester;
5-[6-Hydroxy-7-(1,1,4-trioxo-1,2,5-thiadiazolidin-2-yl)-1,2,3,4-tetrahydronaphthalen-2-yl]-2,2-dimethylpentanoic acid;
5-(6-Hydroxy-2-methyl-2,3-dihydrobenzo[b]thiophen-5-yl)-1,1-dioxo-1,2,5-thiadiazolidin-3-one;
5-(6-Hydroxyindan-5-yl)-1,1-dioxo-1,2,5-thiadiazolidin-3-one;
5-(6-Hydroxy-2,2-dimethylindan-5-yl)-1,1-dioxo-1,2,5-thiadiazolidin-3-one;
5-(6-Hydroxy-2-methylindan-5-yl)-1,1-dioxo-1,2,5-thiadiazolidin-3-one;
Benzoic acid 6,6-dimethyl-3-(1,1,4-trioxo-1,2,5-thiadiazolidin-2-yl)-5,6,7,8-tetrahydronaphthalen-2-yl ester;
Benzoic acid (S)-6-ethyl-3-(1,1,4-trioxo-1,2,5-thiadiazolidin-2-yl)-5,6,7,8-tetrahydronaphthalen-2-yl ester;
Benzoic acid 6-ethyl-3-(1,1,4-trioxo-1,2,5-thiadiazolidin-2-yl)-5,6,7,8-tetrahydronaphthalen-2-yl ester;
Benzoic acid 6,6-diethyl-3-(1,1,4-trioxo-1,2,5-thiadiazolidin-2-yl)-5,6,7,8-tetrahydronaphthalen-2-yl ester;
Benzoic acid 2,2-dimethyl-6-(1,1,4-trioxo-1,2,5-thiadiazolidin-2-yl)-indan-5-yl ester;
5-(3-Allyloxy-6-hydroxybenzo[d]isoxazol-5-yl)-1,1-dioxo-1,2,5-thiadiazolidin-3-one;
5-Hydroxy-6-(1,1,4-trioxo-1,2,5-thiadiazolidin-2-yl)-1H-indole-2-carboxylic acid ethyl ester potassium salt;
5-Hydroxy-6-(1,1,4-trioxo-1,2,5-thiadiazolidin-2-yl)-1H-indole-2-carboxylic acid 3-methyl-butyl ester;
5-Hydroxy-6-(1,1,4-trioxo-1,2,5-thiadiazolidin-2-yl)-1H-indole-2-carboxylic acid isobutyl ester;
5-Hydroxy-6-(1,1,4-trioxo-1,2,5-thiadiazolidin-2-yl)-1H-indole-2-carboxylic acid; and
5-(7-Hydroxy-3-methoxy-2-oxo-2H-chromen-6-yl)-1,1-dioxo-1,2,5-thiadiazolidin-3-one;
5-[3-Hydroxy-7-((E)-propenyl)-naphthalen-2-yl]-1,1-dioxo-[1,2,5]thiadiazolidin-3-one;
5-(3-Hydroxy-7-vinyl-naphthalen-2-yl)-1,1-dioxo-[1,2,5]thiadiazolidin-3-one;
4-[6-Hydroxy-7-(1,1,4-trioxo-[1,2,5]thiadiazolidin-2-yl)-naphthalen-2-yl]-butyric acid methyl ester;
5-{3-Hydroxy-7-[3-(2,2,2-trifluoro-ethoxy)-propyl]-naphthalen-2-yl}-1,1-dioxo-[1,2,5]thiadiazolidin-3-one;
4-[6-Hydroxy-7-(1,1,4-trioxo-[1,2,5]thiadiazolidin-2-yl)-naphthalen-2-yl]-butyric acid;
0.5-[3-Hydroxy-7-(3-phenyl-propyl)-naphthalen-2-yl]-1,1-dioxo-[1,2,5]thiadiazolidin-3-one;
3-{3-[6-Hydroxy-7-(1,1,4-trioxo-thiadiazolidin-2-yl)-naphthalen-2-yl]-phenyl}-propionic acid;

or a pharmaceutically acceptable salt thereof.

The compounds of the invention depending on the nature of the substituents, may possess one or more asymmetric centers. The resulting diastereoisomers, enantiomers and geometric isomers are encompassed by the instant invention.

Compounds of formula (I) may be prepared starting, e.g., by cyclizing compounds of the formula

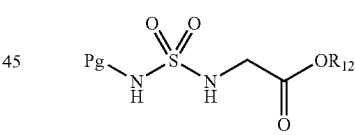

(II)

wherein Pg is an appropriate N-protecting group such as 4-methoxybenzyl, 2,4-dimethoxybenzyl or 2-trimethylsilyl-ethyl, and $R_{12}$ is hydrogen to afford compounds of the formula

(III)

wherein Pg has a meaning as defined herein above, by treatment with a coupling agent such as diisopropyl carbodiimide (DIC) or 1-ethyl-3-(3-dimethylaminopropyl)carbodiimide hydrochloride (EDCI) in the presence a base such as triethylamine (TEA) or N-methyl-morpholine (NMM) in an organic solvent such as tetrahydrofuran (THF), N,N-dimethyl-formamide (DMF) or dichoromethane (DCM). The reaction may be carried out in the presence of an additive such as of hydroxybenzotriazole (HOBt).

Compounds of formula (II) wherein $R_{12}$ is hydrogen may be obtained from compounds of formula (II) wherein $R_{12}$ is an alkyl group according to methods well known in the art, e.g. compounds of formula (II) in which $R_{12}$ is methyl or ethyl can be treated with an aqueous base such as sodium, or potassium hydroxide in an organic solvent such as THF, 1,4-dioxane, methanol (MeOH) or ethanol (EtOH) to afford compounds of formula (II) wherein $R_{12}$ is hydrogen, or compounds of formula (II) in which $R_{12}$ is t-butyl may be treated with an acid such as hydrochloric acid (HCl) or trifluoroacetic acid (TFA) in an organic solvent such as DCM or ethyl acetate (EtOAc) to afford compounds of formula (II) wherein $R_{12}$ is hydrogen.

Compounds of formula (II) wherein $R_{12}$ is an alkyl group such as methyl, ethyl or t-butyl, and the like, may be obtained analogously to a literature procedure described by Ducry et al. in *Helvetica Chimica Acta*, 1999, 82, 2432.

Resulting compounds of formula (III) wherein Pg has a meaning as defined herein can then be coupled with a variety of boronic acid derivatives of the formula

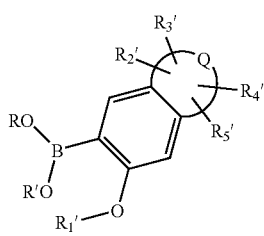

(IV)

wherein $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively, and R and R' are hydrogen or lower alkyl, or R and R' combined are alkylene which together with the boron and the oxygen atoms form a 5- or 6-membered ring, in the presence of a copper catalyst such as copper(II) acetate and a base such as cesium(II) carbonate ($CS_2CO_3$) or TEA in an organic solvent such as THF, 1,4-dioxane or DCM to form compounds of the formula

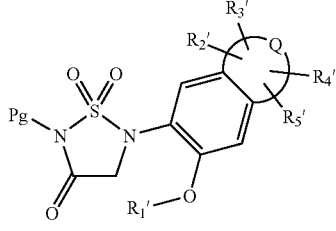

(V)

wherein Pg, $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively. Alternatively, compounds of formula (III) may be coupled with a boroxine derivative corresponding to a boronic acid derivative of formula (IV) as described, e.g., by Chan et al. in *Tet. Lett.* 2003, 44, 3863.

Compounds of formula (IV) are known, or if they are novel, they may be prepared using methods well known in the art, or as illustrated herein in the Examples, or modifications thereof.

Alternatively, compounds of formula (V) wherein $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively, may be obtained by reacting a compound of formula (III) wherein Pg has a meaning as defined herein with compounds of the formula

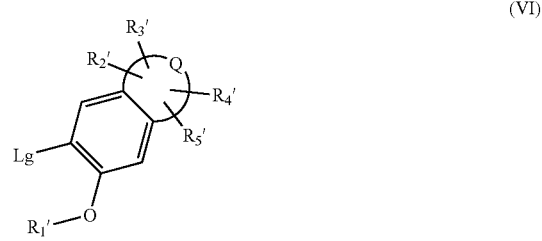

(VI)

wherein Lg represents a leaving group such as halide or trifluoromethanesulfonate, preferably fluoride or chloride, and $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively, using conditions well know in the art or using methods described herein or modifications thereof, e.g., a compound of formula (III) may be first treated with a base such as $Cs_2CO_3$, or sodium, lithium or potassium bis(trimethylsilyl) amide in an inert organic solvent such as THF or 1,4-dioxane followed by reaction with a compound of formula (VI) at a temperature ranging from room temperature (RT) to 110° C.

Compounds of formula (VI) are known, or if they are novel, they may be prepared using methods well known in the art, or as illustrated herein in the Examples, or modifications thereof.

Compounds of formula (V) wherein Pg; $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively, can be converted to compounds of the formula

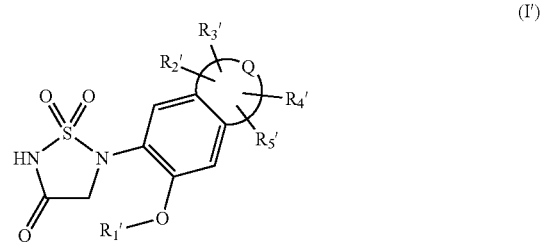

(I')

by removal of the N-protecting group according to methods well known in the art, e.g. in particular when Pg is 4-methoxybenzyl or 2,4-dimethoxybenzyl group using hydrogen in the presence of a catalyst such as palladium on carbon in a polar organic solvent such as MeOH or EtOAc, or by treatment with an acid such as TFA in an organic solvent such as DCM, preferably in the presence of an additive such as t-butyldimethylsilane or triethylsilane, or in particular when Pg is trimethylsilylethyl group using a fluoride reagent such as tetra-n-butylammoniumfluoride in an organic solvent such as THF or 1,4-dioxane.

In addition, compounds of formula (I') wherein $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively, may be prepared by condensing compounds of the formula

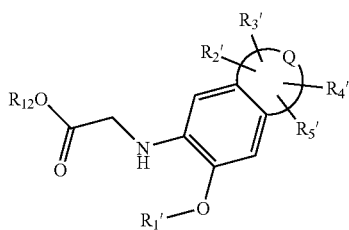
(VII)

wherein $R_{12}$ has a meaning as defined herein above, with sulfamoyl chloride analogs of the formula

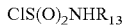
ClS(O)$_2$NHR$_{13}$     (VIII)

wherein $R_{13}$ is hydrogen or alkoxycarbonyl such as t-butoxycarbonyl or 2-trimethylsilyl-ethoxycarbonyl in the presence of a base such as TEA or NMM in an organic solvent such as acetonitrile (MeCN), DCM or THF to form compounds of the formula

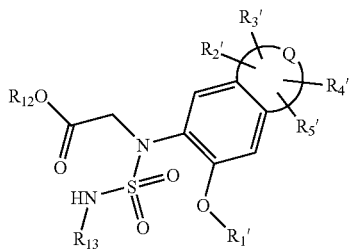
(IX)

wherein $R_{12}$ and $R_{13}$ have meanings as defined herein, and $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively.

Compounds of formula (VIII) wherein $R_{13}$ is alkoxycarbonyl may be obtained by reacting chlorosulfonyl isocyanate with the appropriate alcohol in an organic solvent such as MeCN, DCM or THF.

Compounds of formula (VII) may be prepared using methods well known in the art or according to methods described herein or modifications thereof, e.g., under conditions of reductive amination, or according to the method described by Tohru Fukuyama et al. in *Tet. Lett.*, 1997, 38 (33), 5831; or by reacting amines of the formula

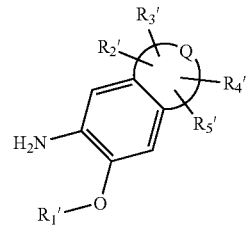
(X)

wherein $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively, with an acetate of the formula

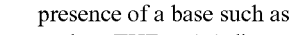
Lg'-CH$_2$—C(O)—O—R$_{12}$     (XI)

wherein Lg' and $R_{12}$ have meanings as defined herein, in the presence of a base such as TEA or NMM in an inert solvent such as THF or 1,4-dioxane.

Amines of formula (X) are known, or if they are novel, they may be obtained according to methods well known in the art, or as described herein in the illustrative Examples, or using modifications thereof.

Compounds of formula (IX) wherein $R_{12}$ has a meaning as defined herein, and $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively, and $R_{13}$ is alkoxycarbonyl may be converted to compounds of formula (IX) wherein $R_{13}$ is hydrogen according to methods known in the art or using methods described herein or modifications thereof, e.g., compounds of formula (IX) wherein $R_{13}$ is t-butoxycarbonyl may be treated with an acid such as TFA, neat or in an extrinsic organic solvent such as DCM, or compounds of formula (IX) wherein $R_{13}$ is 2-trimethylsilylethoxycarbonyl may be treated with a fluoride reagent such as tetra-n-butylammoniumfluoride in an organic solvent such as THF or 1,4-dioxane to afford compounds of formula (IX) wherein $R_{13}$ is hydrogen.

Compounds of formula (IX) wherein $R_{12}$ has a meaning as defined herein, and $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively, and $R_{13}$ is hydrogen can be cyclized to form compounds of formula (I') using methods and conditions well known in the art or as illustrated with Examples herein or modifications thereof.

Alternatively, compounds of formula (IX) wherein $R_{12}$ has a meaning as defined herein; $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$; $R_4$ and $R_5$, respectively; and $R_{13}$ is hydrogen, may be obtained by first condensing amines of formula (X) with sulfamide in an aqueous solution and in the presence of a base such as sodium bicarbonate (NaHCO$_3$) at an elevated temperature, preferably at the boiling point of the solution, to afford compounds of the formula

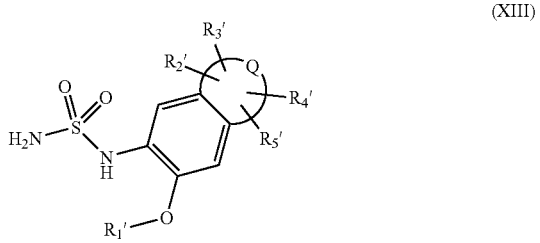

(XIII)

wherein $R_1'$, $R_2'$, $R_3'$, $R_4'$ and $R_5'$ have meanings as defined herein for $R_1$, $R_2$, $R_3$, $R_4$ and $R_5$, or $R_1'$, $R_2'$, $R_3'$, $R_4'$ and $R_5'$ are groups convertible to $R_1$, $R_2$, $R_3$, $R_4$ and $R_5$, respectively. Compound of formula (XII) may then be converted to compound of formula (IX) in which $R_{13}$ is hydrogen by the reaction with acetates of formula (XI) in the presence of a base such as sodium hydride in an inert solvent such as THF or DMF.

In starting compounds and intermediates which are converted to the compounds of the invention in a manner described herein, functional groups present, such as amino, thiol, carboxyl, and hydroxy groups, are optionally protected by conventional protecting groups that are common in preparative organic chemistry. Protected amino, thiol, carboxyl, and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well known protecting groups that meet these conditions and their introduction and removal are described, for example, in McOmie, "*Protective Groups in Organic Chemistry*", Plenum Press, London, New York (1973); and Greene and Wuts, "*Protective Groups in Organic Synthesis*", John Wiley and Sons, Inc, New York (1999).

The above mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, optical isomers (enantiomers, antipodes), racemates, or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example by chromatography and/or fractional crystallization.

Any resulting racemates of final products or intermediates can be resolved into the optical antipodes by known methods, e.g. by separation of the diastereoisomeric salts thereof, obtained with an optically active acid or base, and liberating the optically active acidic or basic compound. The carboxylic acid intermediates can thus be resolved into their optical antipodes e.g. by fractional crystallization of D- or L-(alpha-methylbenzylamine, cinchonidine, cinchonine, quinine, quinidine, ephedrine, dehydroabietylamine, brucine or strychnine)-salts. Racemic products can also be resolved by chiral chromatography, e.g. high pressure liquid chromatography using a chiral adsorbent.

Finally, compounds of the invention are either obtained in the free form, as a salt thereof if salt forming groups are present or as prodrug derivatives thereof.

In particular, the NH-group of the 1,1-dioxo-1,2,5-thiadiazolidin-3-one moiety, may be converted into salts with pharmaceutically acceptable bases. Salts may be formed using conventional methods, advantageously in the presence of an ethereal or alcoholic solvent, such as a lower alkanol. From the solutions of the latter, the salts may be precipitated with ethers, e.g. diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as $(C_{1-4})$alkanecarboxylic acids which, for example, are unsubstituted or substituted by halogen, for example acetic acid, such as saturated or unsaturated dicarboxylic acids, for example oxalic, succinic, maleic or fumaric acid, such as hydroxy-carboxylic acids, for example glycolic, lactic, malic, tartaric or citric acid, such as amino acids, for example aspartic or glutamic acid, or with organic sulfonic acids, such as $(C_{1-4})$alkyl-sulfonic acids (for example methanesulfonic acid) or arylsulfonic acids which are unsubstituted or substituted (for example by halogen). Preferred are salts formed with hydrochloric acid, methanesulfonic acid and maleic acid.

Prodrug derivatives of any compound of the present invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

As described herein above, the compounds of the present invention are inhibitors of PTPases and, thus, may be employed for the treatment of conditions mediated by the PTPases. Accordingly, the compounds of formula (I) may be employed for treatment of insulin resistance; glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Accordingly, the compounds of formula (I) may be employed for treatment of insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by PTPase activity, in particular, PTP-1B and TC PTP activity. Such conditions include e.g. insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbants, colorants, flavors and sweeteners. Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by PTPases, preferably, insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Accordingly, the present invention provides pharmaceutical compositions as described above for the treatment of conditions mediated by PTPases, preferably, insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) anti-diabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; thiazolidone derivatives such as glitazones, e.g., pioglitazone and rosiglitazone; glucokinase activators; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; modulators of PPARs (peroxisome proliferator-activated receptors), e.g., non-glitazone type PPARγ agonists such as N-(2-benzoylphenyl)-L-tyrosine analogues, e.g. GI-262570, and JTT501; DPPIV (dipeptidyl peptidase IV) inhibitors such as LAF237, MK-0431, saxagliptin and GSK23A; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products);

b) anti-dyslipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; HDL increasing compounds such as cholesterol ester transfer protein (CETP) inhibitors, e.g., JTT705; Apo-A1 analogs and mimetics; squalene synthase inhibitors; FXR (farnesoid X receptor) and LXR (liver X receptor) ligands; cholestyramine; fibrates; nicotinic acid; and aspirin;

c) anti-obesity agents such as phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine, ecopipam, ephedrine, and pseudoephedrine; cholesterol absorption modulators such as ZETIA® and KT6-971; and cannabinoid receptor antagonists such as rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists such as eplerenone; and aldosterone synthase inhibitors such as anastrazole and fadrazole.

Other specific anti-diabetic compounds are described by Patel Mona in *Expert Opin Investig Drugs,* 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or anti-obesity agents as described above.

The present invention further relates to pharmaceutical compositions as described above for use as a medicament.

The present invention further relates to use of pharmaceutical compositions or combinations as described above for the preparation of a medicament for the treatment of conditions mediated by PTPase activity, in particular, PTP-1B and TC PTP activity. Such conditions include insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system. Such conditions also include insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

Thus, the present invention also relates to a compound of formula (I) for use as a medicament, to the use of a compound of formula (I) for the preparation of a pharmaceutical composition for treatment of conditions mediated by PTPase activity, in particular, PTP-1B and TC PTP activity, and to a pharmaceutical composition for use in conditions mediated by PTPase activity, in particular, PTP-1B and TC PTP activity, comprising a compound of formula (I), or a pharmaceutically acceptable salt thereof, in association with a pharmaceutically acceptable diluent or carrier therefore.

The present invention further provides a method for the treatment of conditions mediated by PTPase activity, in particular, PTP-1B and TC PTP activity, which method comprises administering a therapeutically effective amount of a compound of the present invention.

A unit dosage for a mammal of about 50 to 70 kg may contain between about 1 mg and 1000 mg, advantageously between about 5 mg to 500 mg of the active ingredient. The therapeutically effective dosage of a compound of formula I is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound of formula (I), or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula (I), or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of PTPase activity, in particular, PTP-1B and TC PTP activity.

Preferably, the condition associated with PTPase activity, in particular, PTP-1B and TC PTP activity, is selected from insulin resistance, glucose intolerance, type 2 diabetes, renal insufficiency (diabetic and non-diabetic), diabetic nephropathy, glomerulonephritis, glomerular sclerosis, proteinuria of primary renal disease, diabetic retinopathy, obesity, all types of heart failures including acute and chronic congestive heart failure, left ventricular dysfunction and hypertrophic cardiomyopathy, diabetic cardiac myopathy, supraventricular and ventricular arrhythmias, atrial fibrillation and atrial flutter, hypertension, primary and secondary pulmonary hypertension, renal vascular hypertension, dyslipidemia, atherosclerosis, ischemic diseases of the large and small blood vessels, angina pectoris (whether unstable or stable), myocardial infarction and its sequelae, ischemia/reperfusion injury, detrimental vascular remodeling including vascular restenosis, management of other vascular disorders including migraine, peripheral vascular disease and Raynaud's disease, irritable bowel syndrome, pancreatitis, cancer (such as prostate or breast cancer), osteoporosis, multiple sclerosis, stroke, spinal cord injury, neurodegenerative diseases such as Alzheimer's, Parkinson's and polyglutamine disorders such as Huntington's and spinocerebellar ataxia, infectious diseases, and diseases involving inflammation and the immune system and diseases involving muscle degeneration.

Preferably, the condition associated with PTPase activity, in particular, PTP-1B and TC PTP activity, is selected from insulin resistance, glucose intolerance, obesity, diabetes mellitus, hypertension and ischemic diseases of the large and small blood vessels, conditions accompanying type 2 diabetes including dyslipidemia, e.g., hyperlipidemia and hypertriglyceridemia, atherosclerosis, vascular restenosis, irritable bowel syndrome, pancreatitis, adipose cell tumors and carcinomas such as liposarcoma, dyslipidemia, and other disorders where insulin resistance is indicated. In addition, the compounds of the present invention may be employed to treat cancer (such as prostate or breast cancer), osteoporosis, neurodegenerative and infectious diseases, and diseases involving inflammation and the immune system.

Finally, the present invention provides a method or use which comprises administering a compound of formula (I) in combination with a therapeutically effective amount of an anti-diabetic agent, a hypolipidemic agent, an anti-obesity agent or an anti-hypertensive agent.

Ultimately, the present invention provides a method or use which comprises administering a compound of formula (I) in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests, using advantageously mammals, e.g., mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-3}$ molar and $10^{-11}$ molar concentrations or between about $10^{-3}$ molar and $10^{-10}$ molar concentrations. A therapeutically effective amount in vivo may range depending on the route of administration, between about 0.1 and 500 mg/kg or between about 1 and 500 mg/kg, preferably between about 5 and 100 mg/kg.

The activity of a compound according to the invention may be assessed by the following methods or by following methods well described in the art (e.g. Peters G. et al. *J. Biol. Chem.*, 2000, 275, 18201-09).

For example, the PTP-1B inhibitory activity in vitro may be determined as follows:

Assessment of human PTP-1B (hPTP-1B) activity in the presence of various agents is determined by measuring the amount of inorganic phosphate released from a phosphopeptide substrate using a 96-well microtiter plate format. The assay (100 µL) is performed in an assay buffer comprised of 50 mM TRIS (pH 7.5), 50 mM NaCl, 3 mM DTT at ambient temperature. The assay is typically performed in the presence of 0.4% dimethyl sulfoxide (DMSO). However, concentrations as high as 10% are used with certain poorly soluble compounds. A typical reaction is initiated by the addition of 0.4 pmoles of hPTP-1B (amino acids 1-411) to wells containing assay buffer, 3 nmoles of the synthetic phosphopeptide substrate (GNGDpYMPMSPKS), and the test compound. After 10 min, 180 µL malachite green reagent (0.88 mM malachite green, 8.2 mM ammonium molybdate, aqueous 1 N HCl, and 0.01% Triton X-100) is added to terminate the reaction. Inorganic phosphate, a product of the enzyme reaction, is quantitated after 15 min as the green color resulting from complexing with the Malichite reagent and is determined as an $A_{620}$ using a Molecular Devices (Sunnyvale, Calif.) SpectraMAX Plus spectrophotometer. Test compounds are solubilized in 100% DMSO (Sigma, D-8779) and diluted in DMSO. Activity is defined as the net change in absorbance resulting from the activity of the uninhibited hPTP-1B$_{[1-411]}$ minus that of a tube with acid-inactivated hPTP-1B$_{[1-411]}$.

The hPTP-1B$_{[1-411]}$ is cloned by PCR from a human hippocampal cDNA library (Clonetech) and inserted into a pET 19-b vector (Novagen) at the Ncol restriction site. *E. coli* strain BL21 (DE3) is transformed with this clone and stored as a stock culture in 20% glycerol at −80° C. For enzyme production, a stock culture is inoculated into Lb/Amp and grown at 37° C. Expression of PTP-1B is initiated by induction with 1 mM IPTG after the culture had reached an $OD_{600}$=0.6. After 4 h, the bacterial pellet is collected by centrifugation. Cells are resuspended in 70 mL lysis buffer (50 mM Tris, 100 mM NaCl, 5 mM DTT, 0.1% Triton X-100, pH7.6), incubated on ice for 30 min then sonicated (4×10 sec bursts at full power). The lysate is centrifuged at 100,000×g for 60 min and the supernatant is buffer exchanged and purified on a cation exchange POROS 20SP column followed by an anion exchange Source 30Q (Pharmacia) column, using linear NaCl gradient elutions. Enzyme is pooled, adjusted to 1 mg/mL and frozen at −80° C.

Alternatively, the assessment of human PTP-1B activity in the presence of various agents may be determined by measuring the hydrolysis products of known competing substrates. For example, cleavage of substrate para-nitrophenylphosphate (pNPP) results in the release of the yellow-colored para-nitrophenol (pNP) which can be monitored in real time using a spectrophotometer. Likewise, the hydrolysis of the fluorogenic substrate 6,8-difluoro-4-methylumbelliferyl phosphate ammonium salt (DiFMUP) results in the release of the fluorescent DiFMU which can be readily followed in a continuous mode with a fluorescence reader (Anal. Biochem. 273, 41, 1999; Anal. Biochem. 338, 32, 2005):

pNPP Assay

Compounds were incubated with 1 nM recombinant human PTP-1B$_{[1-298]}$ or PTP-1B$_{[1-322]}$ in buffer (50 mM Hepes, pH 7.0, 50 mM KCl, 1 mM EDTA, 3 mM DTT, 0.05% NP-40 for 5 min at room temperature. The reaction is initiated by the addition of pNPP (2 mM final concentration) and run for 120 min at room temperature. Reactions are quenched with 5 N NaOH. Absorbance at 405 nm is measured using any standard 384 well plate reader.

DiFMUP Assay

Compounds are incubated with 1 nM recombinant human PTP-1B$_{[1-298]}$ or PTP-1B$_{[1-322]}$ in buffer (50 mM Hepes, pH 7.0, 50 mM KCl, 1 mM EDTA, 3 mM DTT, 0.05% NP-40 (or 0.001% BSA) for 5 min at room temperature. The reaction is initiated by the addition of DiFMUP (6 µM final concentration) and run kinetically on fluorescence plate reader at 355 nm excitation and 460 nm emission wavelengths. Reaction rates over 15 min are used to calculate inhibition.

PTP-1B$_{[1-298]}$ is expressed in *E. coli* BL21 (DE3) containing plasmids constructed using pET19b vectors (Novagen). The bacteria is grown in minimal media using an "On Demand" Fed-batch strategy. Typically, a 5.5 liter fermentation is initiated in Fed-batch mode and grown overnight unattended at 37° C. Optical densities varied between 20-240$D_{600}$ and the cultures are induced at 30° C. with IPTG to a final concentration of 0.5 mM. The bacterial cells are harvested 8 hours later and yield 200-350 gm (wet weight). The cells are frozen as pellets and stored at −80° C. until use. All steps are performed at 4° C. unless noted. Cells (~15 g) are thawed briefly at 37° C. and resuspended in 50 mL of lysis buffer containing 50 mM Tris-HCl, 150 mM NaCl, 5 mM DTT, pH 8.0 containing one tablet of Complete (EDTA-free) protease cocktail (Boehringer Mannheim), 100 µM PMSF and 100 µg/mL DNase I. The cells are lysed by sonication (4×10 second burst, full power) using a Virsonic 60 (Virtus). The pellet is collected at 35,000×g, resuspended in 25 mL of lysis buffer using a Polytron and collected as before. The two supernatants are combined and centrifuged for 30 min at 100,000×g. The soluble lysate could be stored at this stage at −80° C. or used for further purification. Diafiltration using a 10 kD MWCO membrane is used to buffer exchange the protein and reduce the NaCl concentration prior to cation exchange chromatography. Diafiltration buffer contained 50 mM MES, 75 mM NaCl, 5 mM DTT, pH 6.5. Soluble supernatant is then loaded onto a POROS 20 SP (1×10 cm) column equilibrated with cation exchange buffer (50 mM MES and 75 mM NaCl, pH 6.5) at a rate of 20 mL/min. An analytical column (4.6×100 mm) is run in a similar fashion except the flow rate was reduced to 10 mL/min. Protein is eluted from the column using a linear salt gradient (75-500 mM NaCl in 25 CV). Fractions containing PTP-1B$_{[1-298]}$ are identified and pooled according to SDS-PAGE analyses. Final purification is performed using Sephacryl S-100 HR (Pharmacia). The column (2.6×35 cm) is equilibrated with 50 mM HEPES, 100 mM NaCl, 3 mM DTT, pH 7.5 and run at a flow rate of 2 mL/min. The final protein is pooled and concentrated to ~5 mg/mL using an Ultrafree-15 concentrator (Millipore) with a MWCO 10,000. The concentrated protein is stored at −80° C. until use.

Competitive binding to the active site of the enzyme may be determined as follows:

Ligand binding is detected by acquiring $^1$H-$^{15}$N HSQC spectra on 250 μL of 0.15 mM PTP-1B$_{[1-298]}$ in the presence and absence of added compound (1-2 mM). The binding is determined by the observation of $^{15}$N- or $^1$H-amide chemical shift changes in two dimensional HSQC spectra upon the addition of a compound to $^{15}$N-label protein. Because of the $^{15}$N spectral editing, no signal from the ligand is observed, only protein signals. Thus, binding can be detected at high compound concentrations. Compounds which caused a pattern of chemical shift changes similar to the changes seen with known active site binders are considered positive.

All proteins are expressed in E. coli BL21 (DE3) containing plasmids constructed using pET19b vectors (Novagen). Uniformly $^{15}$N-labeled PTP-1B$_{1-298}$ is produced by growth of bacteria on minimal media containing $^{15}$N-labeled ammonium chloride. All purification steps are performed at 4° C. Cells (~15 g) are thawed briefly at 37° C. and resuspended in 50 mL of lysis buffer containing 50 mM Tris-HCl, 150 mM NaCl, 5 mM DTT, pH 8.0 containing one tablet of Complete (EDTA-free) protease cocktail (Boehringer Mannheim), 100 μM PMSF and 100 μg/mL DNase I. The cells are lysed by sonication. The pellet is collected at 35,000×g, resuspended in 25 mL of lysis buffer using a Polytron and collected as before. The two supernatants are combined and centrifuged for 30 min at 100,000×g. Diafiltration using a 10 kD MWCO membrane is used to buffer exchange the protein and reduce the NaCl concentration prior to cation exchange chromatography. Diafiltration buffer contained 50 mM MES, 75 mM NaCl, 5 mM DTT, pH 6.5. Soluble supernatant is then loaded onto a POROS 20 SP (1×10 cm) column equilibrated with cation exchange buffer (50 mM MES and 75 mM NaCl, pH 6.5) at a rate of 20 mL/min. Protein is eluted from the column using a linear salt gradient (75-500 mM NaCl in 25 CV). Fractions containing PTP-1B's are identified and pooled according to SDS-PAGE analyses. PTP-1B$_{1-298}$ is further purified by anion exchange chromatography using a POROS 20 HQ column (1×10 cm). The pool from cation exchange chromatography is concentrated and buffer exchanged in 50 mM Tris-HCl, pH 7.5 containing 75 mM NaCl and 5 mM DTT. Protein is loaded onto column at 20 mL/min and eluted using a linear NaCl gradient (75-500 mM in 25 CV). Final purification is performed using Sephacryl S-100 HR (Pharmacia) (50 mM HEPES, 100 mM NaCl, 3 mM DTT, pH 7.5). The NMR samples are composed of uniformly $^{15}$N-labeled PTP-1B$_{1-298}$ (0.15 mM) and inhibitor (1-2 mM) in a 10% D$_2$O/90% H$_2$O Bis-Tris-d$_{19}$ buffer (50 mM, pH=6.5) solution containing NaCl (50 mM), DL-1,4-Dithiothreitol-d$_{10}$ (5 mM) and Sodium azide (0.02%).

The $^1$H-$^{15}$N HSQC NMR spectra are recorded at 20° C., on Bruker DRX500 or DMX600 NMR spectrometers. In all NMR experiments, pulsed field gradients are applied to afford the suppression of solvent signal. Quadrature detection in the indirectly detected dimensions is accomplished by using the States-TPPI method. The data are processed using Bruker software and analyzed using NMRCompass software (MSI) on Silicon Graphics computers.

The glucose and insulin lowering activity in vivo may be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day 1 tail blood samples are taken at 8:00 am and plasma glucose levels are determined. The animals are randomly assigned to the control and compound groups. The means of plasma glucose values of the groups are matched. Animals are then orally dosed with vehicle (0.5% carboxymethyl-cellulose with 0.2% Tween-80) or compounds (at 30 mg/kg) in vehicle. The mice are dosed daily for a total of 3 days. On day 4 basal blood samples are taken. The plasma samples are analyzed for glucose concentrations using a YSI2700 Dual Channel Biochemistry Analyzer (Yellow Springs Instrument Co., Yellow Springs, Ohio) and insulin concentrations using an ELISA assay.

The following Examples are intended to illustrate the invention and are not to be construed as being limitations thereon. Temperatures are given in degrees Centigrade (° C.). If not mentioned otherwise, all evaporations are performed under reduced pressure, preferably between about 15 and 100 mmHg (=20-133 mbar). The structure of final products, intermediates and starting materials is confirmed by standard analytical methods, e.g. microanalysis, melting point (mp) and spectroscopic characteristics (e.g. MS, IR, NMR). In general, abbreviations used are those conventional in the art.

Method A: 4.6 mm×5 cm C-8 reverse phase column, 3 μm particle size running a gradient of 10-90% MeCN/water (5 mM ammonium bicarbonate) over a period of 2 min at a flow rate of 4 mL/min at 50° C. (3 μL injection). DAD-UV detection, 220-600 nm.

Method B: 4.6 mm×5 cm C18 reverse phase, 3.5 μm particle size running a gradient of 5-95% MeCN/water (5 mM ammonium formate) over a period of 3 min followed by 2 min of isocratic elution at 95% MeCN/water (5 mM ammonium formate) at a flow rate of 1 mL/min at room temperature. DAD-UV detection, 190-400 nm.

EXAMPLE 1

5-(3,6-Dihydroxynaphthalen-2-yl)-1,1-dioxo-1,2,5-thiadiazolidin-3-one potassium salt

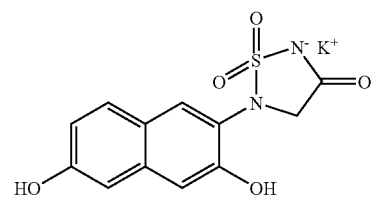

A. 3-Bromonaphthalene-2,7-diol

To a suspension of 1,3-dibromonaphthalene-2,7-diol (48.76 g, 153.34 mmol) (Helv. Chim. Acta, 78, pp. 1037-1066, 1995) in AcOH/HCl is added tin (17.48 g, 147.21 mmol) in portions. The mixture is stirred vigorously at room temperature for 1 h. The reaction forms a paste and is stirred for an additional 4 h, at which point it becomes mobile again. Stirring is continued overnight. The mixture is poured into water (1 L) and extracted with EtOAc. The organic layer is dried over MgSO$_4$, filtered and concentrated to afford a sticky beige solid. The solid is triturated with DCM and filtered to afford 3-bromonaphthalene-2,7-diol as a fluffy beige solid.

B. 3,6-Bis-benzyloxy-2-bromonaphthalene

3-Bromonaphthalene-2,7-diol (1.40 g, 5.88 mmol) is dissolved in 20 mL of DMF. Potassium carbonate (2.44 g, 17.6 mmol) is added and the mixture is heated to 60° C. Benzyl bromide (2.10 mL, 17.64 mmol) is added and heating is continued for 5 h, after which time the reaction is poured into water and extracted with MTBE. The combined organics are dried and evaporated to afford 3,6-bis-benzyloxy-2-bromonaphthalene as a brown solid, which is of sufficient purity to take on to the next step.

C. Benzhydrylidene-(3,6-bis-benzyloxynaphthalen-2-yl)-amine 3,6-Bis-benzyloxy-2-bromo-naphthalene (2.47 g, 5.89 mmol), benzophenone imine (1.19 mL, 7.07), $Pd_2(dba)_3$ (0.013 g, 0.015 mmol), BINAP (0.027 g, 0.044 mmol) and sodium methoxide (0.445 g, 8.25 mmol) are added to a dry flask over nitrogen. Toluene (10 mL) is added at ambient temperature and the reaction heated to 110° C. for 15 h. The reaction mixture is poured into water and extracted with ethyl acetate. The organic layer is dried and evaporated to afford a brown oil, which is chromatographed over silica, eluting with a gradient of 100:1 to 20:1 hexanes/MTBE, to afford benzhydrylidene-(3,6-bis-benzyloxynaphthalen-2-yl)-amine.

D. 3,6-Bis-benzyloxynaphthalen-2-ylamine

Benzhydrylidene-(3,6-bis-benzyloxynaphthalen-2-yl)-amine (0.628 g, 1.208 mmol) is dissolved in 15 mL of THF. A solution of 1 N HCl (15 mL) is added and stirred for 30 min. The crude reaction mixture is basified to pH 14 with 1 N NaOH and extracted with EtOAc. The combined organic layers are dried and evaporated to afford an orange oil. The oil is purified on silica, eluting with 9:1 hexanes/EtOAc and then 1:1 hexanes/EtOAc, to afford 3,6-bis-benzyloxynaphthalen-2-ylamine.

E. (3,6-Bis-benzyloxynaphthalen-2-ylamino)-acetic acid ethyl ester 3,6-Bis-benzyloxynaphthalen-2-ylamine (0.332 g, 0.934 mmol) is dissolved in DMF (5 mL). Ethyl bromoacetate (0.114 mL, 1.03 mmol) and potassium carbonate (0.194 g, 1.40 mmol) are added. The reaction is heated to 60° C. for 3 h and then poured into 1 N HCl and extracted with EtOAc. The combined organic layers are washed with brine, dried and evaporated to a red foam, which is purified over silica, eluting with 8:1 hexanes/MTBE, to afford (3,6-bis-benzyloxynaphthalen-2-ylamino)-acetic acid ethyl ester as a yellow solid.

F. (3,6-Bis-benzyloxynaphthalen-2-yl)-N-(t-butoxycarbonylsulfamoyl)-acetic acid ethyl ester Chlorosulfonyl isocyanate (0.084 mL, 0.9681 mmol) is dissolved in DCM (7.5 mL) and cooled to 0° C. t-Butanol (0.51 mL, 0.9681 mmol) is added and the mixture stirred for 50 min. (3,6-Bis-benzyloxynaphthalen-2-ylamino)-acetic acid ethyl ester (0.285 g, 0.6454 mmol) and triethylamine (0.360 mL, 2.58 mmol) are added. The mixture is allowed to warm to ambient temperature over 2 h. The reaction mixture is evaporated and then partitioned between 1 N HCl and EtOAc. The combined organic layers are washed with sat. sodium bicarbonate, dried and evaporated to afford an off white foam. The foam is purified via chromatography on silica, eluting with a gradient of 5:1 to 1:1 hexanes/EtOAc, to afford (3,6-bis-benzyloxynaphthalen-2-yl)-N-(t-butoxycarbonylsulfamoyl)-acetic acid ethyl ester.

G. (3,6-Bis-benzyloxynaphthalen-2-yl)-N-sulfamoyl-acetic acid ethyl ester

To a solution of (3,6-bis-benzyloxynaphthalen-2-yl)-N-(t-butoxycarbonylsulfamoyl)-acetic acid ethyl ester (0.156 g, 0.251 mmol) in $CH_2Cl_2$ (7 mL), is added TFA (2 mL). The mixture is stirred at room temperature for 30 min. The mixture is concentrated to remove $CH_2Cl_2$ and the TFA is azeotroped with toluene (4×). The residue is dried under high vacuum for 3 h to afford (3,6-bis-benzyloxynaphthalen-2-yl)-N-sulfamoyl-acetic acid ethyl ester.

H. 5-(3,6-Bis-benzyloxynaphthalen-2-yl)-1,1-dioxo-1,2,5-thiadiazolidin-3-one potassium salt To a solution of (3,6-bis-benzyloxynaphthalen-2-yl)-N-sulfamoyl-acetic acid ethyl ester (0.131 g, 0.252 mmol) in THF (3 mL) is added potassium tert-butoxide (0.252 mL, 0.252 mmol). The reaction mixture is stirred at room temperature overnight. The reaction is judged complete by LC/MS. The mixture is concentrated and dried under high vacuum to afford 5-(3,6-bis-benzyloxynaphthalen-2-yl)-1,1-dioxo-1,2,5-thiadiazolidin-3-one potassium salt. The crude material is carried over to the next step.

I. 5-(3,6-Dihydroxynaphthalen-2-yl)-1,1-dioxo-1,2,5-thiadiazolidin-3-one potassium salt To a solution of 5-(3,6-bis-benzyloxynaphthalen-2-yl)-1,1-dioxo-1,2,5-thiadiazolidin-3-one potassium salt (0.129 g, 0.252 mmol) in $H_2O$ (5 mL), flushed with $N_2$, is added 10% Pd/C (0.10 g). The mixture is flushed with $N_2$ again and then placed under an atmosphere of $H_2$. The mixture is stirred vigorously for 1.5 h before being judged complete by LC/MS. The reaction mixture is filtered over Celite. The filtrate is washed with EtOH and the aqueous layer is lyophilized overnight. The residual solid is redissolved in $H_2O$ and refiltered over Celite. The green filtrate is lyophilized again overnight. The residue is purified via prep HPLC. The desired fractions are concentrated and dissolved in a minimum amount of EtOH. To this solution is added a 0.5M solution of $KHCO_3$ followed by the addition of $H_2O$. The reaction mixture is stirred for 2 min and lyophilized overnight to afford 5-(3,6-dihydroxynaphthalen-2-yl)-1,1-dioxo-1,2,5-thiadiazolidin-3-one potassium salt: $^1$H NMR (DMSO-$d_6$) δ9.93 (s, 1H), 9.63 (s, 1H), 7.79 (s, 1H), 7.61 (d, J=8 Hz, 1H), 7.01 (s, 1H), 6.86 (m, 2H), 4.43 (s, 2H).

EXAMPLE 2

5-(3,7-Dihydroxynaphthalen-2-yl)-1,1-dioxo-1,2,5-thiadiazolidin-3-one potassium salt

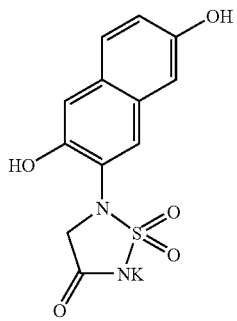

A. 3,7-Bis-benzyloxynaphthalene-2-carboxylic acid benzyl ester

A mixture of 3,7-dihydroxynaphthalene-2-carboxylic acid (2.04 g, 10 mmol), benzyl bromide (5.98 g, 35 mmol) and potassium carbonate (6.9 g, 50 mmol) in 20 mL of DMF is stirred at 60° C. for 18 h. The mixture is cooled to room temperature, poured into water and extracted into EtOAc. The organic phase is washed with water (3×) and saturated NaCl (1×). The organic phase is dried over sodium sulfate and the solvent is removed under reduced pressure. The residual solid is dissolved in a minimum of DCM and filtered through a pad of silica gel using DCM to elute the product. The solvent is removed under reduced pressure to afford 3,7-bis-benzyloxynaphthalene-2-carboxylic acid benzyl ester as a tan solid: mp=99-102° C.

B. 3,7-Bis-benzyloxynaphthalene-2-carboxylic acid

To a suspension of 3,7-bis-benzyloxynaphthalene-2-carboxylic acid benzyl ester (4.0 g, 8.4 mmol) in EtOH (75 mL), is added 10 mL of 1.0N NaOH (1.2 eq.) and the mixture is stirred at 70° C. for 18 h. The solvent is removed under reduced pressure and the residual solid is dissolved in 250 mL of water. The solution is washed with EtOH and the aqueous phase is acidified with 2N HCl. The resulting precipitate is filtered, washed with water and dried to afford 3,7-bis-benzyloxynaphthalene-2-carboxylic acid as a pale-yellow solid: mp=163-165° C.; (M–H)⁻=383.

C. (3,7-Bis-benzyloxynaphthalene-2-yl)-carbamic acid tert-butyl ester

To a suspension of 3,7-bis-benzyloxynaphthalene-2-carboxylic acid (0.768 g, 2 mmol) in anhydrous t-BuOH (8 mL) and anhydrous toluene (8 mL) is added triethylamine (0.303 g, 3 mmol). To the resulting solution is added DPPA (0.715 g, 2.6 mmol) and the mixture is stirred at room temperature for 5 min, then stirred at 100° C. for 18 h. The mixture is allowed to cool to room temperature and then poured into water. The mixture is extracted into EtOAc and the organic phase is washed with saturated NaCl. The solvent is removed under reduced pressure and the resulting residue is purified by flash chromatography, eluting with DCM to afford (3,7-bis-benzyloxynaphthalene-2-yl)-carbamic acid tert-butyl ester as a white solid: mp=179-182° C.

D. 3,7-Bis-benzyloxynaphthalen-2-ylamine

The deprotection of the amine is performed analogously to Example 1, step G, to afford 3,7-bis-benzyloxynaphthalen-2-ylamine.

E. 5-(3,7-Dihydroxynaphthalen-2-yl)-1,1-dioxo-1,2,5-thiadiazolidin-3-one potassium salt 5-(3,7-Dihydroxynaphthalen-2-yl)-1,1-dioxo-1,2,5-thiadiazolidin-3-one potassium salt is prepared according to the general procedures outlined in Example 1, steps E-I, to afford a brownish solid: mp=220-230° C.; (M–H)⁻=293.

EXAMPLE 3

5-(7-Bromo-3-hydroxynaphthalen-2-yl)-1,1-dioxo-1,2,5-thiadiazolidin-3-one

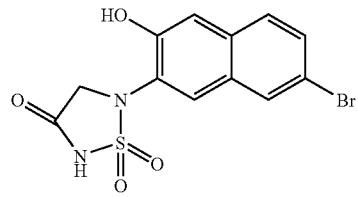

A. (3-Benzyloxy-7-bromonaphthalen-2-yl)-carbamic acid tert-butyl ester (3-Benzyloxy-7-bromonaphthalen-2-yl)-carbamic acid tert-butyl ester is prepared analogously to Example 2, steps A-C.

B. [(3-Benzyloxy-7-bromonaphthalen-2-yl)-tert-butoxycarbony-amino]-acetic acid methyl ester To a solution of (3-benzyloxy-7-bromonaphthalen-2-yl)-carbamic acid tert-butyl ester (38.65 g, 90.2 mmol) in DMF (300 mL) at 0° C. is added NaH (3.79 g, 99.3 mmol). To the solution is added methyl bromoacetate (10.3 mL, 108.2 mmol). The mixture is stirred for 10 min and then quenched with 1 N HCl. The solution is extracted with EtOAc and washed with 1 N HCl (3×) and sat. NaCl. The organic layer is dried over Na₂SO₄, filtered and concentrated. The residue is recrystallized from EtOAc to afford [(3-benzyloxy-7-bromonaphthalen-2-yl)-tert-butoxycarbony-amino]-acetic acid methyl ester.

C. (3-Benzyloxy-7-bromonaphthalen-2-ylamino)-acetic acid methyl ester (3-Benzyloxy-7-bromonaphthalen-2-ylamino)-acetic acid methyl ester is prepared analogously to Example 1, step G.

D. 5-(3-Benzyloxy-7-bromonaphthalen-2-yl)-1,1-dioxo-1,2,5-thiadiazolidin-3-one 5-(3-Benzyloxy-7-bromonaphthalen-2-yl)-1,1-dioxo-1,2,5-thiadiazolidin-3-one is prepared analogously to Example 1, steps F-H.

E. 5-(7-Bromo-3-hydroxynaphthalen-2-yl)-1,1-dioxo-1,2,5-thiadiazolidin-3-one A solution of 5-(3-benzyloxy-7-bromonaphthalen-2-yl)-1,1-dioxo-1,2,5-thiadiazolidin-3-one (1.22 g, 2.75 mmol) in dichloroethane (300 mL) is cooled to 0° C. To the solution is added BBr$_3$ (1M in CH$_2$Cl$_2$, 3 mL) and this is stirred for 10 min. The solution is portioned between EtOAc and 1 N HCl. The organic layer is washed with saturated NaCl, dried over Na$_2$SO$_4$, filtered and concentrated. The crude material is purified via HPLC to afford 7-bromo-3-hydroxynaphthalen-2-yl)-1,1-dioxo-1,2,5-thiadiazolidin-3-one: $^1$H NMR (DMSO-d$_6$) δ 10.39 (br s, 1H), 8.05 (d, J=2 Hz, 1H), 7.97 (s, 1H), 7.68 (d, J=8.84 Hz, 1H), 7.49 (dd, J=8.59, 2.02 Hz, 1H), 7.26 (s, 1H), 4.49 (s, 2H). Retention time=0.92 min (Method A), (M−H)$^−$=357.

EXAMPLE 4

5-(7-Ethyl-3-hydroxynaphthalen-2-yl)-1,1-dioxo-1,2,5-thiadiazolidin-3-one

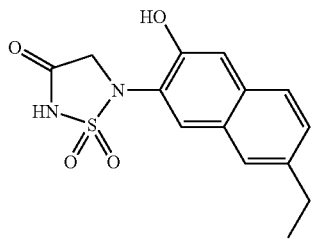

A. 5-(3-Benzyloxy-7-vinylnaphthalen-2-yl)-1,1-dioxo-1,2,5-thiadiazolidin-3-one To a microwave vial containing 5-(3-benzyloxy-7-bromonaphthalen-2-yl)-1,1-dioxo-1,2,5-thiadiazolidin-3-one (Example 3, step D) (0.21 g, 0.46 mmol), vinylboronic acid dibutyl ester (0.20 mL, 0.92 mmol), and PS-tetrakistriphenylphosphine palladium (0.36 mg, 0.046 mmol) in DME (4 mL) is added Na$_2$CO$_3$ (2.0M, 0.92 mL, 1.83 mmol). This is stirred in the microwave at 110° C. for 10 min, at which time LC/MS reveals complete conversion to the desired product. The resin-bound palladium is removed by filtration and the filtrate is concentrated in vacuo, and purified by reverse-phase Biotage MPLC to afford 5-(3-benzyloxy-7-vinylnaphthalen-2-yl)-1,1-dioxo-1,2,5-thiadiazolidin-3-one as a light brown oil.

B. 5-(7-Ethyl-3-hydroxynaphthalen-2-yl)-1,1-dioxo-1,2,5-thiadiazolidin-3-one 5-(7-Ethyl-3-hydroxynaphthalen-2-yl)-1,1-dioxo-1,2,5-thiadiazolidin-3-one is prepared analogously to Example 1, step 1, with the exception that Pd(OH)$_2$ is used in place of Pd/C: $^1$H NMR (MeOD) δ 7.78 (s, 1H), 7.48 (d, J=8.59 Hz, 1H), 7.44 (s, 1H), 7.21 (dd, J=8.46, 1.64 Hz, 1H), 7.1 (s, 1H), 4.51 (s, 2H), 2.67 (q, J=7.78 Hz, 2H), 1.19 (t, J=7.58 Hz, 3H). (M−H)$^−$=305.

EXAMPLE 5

The following compounds are prepared using appropriate starting materials and general procedures described in Example 4, using either Pd(PPh$_3$)$_4$ or resin bound PS-tetrakistriphenylphosphine palladium. For Example 5-12, CuCN is used in place of a boronic ester. For Example 5-24 and 5-25, triethylamine is used to replace 2M NaCO$_3$. For Example 5-26, 10% Pd/C is used to replace Pd(OH)$_2$.

| Example | Chemical Name | MS (m/z) | Retention time (min) Method |
|---|---|---|---|
| 5-1 | 5-{3-Hydroxy-7-[2-(4-methoxyphenyl)-ethyl]-naphthalen-2-yl}-1,1-dioxo-1,2,5-thiadiazolidin-3-one | (M − H)$^−$ = 411 | 1.28 A |
| 5-2 | 5-{3-Hydroxy-7-[2-(4-trifluoromethylphenyl)-ethyl]-naphthalen-2-yl}-1,1-dioxo-1,2,5-thiadiazolidin-3-one | (M − H)$^−$ = 449 | 1.44 A |
| 5-3 | 5-{3-Hydroxy-7-[2-(3-methoxyphenyl)-ethyl]-naphthalen-2-yl}-1,1-dioxo-1,2,5-thiadiazolidin-3-one | (M − H)$^−$ = 449 | 1.28 A |
| 5-4 | 5-[3-Hydroxy-7-(4-methylpentyl)-naphthalen-2-yl]-1,1-dioxo-1,2,5-thiadiazolidin-3-one | (M − H)$^−$ = 361 | 1.55 A |
| 5-5 | {3-[6-Hydroxy-7-(1,1,4-trioxo-1,2,5-thiadiazolidin-2-yl)naphthalen-2-yl]-phenyl}-acetic acid | (M − H)$^−$ = 411 | 0.87 A |
| 5-6 | 5-(3-Hydroxy-7-phenylnaphthalen-2-yl)-1,1-dioxo-1,2,5-thiadiazolidin-3-one | (M − H)$^−$ = 353 | 1.37 A |
| 5-7 | 3-[6-Hydroxy-7-(1,1,4-trioxo-1,2,5-thiadiazolidin-2-yl)-naphthalen-2-yl]-benzoic acid | (M − H)$^−$ = 397 | 0.85 A |
| 5-8 | 5-[3-Hydroxy-7-(3-trifluoromethoxyphenyl)-naphthalen-2-yl]-1,1-dioxo-1,2,5-thiadiazolidin-3-one | (M − H)$^−$ = 437 | |
| 5-9 | {3-[6-Hydroxy-7-(1,1,4-trioxo-1,2,5-thiadiazolidin-2-yl)-naphthalen-2-yl]-phenyl}acetonitrile | (M − H)$^−$ = 392 | 1.08 A |
| 5-10 | 5-[3-Hydroxy-7-(3-hydroxymethylphenyl)-naphthalen-2-yl]-1,1-dioxo-1,2,5-thiadiazolidin-3-one | (M − H)$^−$ = 383 | 0.93 A |

-continued

| Example | Chemical Name | MS (m/z) | Retention time (min) Method |
|---|---|---|---|
| 5-11 | 3-{3-[6-Hydroxy-7-(1,1,4-trioxo-thiadiazolidin-2-yl)-naphthalen-2yl]-phenyl}-propionic acid | (M − H)⁻ = 425 | 0.92 A |
| 5-12 | 6-Hydroxy-7-(1,1,4-trioxo-1,2,5-thiadiazolidin-2-yl)-naphthalene-2-carbonitrile | (M − H)⁻ = 302 | |
| 5-13 | 3-[6-Hydroxy-7-(1,1,4-trioxo-1,2,5-thiadiazolidin-2-yl)-naphthalen-2-yl]-benzonitrile | (M − H)⁻ = 378 | |
| 5-14 | 5-[7-(3,3-Dimethylbutyl)-3-hydroxynaphthalen-2-yl]-1,1-dioxo-1,2,5-thiadiazolidin-3-one | (M − H)⁻ = 361 | 1.36 A |
| 5-15 | 5-[3-Hydroxy-7-(3-trifluoromethylphenyl)-naphthalen-2-yl]-1,1-dioxo-1,2,5-thiadiazolidin-3-one | (M − H)⁻ = 421 | |
| 5-16 | 3-[6-Hydroxy-7-(1,1,4-trioxo-1,2,5-thiadiazolidin-2-yl)-naphthalen-2-yl]-benzoic acid ethyl ester | (M − H)⁻ = 425 | |
| 5-17 | 5-[3-Hydroxy-7-(3-methanesulfonylphenyl)-naphthalen-2-yl]-1,1-dioxo-1,2,5-thiadiazolidin-3-one | (M − H)⁻ = 431 | 1.13 A |
| 5-18 | 3-{3-[6-Hydroxy-7-(1,1,4-trioxo-1,2,5-thiadiazolidin-2-yl)-naphthalen-2-yl]-phenyl}-propionitrile | (M − H)⁻ = 406 | |
| 5-19 | 5-[3-Hydroxy-7-(3-methoxymethylphenyl)-naphthalen-2-yl]-1,1-dioxo-1,2,5-thiadiazolidin-3-one | (M − H)⁻ = 397 | |
| 5-20 | 5-(7-Furan-3-yl-3-hydroxynaphthalen-2-yl)-1,1-dioxo-1,2,5-thiadiazolidin-3-one | (M − H)⁻ = 343 | 1.11 A |
| 5-21 | N-{3-[6-Hydroxy-7-(1,1,4-trioxo-1,2,5-thiadiazolidin-2-yl)-naphthalen-2-yl]-phenyl}-methanesulfonamide | (M − H)⁻ = 446 | 0.93 A |
| 5-22 | 5-[7-(2-Fluorophenyl)-3-hydroxynaphthalen-2-yl]-1,1-dioxo-1,2,5-thiadiazolidin-3-one | (M − H)⁻ = 371 | 1.12 A |
| 5-23 | 5-(3-Hydroxy-7-o-tolylnaphthalen-2-yl)-1,1-dioxo-1,2,5-thiadiazolidin-3-one | (M − H)⁻ = 367 | 1.20 A |
| 5-24 | 5-(3-Hydroxy-7-pentylnaphthalen-2-yl)-1,1-dioxo-1,2,5-thiadiazolidin-3-one | (M − H)⁻ = 347 | 1.37 A |
| 5-25 | 5-(3-Hydroxy-7-propylnaphthalen-2-yl)-1,1-dioxo-1,2,5-thiadiazolidin-3-one | (M − H)⁻ = 319 | 1.19 A |
| 5-26 | 5-[3-Hydroxy-7-(tetrahydrofuran-3-yl)-naphthalen-2-yl]-1,1-dioxo-1,2,5-thiadiazolidin-3-one | (M − H)⁻ = 347 | 0.87 A |
| 5-27 | 5-[3-Hydroxy-7-((E)-propenyl)-naphthalen-2-yl]-1,1-dioxo-[1,2,5]thiadiazolidin-3-one | (M − H)⁻ = 317 | 1.32 A |
| 5-28 | 5-(3-Hydroxy-7-vinyl-naphthalen-2-yl)-1,1-dioxo-[1,2,5]thiadiazolidin-3-one | (M − H)⁻ = 303 | 1.23 A |

EXAMPLE 6

{3-[6-Hydroxy-7-(1,1,4-trioxo-1,2,5-thiadiazolidin-2-yl)-naphthalen-2-yl]-phenyl}-acetic acid ethyl ester

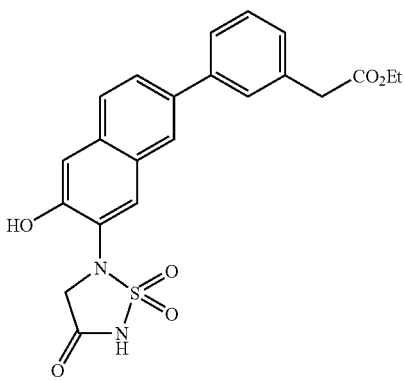

A. {3-[6-Benzyloxy-7-(1,1,4-trioxo-1,2,5-thiadiazolidin-2-yl)-naphthalen-2-yl]-phenyl}-acetic acid The title compound is prepared analogously to Example 4, step A, using [3-(4,4,5,5-tetramethyl-[1,3,2]dioxaborolan-2-yl)-phenyl]-acetic acid.

B. {3-[6-Benzyloxy-7-(1,1,4-trioxo-1,2,5-thiadiazolidin-2-yl)-naphthalen-2-yl]-phenyl}-acetic acid ethyl ester To a solution of {3-[6-benzyloxy-7-(1,1,4-trioxo-1,2,5-thiadiazolidin-2-yl)-naphthalen-2-yl]-phenyl}-acetic acid (600 mg, 1.2 mmol) in EtOH (50 mL) is added TFA (25 mL) and the mixture is heated at 40° C. for 2 h. EtOH and TFA are removed via vacuum and the residue is purified by HPLC to give the title compound.

C. {3-[6-Hydroxy-7-(1,1,4-trioxo-1,2,5-thiadiazolidin-2-yl)-naphthalen-2-yl]-phenyl}-acetic acid ethyl ester The title compound is prepared analogously to Example 4, step B: (M−H)=439.

EXAMPLE 7

3-{3-[6-Hydroxy-7-(1,1,4-trioxo-1,2,5-thiadiazolidin-2-yl)-naphthalen-2-yl]-phenyl}-propionic acid ethyl ester

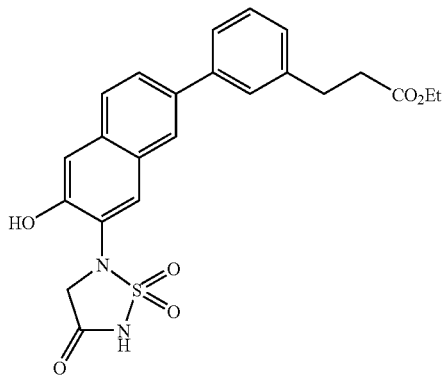

The title compound is prepared analogously to Example 6: (M−H)⁻=453.

EXAMPLE 8

5-[6-Hydroxy-7-(1,1,4-trioxo-1,2,5-thiadiazolidin-2-yl)-naphthalen-2-yl]-pentanoic acid ethyl ester

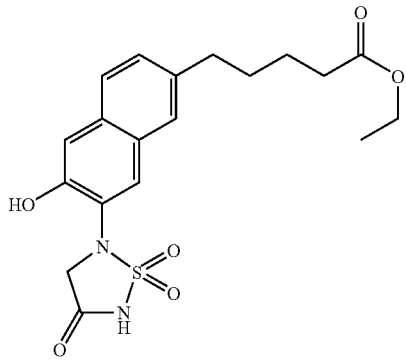

A. 5-[6-Benzylozy-7-(1,1,4-trioxo-1,2,5-thiadiazolidin-2-yl)-naphthalen-2-yl]-pentanoic acid ethyl ester To a stirred solution of ethyl-47-pentenoate (0.25 g, 1.95 mmol) in THF (3 mL) is added 9-BBN (0.5M, 2.50 mL, 1.25 mmol). This is stirred at room temperature for 2 h. The resulting solution is added directly to a microwave vial containing 5-(3-benzyloxy-7-bromo-naphthalen-2-yl)-1,1-dioxo-1,2,5-thiadiazolidin-3-one (Example 3, step D) (0.25 g, 0.56 mmol), PS-tetrakistriphenylphosphine palladium (0.60 g, 0.17 mmol) and $Na_2CO_3$ (2.0M, 1.40 mL, 5.60 mmol). The resulting reaction mixture is diluted with DME (2 mL) and heated in the microwave at 110° C. for 15 min. LC/MS analysis of the reaction reveals complete conversion to the desired product. The resin-bound palladium is removed by filtration and the filtrate is concentrated in vacuo, and purified by reverse-phase Biotage MPLC to afford 5-[6-benzylozy-7-(1,1,4-trioxo-1,2,5-thiadiazolidin-2-yl)-naphthalen-2-yl]-pentanoic acid ethyl ester as a brownish-white solid.

B. 5-[6-Hydroxy-7-(1,1,4-trioxo-1,2,5-thiadiazolidin-2-yl)-naphthalen-2-yl]-pentanoic acid ethyl ester 5-[6-Hydroxy-7-(1,1,4-trioxo-1,2,5-thiadiazolidin-2-yl)-naphthalen-2-yl]-pentanoic acid ethyl ester is prepared analogously to Example 4, step B: ¹H NMR (MeOD) δ 7.93 (s, 1H), 7.56 (d, J=8.59 Hz, 1H), 7.51 (s, 1H), 7.24 (dd, J=8.46, 1.64 Hz, 1H), 7.18 (s, 1H), 4.46 (s, 2H), 4.09 (q, J=7.07 Hz, 2H), 2.73 (t, J=7.07 Hz, 2H), 2.34 (t, J=7.07 Hz, 2H), 1.61 (m, 4H), 1.22 (t, J=7.20 Hz, 3H). Retention time=1.31 min (Method A); (M−H)⁻=405.

EXAMPLE 9

The following examples are prepared using appropriate starting materials and general procedures described in Example 8, steps A-B. For Examples 9-8 and 9-10, an additional hydrolysis step is used as described in Example 11.

| Example | Chemical Name | MS (m/z) | Retention time (min) Method |
|---|---|---|---|
| 9-1 | 4-[6-Hydroxy-7-(1,1,4-trioxo-1,2,5-thiadiazolidin-2-yl)-naphthalen-2-yl]-2,2-dimethyl-butyric acid | (M − H)⁻ = 391 | 2.42 B |
| 9-2 | 5-[3-Hydroxy-7-((S)-4-hydroxypentyl)-naphthalen-2-yl]-1,1-dioxo-1,2,5-thiadiazolidin-3-one | (M − H)⁻ = 363 | 1.05 A |
| 9-3 | 4-[6-Hydroxy-7-(1,1,4-trioxo-1,2,5-thiadiazolidin-2-yl)-naphthalen-2-yl]-2-methylbutyronitrile | (M − H)⁻ = 358 | 0.97 A |
| 9-4 | 5-[6-Hydroxy-7-(1,1,4-trioxo-1,2,5-thiadiazolidin-2-yl)-naphthalen-2-yl]-2-methylpentanoic acid ethyl ester | (M − H)⁻ = 419 | 1.18 A |

-continued

| Example | Chemical Name | MS (m/z) | Retention time (min) Method |
|---|---|---|---|
| 9-5 | 5-[3-Hydroxy-7-(3-methylbutyl)-naphthalen-2-yl]-1,1-dioxo-1,2,5-thiadiazolidin-3-one | (M − H)⁻ = 347 | 1.32 A |
| 9-6 | 4-[6-Hydroxy-7-(1,1,4-trioxo-[1,2,5]thiadiazolidin-2-yl)-naphthalen-2-yl]-butyric acid methyl ester | (M − H)⁻ = 377 | 0.92 A |
| 9-7 | 5-{3-Hydroxy-7-[3-(2,2,2-trifluoro-ethoxy)-propyl]-naphthalen-2-yl}-1,1-dioxo-[1,2,5]thiadiazolidin-3-one | (M − H)⁻ = 417 | 1.25 A |
| 9-8 | 4-[6-Hydroxy-7-(1,1,4-trioxo-[1,2,5]thiadiazolidin-2-yl)-naphthalen-2-yl]-butyric acid | (M − H)⁻ = 363 | 0.72 A |
| 9-9 | 5-[3-Hydroxy-7-(3-phenyl-propyl)-naphthalen-2-yl]-1,1-dioxo-[1,2,5]thiadiazolidin-3-one | (M − H)⁻ = 395 | 1.40 A |
| 9-10 | 3-{3-[6-Hydroxy-7-(1,1,4-trioxo-thiadiazolidin-2-yl)-naphthalen-2yl]-phenyl}-propionic acid | (M − H)⁻ = 349 | 0.52 A |

EXAMPLE 10

5-[6-Hydroxy-7-(1,1,4-trioxo-1,2,5-thiadiazolidin-2-yl)-naphthalen-2-yl]-2,2-dimethylpentanenitrile

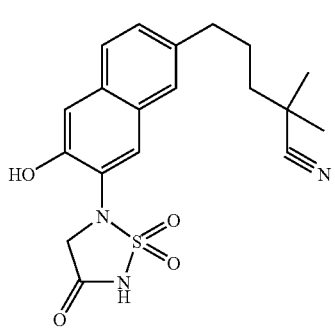

A. 2,2-Dimethylpent-4-enenitrile

To a −78° C. solution of isobutylacetonitril (5 g, 72.4 mmol) in THF (25 mL) is added LHMDS (1M, 94.1 mL, 94.1 mmol) slowly. After it is stirred for 1 h, allyl bromide (7.35 mL, 86.8 mmol) is added slowly. The mixture is stirred for 18 h. Et₂O is added to extract and it is washed with 1 N HCl. The Et₂O layer is concentrated gently to give the title compound.

B. 5-[6-Hydroxy-7-(1,1,4-trioxo-1,2,5-thiadiazolidin-2-yl)-naphthalen-2-yl]-2,2-dimethylpentanenitrile The title compound is prepared analogously to Example 8, steps A-B, from 2,2-dimethylpent-4-enenitrile: Retension time=1.21 min (Method A); (M−H)⁻=386.

EXAMPLE 11

5-[6-Hydroxy-7-(1,1,4-trioxo-1,2,5-thiadiazolidin-2-yl)-naphthalen-2-yl]-pentanoic acid 5-[6-Hydroxy-7-(1,1,4-trioxo-1,2,5-thiadiazolidin-2-yl)-naphthalen-2-yl]-pentanoic acid To a solution of 5-[6-hydroxy-7-(1,1,4-trioxo-[1,2,5]thiadiazolidin-2-yl)-naphthalen-2-yl]-pentanoic acid ethyl ester (Example 8, 0.025 g, 0.053 mmol) in MeOH/H₂O (3 mL) is added KOH (0.009 g, 0.159 mmol). This is stirred at 50° C. for 18 h. LC/MS reveals the desired product, so the reaction solution is acidified using 1 N HCl, extracted with EtOAc. The organic layer is washed with brine, dried over MgSO₄, filtered, and concentrated in vacuo to afford 5-[6-hydroxy-7-(1,1,4-trioxo-1,2,5-thiadiazolidin-2-yl)-naphthalen-2-yl]-pentanoic acid as a white solid: ¹H NMR (MeOD) δ7.88 (s, 1H), 7.59 (d, J=8.0 Hz, 1H), 7.54 (s, 1H), 7.31 (dd, J=8.46, 1.64 Hz, 1H), 7.21 (s, 1H), 4.61 (s, 2H), 2.75 (t, J=7.33 Hz, 2H), 2.32 (t, J=7.07 Hz, 2H), 1.61 (m, 4H). Retention time=0.87 min (Method A); (M−H)⁻=377.

EXAMPLE 12

5-[3-Hydroxy-7-(5-hydroxypentyl)-naphthalen-2-yl]-1,1-dioxo-1,2,5-thiadiazolidin-3-one

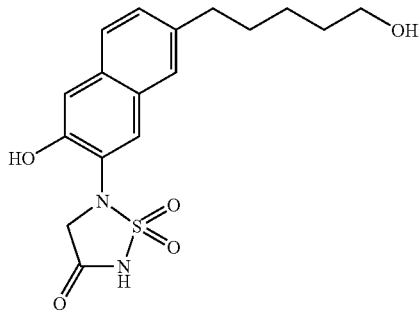

A. 5-[6-Benzyloxy-7-(1,1,4-trioxo)-1,2,5-thiadiazolidin-2-yl)-naphthalen-2-yl]-pentanoic acid 5-[6-Benzyloxy-7-(1,1,4-trioxo)-1,2,5-thiadiazolidin-2-yl)-naphthalen-2-yl]-pentanoic acid is prepared analogously to Example 11, starting with 5-[6-benzyloxy-7-(1,1,4-trioxo)-1,2,5-thiadiazolidin-2-yl)-naphthalen-2-yl]-pentanoic acid ethyl ester (Example 8, step A).

B. 5-[3-Benzyloxy-7-(5-hydroxypentyl)-naphthalen-2-yl]-1,1-dioxo-1,2,5-thiadiazolidin-3-one To a solution of 5-[6-benzyloxy-7-(1,1,4-trioxo)-1,2,5-thiadiazolidin-2-yl)-naphthalen-2-yl]-pentanoic acid (0.014 g, 0.030 mmol) in THF (1 mL) is added borane-THF complex (1.0M, 0.089 mL, 0.089 mmol). There is immediate bubbling of the reaction solution and after 20 min, LC/MS reveals complete reduction. The solution is diluted with EtOAc and 1 N HCl. The aqueous layer is removed and the organic layer is washed with brine, dried over MgSO$_4$, filtered, and concentrated in vacuo to afford 5-[3-benzyloxy-7-(5-hydroxypentyl)-naphthalen-2-yl]-1,1-dioxo-1,2,5-thiadiazolidin-3-one as a white solid.

C. 5-[3-Hydroxy-7-(5-hydroxy-pentyl)-naphthalen-2-yl]-1,1-dioxo-1,2,5-thiadiazolidin-3-one 5-[3-Hydroxy-7-(5-hydroxy-pentyl)-naphthalen-2-yl]-1,1-dioxo-1,2,5-thiadiazolidin-3-one is prepared analogously to Example 4, step B: $^1$H NMR (MeOD) δ 8.48 (s, 1H), 7.92 (d, J=4 Hz, 1H), 7.55 (dd, J=4 Hz, 1H), 7.50 (br s, 1H), 7.23 (m, 1H), 7.17 (m, 1H), 4.46 (s, 2H), 2.69 (m, 5H), 2.20 (m, 2H), 1.67 (m, 4H). Retention time=0.82 min (Method A); (M−H)−=363.

EXAMPLE 13

2-Hydroxy-6-{2-[6-hydroxy-7-(1,1,4-trioxo-1,2,5-thiadiazolidin-2-yl)-naphthalen-2-yloxy]-ethoxy}-N,N-dimethylbenzamide

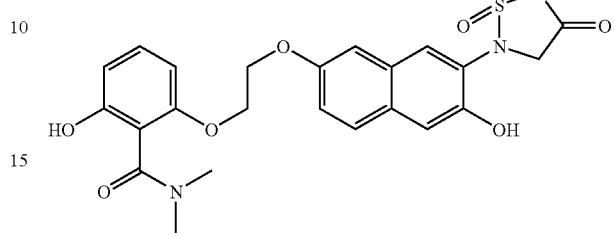

A. 2,6-Dimethoxy-N,N-dimethylbenzamide

To a solution of dimethylamine (42 mL, 84 mmol) in THF at 0° C. is added 2,6-dimethoxybenzoyl chloride (5.58 g, 27.8 mmol) and it is warmed to RT and stirred for 18 h. The mixture is poured to EtOAc, washed with water, 1 N HCl solution and brine. The solvent is removed and concentrated to give the title compound and it is used in the next step.

B. 2,6-Dihydroxy-N,N-dimethylbenzamide

The title compound is prepared based on the same procedure described in Example 3, step E.

C. 2-Benzyloxy-6-hydroxy-N,N-dimethylbenzamide

The title compound is prepared analogously to Example 1, step B.

D. 3,7-Dihydroxynaphthalene-2-carboxylic acid methyl ester

To a solution of 3,7-dihydroxynaphthalene-2-carboxylic acid (4.0 g, 19.6 mmol) in MeOH (80 mL) is added thionyl chloride (10 mL, 136 mmol) and it is stirred at RT for 48 h. The solvent is removed and purified to give the title compound.

E. 7-tert-Butoxycarbonylmethoxy-3-hydroxynaphthalene-2-carboxylic acid methyl ester A mixture of 3,7-dihydroxynaphthalene-2-carboxylic acid methyl ester (3.32 g, 15.5 mmol), bromoacetic acid tert-butyl ester (2.29 mL, 15.5 mmol) and potassium carbonate (4.28 g, 31.0 mmol) in DMF (20 mL) is stirred at 60° C. for 18 h. The reaction mixture is poured to EtOAc, wash with water and brine. It is then dried with MgSO$_4$ and concentrated to give the title compound.

F. 3-Benzyloxy-7-tert-butoxycarbonylmethoxynaphthalene-2-carboxylic acid methyl ester The title compound is prepared analogously to Example 1, step B.

G. 3-Benzyloxy-7-carboxymethoxynaphthalene-2-carboxylic acid methyl ester 7-tert-butoxycarbonylmethoxy-3-hydroxynaphthalene-2-carboxylic acid methyl ester (1.35 g, 3.2 mmol) in formic acid (5 mL) is stirred at RT for 2 h. The mixture is poured into water, filtered and washed with water. After it is air dried for 18 h, it is dissolved in EtOAc, dried with MgSO$_4$, concentrated to give the title compound.

H. 3-Benzyloxy-7-(2-hydroxyethoxy)-naphthalene-2-carboxylic acid methyl ester

The title compound is prepared analogously to Example 12, step B.

I. 3-Benzyloxy-7-[2-(3-benzyloxy-2-dimethylcarbamoylphenoxy)-ethoxy]-naphthalene-2-carboxylic acid methyl ester A mixture of 3-benzyloxy-7-(2-hydroxyethoxy)-naphthalene-2-carboxylic acid methyl ester (239 mg, 0.68 mmol), triphenylphosphine (445 mg, 1.70 mmol) and DIAD (0.334 mL, 1.70 mmol) in THF (10 mL) is stirred at RT for 15 min. Then 2-benzyloxy-6-hydroxy-N,N-dimethylbenzamide (460 mg, 1.70 mmol) in THF (8 mL) is added drop wise and the mixture is stirred at RT for 18 h. The solvent is removed and the residue is purified to give the title compound.

J. {3-Benzyloxy 7-[2-(3-benzyloxy-2-dimethylcarbamoylphenoxy)-ethoxy]-1,2-dihydronaphthalen-2-yl}-carbamicacid tert-butyl ester The title compound is prepared analogously to Example 2, steps B-C.

K. 2-[2-(7-Amino-6-benzyloxy-7,8-dihydronaphthalen-2-yloxy)-ethoxy]-6-benzyloxy-N,N-dimethylbenzamide The title compound is prepared analogously to step G.

L. 2-Hydroxy-6-{2-[6-hydroxy-7-(1,1,4-trioxo-1,2,5-thiadiazolidin-2-yl)-naphthalen-2-yloxy]-ethoxy}-N,N-dimethylbenzamide The title compound is prepared analogously to 1, steps E-1, except using formic acid to replace TFA/DCM in step G: NMR (δ, DMSO-d$_6$): 7.90 (s, 0.1H), 7.67 (d, 1H, J=10.1 Hz), 7.14 (m, 5H), 7.00 (dd, 1H, J=8.3, 3.7 Hz), 6.53 (2H, dd, J=28.7, 8.3 Hz), 4.30 (m, 4H), 4.20 (s, 2H), 2.86° (s, 3H), 2.73 (s, 3H). (M–H)$^-$=500.

EXAMPLE 14

2-Hydroxy-6-{4-[6-hydroxy-7-(1,1,4-trioxo-1,2,5-thiadiazolidin-2-yl)-naphthalen-2-yl]-butoxy}-N,N-dimethylbenzamide

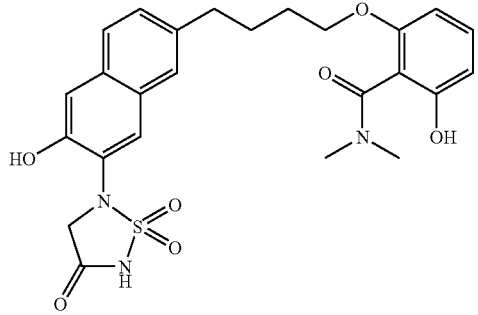

A. 2-Benzyloxy-6-but-3-enyloxy-N,N-dimethylbenzamide

The title compound is prepared analogously to Example 1, step B, from 2-benzyloxy-6-hydroxy-N,N-dimethylbenzamide (Example 13, step C) except using 4-bromo-but-1-ene to replace benzyl bromide.

B. 2-Benzyloxy-6-{(E)-4-[6-benzyloxy-7-(1,1,4-trioxo-1,2,5-thiadiazolidin-2-yl)-naphthalen-2-yl]-but-3-enyloxy}-N,N-dimethylbenzamide To a microwave vial is added 5-(3-benzyloxy-7-bromonaphthalen-2-yl)-1,1-dioxo-1,2,5-thiadiazolidin-3-one (36 mg, 0.082 mmol), 2-benzyloxy-6-but-3-enyloxy-N,N-dimethylbenzamide (53 mg, 0.163 mmol), Pd(OAc)$_2$ (5 mg, 0.021 mmol) and 2-(di-t-butylphosphino)biphenyl (6 mg, 0.021 mmol). The mixture is diluted with acetonitrile (2 mL) and triethylamine (0.023 mL, 0.163 mmol). This is stirred in a microwave for 30 min at 100° C. The reaction mixture is filtered, acidified with 1 N HCl solution and extracted with EtOAc. The organic layer is concentrated and used directly in the next step.

C. 2-Hydroxy-6-{4-[6-hydroxy-7-(1,1,4-trioxo-1,2,5-thiadiazolidin-2-yl)-naphthalen-2-yl]-butoxy}-N,N-dimethylbenzamide The title compound is prepared analogously to Example 4, step B: (M–H)$^-$=512.

EXAMPLE 15

The following examples are prepared using appropriate starting materials and general procedures described in Example 14 steps B-C.

| Example | Chemical Name | MS (m/z) | Retention time (min) Method |
|---|---|---|---|
| 15-1 | 5-{3-Hydroxy-7-[3-(2-hydroxyethoxy)-propyl]-naphthalen-2-yl}-1,1-dioxo-1,2,5-thiadiazolidin-3-one | (M – H)$^-$ = 379 | 0.85 A |
| 15-2 | 5-{3-Hydroxy-7-[2-(2-methoxyphenyl)-ethyl]-naphthalen-2-yl}-1,1-dioxo-1,2,5-thiadiazolidin-3-one | (M – H)$^-$ = 411 | 1.02 A |
| 15-3 | 5-[3-Hydroxy-7-(5-oxohexyl)-naphthalen-2-yl]-1,1-dioxo-1,2,5-thiadiazolidin-3-one | (M – H)$^-$ = 375 | 0.81 A |

-continued

| Example | Chemical Name | MS (m/z) | Retention time (min) Method |
|---|---|---|---|
| 15-4 | 5-{7-[3-(3,5-Dimethylpyrazol-1-yl)-propyl]-3-hydroxy-naphthalen-2-yl}-1,1-dioxo-1,2,5-thiadiazolidin-3-one | (M − H)⁻ = 413 | |
| 15-5 | 5-{3-Hydroxy-7-[3-(2-oxocyclohexyl)-propyl]-naphthalen-2-yl}-1,1-dioxo-1,2,5-thiadiazolidin-3-one | (M − H)⁻ = 415 | 1.26 A |
| 15-6 | 5-{3-Hydroxy-7-[4-hydroxy-4-(tetrahydrofuran-2-yl)-butyl]-naphthalen-2-yl}-1,1-dioxo-1,2,5-thiadiazolidin-3-one | (M − H)⁻ = 419 | 1.04 A |
| 15-7 | 5-{3-Hydroxy-7-[1-(2-oxopyrrolidin-1-yl)-ethyl]naphthalen-2-yl}-1,1-dioxo-1,2,5-thiadiazolidin-3-one | (M − H)⁻ = 388 | 0.86 A |
| 15-8 | 5-[3-Hydroxy-7-(3-phenylpropyl)-naphthalen-2-yl]-1,1-dioxo-1,2,5-thiadiazolidin-3-one | (M − H)⁻ = 395 | 1.39 A |
| 15-9 | 5-[3-Hydroxy-7-(3-pentafluorophenylpropyl)-naphthalen-2-yl]-1,1-dioxo-1,2,5-thiadiazolidin-3-one | (M − H)⁻ = 485 | 1.49 A |
| 15-10 | 2-{3-[6-Hydroxy-7-(1,1,4-trioxo-1,2,5-thiadiazolidin-2-yl)-naphthalen-2-yl]-propyl}benzonitrile | (M − H)⁻ = 420 | 1.28 A |
| 15-11 | 5-[3-Hydroxy-7-((R)-4-hydroxypentyl)-naphthalen-2-yl]-1,1-dioxo-1,2,5-thiadiazolidin-3-one | (M − H)⁻ = 363 | 0.88 A |
| 15-12 | 5-[3-Hydroxy-7-(4-hydroxypentyl)-naphthalen-2-yl]-1,1-dioxo-1,2,5-thiadiazolidin-3-one | (M − H)⁻ = 363 | |
| 15-13 | 5-[3-Hydroxy-7-(4-hydroxy-3-methylbutyl)-naphthalen-2-yl]-1,1-dioxo-1,2,5-thiadiazolidin-3-one | (M − H)⁻ = 363 | 0.95 A |
| 15-14 | 5-[7-(4-Ethyl-4-hydroxyhexyl)-3-hydroxynaphthalen-2-yl]-1,1-dioxo-1,2,5-thiadiazolidin-3-one | (M − H)⁻ = 405 | 1.18 A |
| 15-15 | 5-[3-Hydroxy-7-(4-hydroxyheptyl)-naphthalen-2-yl]-1,1-dioxo-1,2,5-thiadiazolidin-3-one | (M − H)⁻ = 391 | 1.14 A |
| 15-16 | 5-{3-Hydroxy-7-[3-(1-hydroxycyclohexyl)-propyl]-naphthalen-2-yl}-1,1-1,2,5-thiadiazolidin-3-one | (M − H)⁻ = 417 | 1.16 A |
| 15-17 | 5-[6-Hydroxy-7-(1,1,4-trioxo-1,2,5-thiadiazolidin-2-yl)-naphthalen-2-yl]-2,2-dimethylpentanoic acid | (M − H)⁻ = 405 | 0.96 A |
| 15-18 | 5-{3-Hydroxy-7-[2-((1S,2R)-2-hydroxycyclopentyl)-ethyl]-naphthalen-2-yl}-1,1-dioxo-1,2,5-thiadiazolidin-3-one | (M − H)⁻ = 389 | 1.06 A |
| 15-19 | 5-[6-Hydroxy-7-(1,1,4-trioxo-1,2,5-thiadiazolidin-2-yl)-naphthalen-2-yl]-pentanenitrile | (M − H)⁻ = 358 | 1.03 A |

EXAMPLE 16

5-{3-Hydroxy-7-[3-(2-hydroxycyclohexyl)-propyl]-naphthalen-2-yl}-1,1-dioxo-1,2,5-thiadiazolidin-3-one

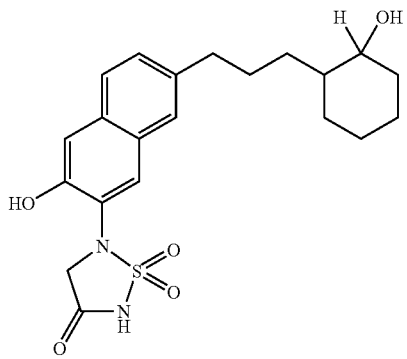

The title compound is prepared analogously to Example 45, step A, from 5-{3-hydroxy-7-[3-(2-oxocyclohexyl)-propyl]-naphthalen-2-yl}-1,1-dioxo-1,2,5-thiadiazolidin-3-one (Example 15-5): Retention time=1.20 min (Method A); (M−H)⁻=417.

EXAMPLE 17

5-[6-Hydroxy-7-(1,1,4-trioxo-1,2,5-thiadiazolidin-2-yl)-naphthalen-2-yl]-2,2-dimethylpentanoic acid methyl ester

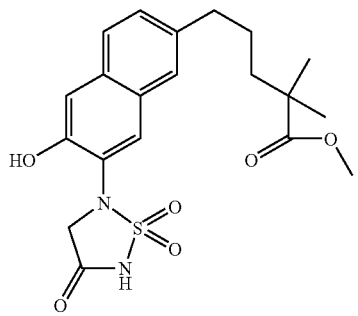

To a solution of 5-[6-hydroxy-7-(1,1,4-trioxo-1,2,5-thiadiazolidin-2-yl)-naphthalen-2-yl]-2,2-dimethylpentanoic acid (Example LCE840, 63 mg, 0.13 mmol) in MeOH at 0° C. is added DIEA (0.032 mL, 0.13 mmol). After is stirred for 2 min, trimethylsilyldiazomethane (2M, 0:07 mL) is added drop wise. The reaction mixture is stirred for 15 min and concentrated give the title compound: Retention time=1.28 min (Method A); (M–H)⁻=419.

EXAMPLE 18

5-[3-Hydroxy-7-(1,5,6-trifluoro-4-hydroxy-4-methylpentyl)-naphthalen-2-yl]-1,1-dioxo-1,2,5-thiadiazolidin-3-one

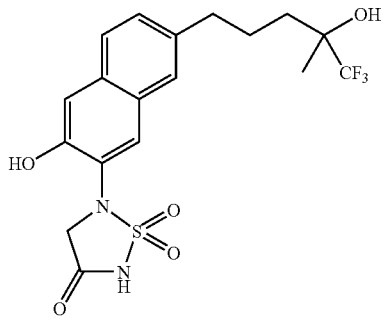

A. 1,1,1-Trifluoro-2-methylpent-4-en-2-ol

To a solution of 1,1,1-trifluoropropan-2-one (0.5 mL, 5.36 mmol) in THF (10 mL) at −78° C. is added allylmagnisum bromide (10 mL, 10 mmol, 1.0 M in Et₂O) drop wise and a cloudy precipitate appears. The reaction mixture is warmed to RT and stirred for 18 h. Saturated NH₄Cl solution is added and 1 N HCl is used to adjust pH=2. The mixture is extracted with Et₂O, wash with brine, dried with Na₂SO₄ and concentrated to give the title compound.

B. 5-[3-Hydroxy-7-(5,5,5-trifluoro-4-hydroxy-4-methylpentyl)-naphthalen-2-yl]-1,1-dioxo-1,2,5-thiadiazolidin-3-one The title compound is prepared analogously to Example 14, steps B-C: (M–H)⁻=431.

EXAMPLE 19

Acetic acid 4-[6-hydroxy-7-(1,1,4-trioxo-1,2,5-thiadiazolidin-2-yl)-naphthalen-2-yl]-2-methyl butyl ester

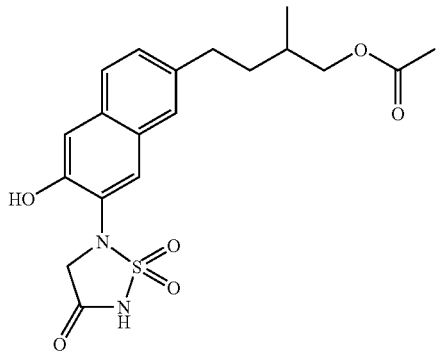

A. Acetic acid 2-methyl-but-3-enyl ester

To a solution of but-3-en-2-ol (0.16 mL, 1.6 mmol) in pyridine (1 mL) is added acetic anhydride (0.28 mL, 1.6 mmol) and the mixture is heated at 50° C. for 18 h. Pyridine is removed by washing with Et₂O and 1 N HCl solution, followed by sat. CuSO₄, water and brine. The organic layer is dried with NaSO₄ and concentrated to give the title compound.

B. Acetic acid 4-[6-hydroxy-7-(1,1,4-trioxo-1,2,5-thiadiazolidin-2-yl)-naphthalen-2-yl]-2-methyl butyl ester The title compound is prepared analogously to Example 14, steps B-C: Retention time=1.18 min; (M–H)⁻=405.

EXAMPLE 20

5-[3-Hydroxy-7-(5,5,5-trifluoro-4-hydroxypentyl)-naphthalen-2-yl]-1,1-dioxo-1,2,5-thiadiazolidin-3-one

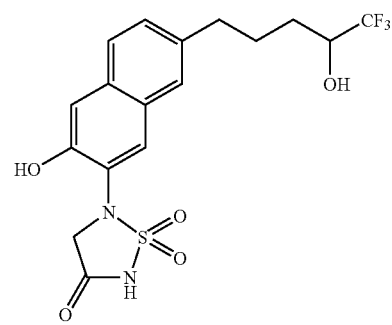

A. 1,1,1-Trifluoro-pent-4-en-2-ol

To a suspension of indium powder (2.3 g, 20 mmol) in water is added allyl bromide (2.5 mL, 30 mmol) followed by trifluoroacetaldehyde ethyl hemiacetal (1.3 mL, 10 mmol). The reaction mixture is stirred for 16 h and then extracted with t-butyl methyl ether (50 mL). The organic layer is washed with water, brine, dried with Na₂SO₄ and concentrated to give the title compound as a colorless oil.

B. 5-[3-Hydroxy-7-(5,5,5-trifluoro-4-hydroxypentyl)-naphthalen-2-yl]-1,1-dioxo-1,2,5-thiadiazolidin-3-one The title compound is prepared analogously to Example 14, steps B-C, Retention time=1.12 min (Method A), (M–H)⁻=417.

EXAMPLE 21

5-[3-Hydroxy-7-(4-hydroxy-4-methylpentyl)-naphthalen-2-yl]-1,1-dioxo-1,2,5-thiadiazolidin-3-one

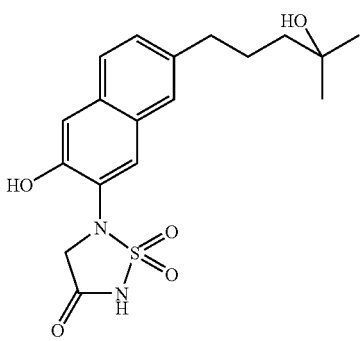

A. 2-Methylpent-4-en-2-ol

Acetone (0.52 mL, 7 mmol) and magnesium bromide ethyl etherate (6.5 g, 25 mmol) is diluted in THF (20 mL) under $N_2$. At −25° C. allyl magnesium bromide (10 mL, 10 mmol, 1M) is added and then the white suspension is allowed to warm up to RT and stirred for 18 h. 1 N HCl solution is added until the pH is neutral. Then the aq. layer is separated and washed twice with ether (20 mL). The combined organic layers are dried with $NaSO_4$ and the solvent is evaporated to give the title compound as a pale yellow oil.

B. 5-[3-Hydroxy-7-(4-hydroxy-4-methylpentyl)-naphthalen-2-yl]-1,1-dioxo-1,2,5-thiadiazolidin-3-one The title compound is prepared analogously to Example 14, steps B-C: Retention time 1.01 min (Method A) (M–H)⁻=377.

EXAMPLE 22

5-(7-Cyclopentyl-3-hydroxynaphthalen-2-yl)-1,1-dioxo-1,2,5-thiadiazolidin-3-one

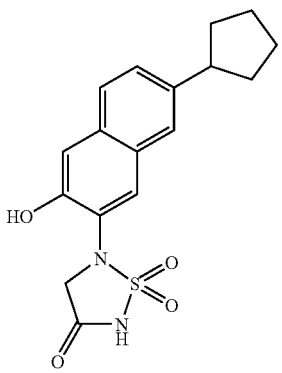

A. 5-(3-Benzyloxy-7-cyclopent-1-enyl-naphthalen-2-yl)-1,1-dioxo-1,2,5-thiadiazolidin-3-one In a microwave vial is added 5-(3-benzyloxy-7-bromonaphthalen-2-yl)-1,1-dioxo-1,2,5-thiadiazolidin-3-one (0.100 g, 0.224 mmol), cyclopentene (0.04 mL, 0.453 mmol), palladium acetate (0.010 g, 0.0445 mmol), triethylamine (0.063 mL, 0.448 mmol) and acetonitrile (2 mL). The vial is capped and placed in the microwave for 15 min at 110° C. The reaction mixture is filtered over Celite and washed with acetonitrile. The filtrate is concentrated and the residue is purified via Biotage Sp1, eluting with 15-60% EtOH/$H_2O$ to afford 5-(3-benzyloxy-7-cyclopent-1-enyl-naphthalen-2-yl)-1,1-dioxo-1,2,5-thiadiazolidin-3-one (0.0127 g): (M–H)⁻=433.

B. 5-(7-Cyclopentyl-3-hydroxynaphthalen-2-yl)-1,1-dioxo-1,2,5-thiadiazolidin-3-one The title compound is prepared analogously to Example 4, step B: Retention time=1.38 min (Method A); (M–H)⁻=345.

EXAMPLE 23

5-(7-Cyclohexyl-3-hydroxynaphthalen-2-yl)-1,1-dioxo-1,2,5-thiadiazolidin-3-one

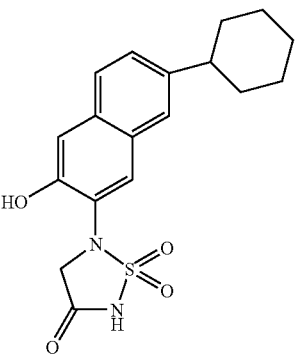

5-(7-Cyclohexyl-3-hydroxynaphthalen-2-yl)-1,1-dioxo-1,2,5-thiadiazolidin-3-one is prepared following the procedures outlined in Example 22: Retention time=1.35 min (Method A); (M–H)⁻=359.

EXAMPLE 24

5-[3-Hydroxy-7-(3-methylsulfanylphenyl)-naphthalen-2-yl]-1,1-dioxo-1,2,5-thiadiazolidin-3-one

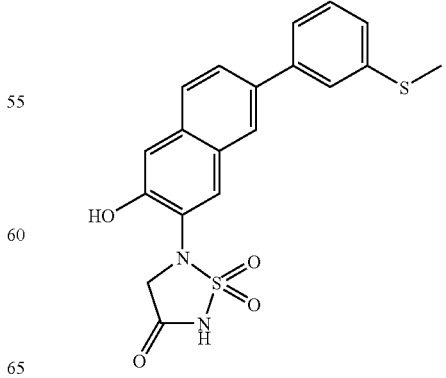

A. 5-[3-Benzyloxy-7-(3-methylsulfanylphenyl)-naphthalen-2-yl]-1,1-dioxo-1,2,5-thiadiazolidin-3-one The title compound is prepared analogously to Example 4, step A.

B. 5-[3-Hydroxy-7-(3-methylsulfanylphenyl)-naphthalen-2-yl]-1,1-dioxo-1,2,5-thiadiazolidin-3-one The title compound is prepared analogously to Example 3, step E: Retention time=1.22 min (Method A); (M–H)⁻=399.

EXAMPLE 25

5-[3-Hydroxy-7-((E)-4-hydroxy-4-methylpent-1-enyl)-naphthalen-2-yl]-1,1-dioxo-1,2,5-thiadiazolidin-3-one

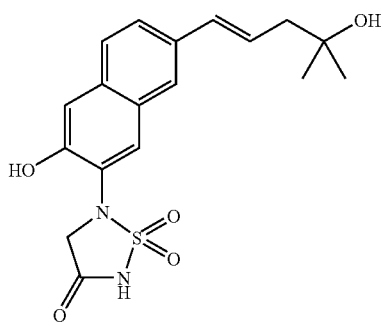

The title compound is prepared analogously to Example 14 step B, using 5-(7-bromo-3-hydroxynaphthalen-2-yl)-1,1-dioxo-1,2,5-thiadiazolidin-3-one (Example 3, step E) to replace 5-(3-benzyloxy-7-bromonaphthalen-2-yl)-1,1-dioxo-1,2,5-thiadiazolidin-3-one: Retention time=0.94 min (Method A); (M–H)⁻=375.

EXAMPLE 26

5-[6-Hydroxy-7-(1,1,4-trioxo-1,2,5-thiadiazolidin-2-yl)-naphthalen-2-yl]-thiophene-2-carbonitrile

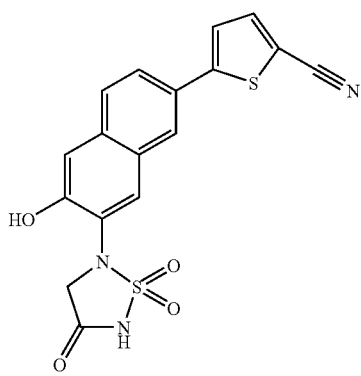

The title compound is prepared analogously to Example 4, step A, using 5-(7-bromo-3-hydroxynaphthalen-2-yl)-1,1-dioxo-1,2,5-thiadiazolidin-3-one (Example 3, step E) to replace 5-(3-benzyloxy-7-bromonaphthalen-2-yl)-1,1-dioxo-1,2,5-thiadiazolidin-3-one: Retention time=1.08 min (Method A); (M–H)⁻=384.

EXAMPLE 27

{3-[6-Hydroxy-7-(1,1,4-trioxo-1,2,5-thiadiazolidin-2-yl)-naphthalen-2-yl]-benzyl}-carbamic acid methyl ester

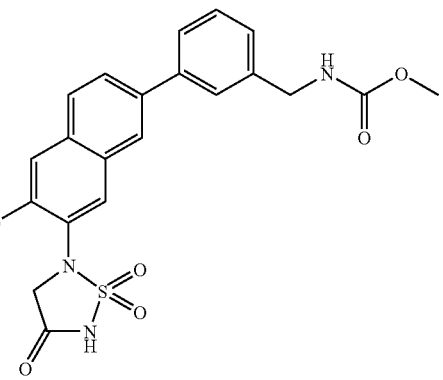

A. 5-[7-(3-Aminomethylphenyl)-3-benzyloxynaphthalen-2-yl]-1,1-dioxo-1,2,5-thiadiazolidin-3-one 5-[7-(3-Aminomethylphenyl)-3-benzyloxynaphthalen-2-yl]-1,1-dioxo-1,2,5-thiadiazolidin-3-one is prepared according to the general procedure outlined in Example 4, step A, starting with (3-aminomethylphenyl)boronic acid and 5-(3-benzyloxy-7-bromonaphthalen-2-yl)-1,1-dioxo-1,2,5-thiadiazolidin-3-one: (M–H)⁻=472.

B. {3-[6-Benzyloxy-7-(1,1,4-trioxo-1,2,5-thiadiazolidin-2-yl)-naphthalen-2-yl]-benzyl}-carbamic acid methyl ester To a stirring solution of 5-[7-(3-aminomethylphenyl)-3-benzyloxynaphthalen-2-yl]-1,1-dioxo-1,2,5-thiadiazolidin-3-one (0.046 g, 0.097 mmol) and triethylamine (0.014 mL, 0.098 mmol) in THF (3 mL) at 0° C. is added methyl chloroformate (0.008 mL, 0.104 mmol). The reaction is stirred for 30 min and then quenched with water and extracted with $CH_2Cl_2$ (3×25 mL). The organic layers are combined and concentrated. The residue is purified via Biotage Sp1 eluting with 5-60% $CH_3CN/H_2O$ to afford {3-[6-benzyloxy-7-(1,1,4-trioxo-1,2,5-thiadiazolidin-2-yl)-naphthalen-2-yl]-benzyl}-carbamic acid methyl ester: (M–H)⁻=530.

C. {3-[6-Hydroxy-7-(1,1,4-trioxo-1,2,5-thiadiazolidin-2-yl)-naphthalen-2-yl]-benzyl}-carbamic acid methyl ester {3-[6-Hydroxy-7-(1,1,4-trioxo-1,2,5-thiadiazolidin-2-yl)-naphthalen-2-yl]-benzyl}-carbamic acid methyl ester is prepared according to the general procedure outlined in Example 4, step B: Retention time=0.98 min (Method A); (M–H)⁻=440.

EXAMPLE 28

(E)-5-[6-Hydroxy-7-(1,1,4-trioxo-1,2,5-thiadiazolidin-2-yl)-naphthalen-2-yl]-pent-4-enenitrile

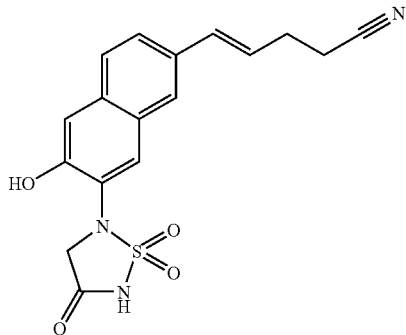

The title compound is prepared analogously to Example 8, step A, beginning with pent-4-ynenitrile and 5-(7-bromo-3-hydroxynaphthalen-2-yl)-1,1-dioxo-1,2,5-thiadiazolidin-3-one (Example 3, step E): Retention time=0.91 min (Method A); (M−H)⁻=356.

EXAMPLE 29

(E)-5-[6-Hydroxy-7-(1,1,4-trioxo-1,2,5-thiadiazolidin-2-yl)-naphthalen-2-yl]-2-methylpent-4-enoic acid ethyl ester

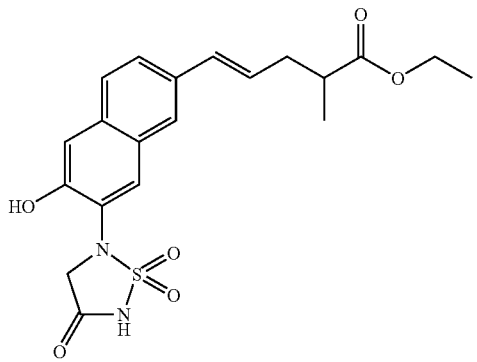

The title compound is prepared analogously to Example 25 using 2-methylpent-4-enoic acid ethyl ester: (M−H)⁻=417.

EXAMPLE 30

(E)-5-[6-Hydroxy-7-(1,1,4-trioxo-1,2,5-thiadiazolidin-2-yl)naphthalen-2-yl]-2-methylpent-4-enoic acid

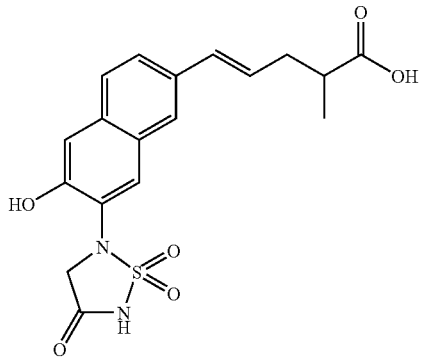

The title compound is prepared analogously to 11 from (E)-5-[6-hydroxy-7-(1,1,4-trioxo-1,2,5-thiadiazolidin-2-yl)-naphthalen-2-yl]-2-methylpent-4-enoic acid ethyl ester (Example 29): (M−H)⁻=389.

EXAMPLE 31

(E)-5-[6-Hydroxy-7-(1,1,4-trioxo-1,2,5-thiadiazolidin-2-yl)-naphthalen-2-yl]-pent-4-enoic acid

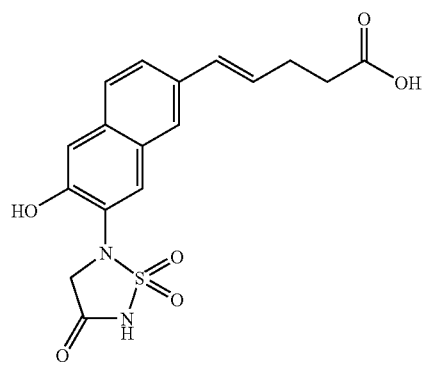

A. (E)-5-[6-Hydroxy-7-(1,1,4-trioxo-1,2,5-thiadiazolidin-2-yl)-naphthalen-2-yl]-pent-4-enoic acid ethyl ester The title compound is prepared analogously to Example 25 using pent-4-enoic acid ethyl ester.

B. (E)-5-[6-Hydroxy-7-(1,1,4-trioxo-1,2,5-thiadiazolidin-2-yl)-naphthalen-2-yl]-pent-4-enoic acid The title compound is prepared analogously to Example 11: Retention time=1.35 min (Method A); (M−H)⁻=375.

EXAMPLE 32

5-[6-Hydroxy-7-(1,1,4-trioxo-1,2,5-thiadiazolidin-2-yl)-naphthalen-2-yl]-pentanoic acid isopropyl ester

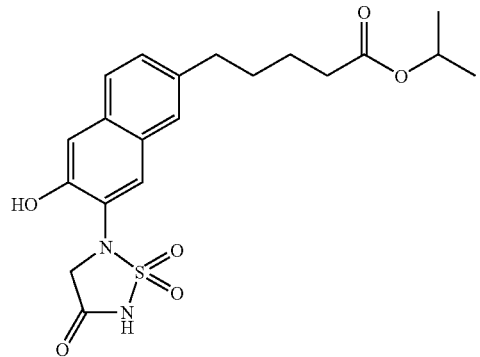

A. 5-[6-Hydroxy-7-(1,1,4-trioxo-1,2,5-thiadiazolidin-2-yl)-naphthalen-2-yl]-pentanoic acid ethyl ester 5-[6-Hydroxy-7-(1,1,4-trioxo-1,2,5-thiadiazolidin-2-yl)-naphthalen-2-yl]-pentanoic acid ethyl ester is prepared analogously to 8, steps A-B starting with pent-4-enoic acid ethyl ester.

B. 5-[6-Hydroxy-7-(1,1,4-trioxo-1,2,5-thiadiazolidin-2-yl)-naphthalen-2-yl]-pentanoic acid isopropyl ester To a stirring solution of 5-[6-hydroxy-7-(1,1,4-trioxo-1,2,5-thiadiazolidin-2-yl)-naphthalen-2-yl]-pentanoic acid ethyl ester (0.003 g, 0.007 mmol) in iPrOH (1 mL) is added t-BuOK (1M in THF, 0.044 mL). The mixture is stirred for 18 h at room temperature. The reaction is quenched with 1 N HCl (1.5 mL) and extracted with EtOAc (3×10 mL). The organic layers are dried and concentrated. The residue is passed through a short column of reverse phase silica gel eluting with 40% MeOH/H$_2$O to afford 5-[6-hydroxy-7-(1,1,4-trioxo-1,2,5-thiadiazolidin-2-yl)-naphthalen-2-yl]-pentanoic acid isopropyl ester: Retention time=1.17 min (Method A); (M−H)⁻=419.

EXAMPLE 33

5-[6-Hydroxy-7-(1,1,4-trioxo-1,2,5-thiadiazolidin-2-yl)-naphthalen-2-yl]-2-methylpentanoic acid methyl ester

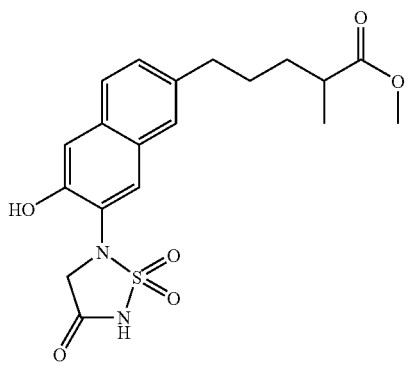

The title compound is prepared analogously to Example 32, step B, starting from 5-[6-hydroxy-7-(1,1,4-trioxo-1,2,5-thiadiazolidin-2-yl)-naphthalen-2-yl]-2-methylpentanoic acid ethyl ester (Example 9-4) and the reaction is performed in solvent MeOH instead of i-PrOH: Retention time=1.17 min (Method A); (M−H)⁻=405.

EXAMPLE 34

5-[6-Hydroxy-7-(1,1,4-trioxo-1,2,5 thiadiazolidin-2-yl)-naphthalen-2-yl]-2-methylpentanoic acid

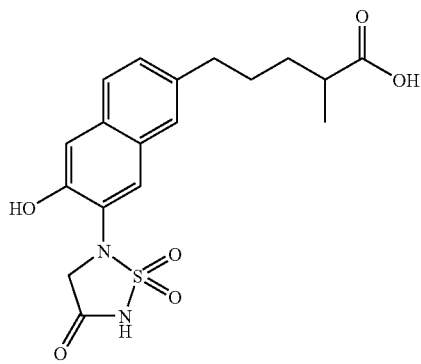

The title compound is prepared analogously to Example 11, starting from 5-[6-hydroxy-7-(1,1,4-trioxo-1,2,5-thiadiazolidin-2-yl)-naphthalen-2-yl]-2-methylpentanoic acid ethyl ester (Example 9-4): Retention time=0.80 min (Method A); (M−H)⁻=391.

EXAMPLE 35

5-[7-(4,5-Dihydroxy-4,5-dimethylhex-1-enyl)-3-hydroxynaphthalen-2-yl]-1,1-dioxo-1,2,5-thiadiazolidin-3-one

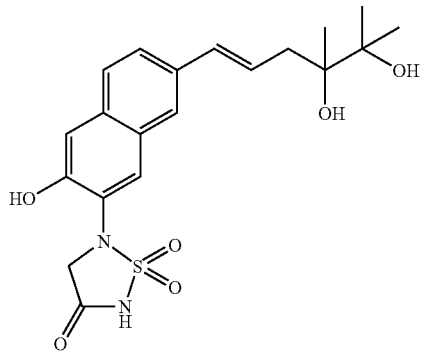

A. 2-Hydroxy-2-methylpent-4-enoic acid methyl ester

To a stirring solution of 2-oxopropionic acid methyl ester (1.0 g, 0.903 mmol), allyl bromide (1.8 mL, 21.32 mmol) in MeOH/HCl (1:4, 10 mL), is added indium powder (1.12 g, 9.76 mmol). The mixture is stirred for 3 days at room temperature. The mixture is quenched with NaHCO$_3$ and extracted with DCM (3×50 mL). The organic layers are washed with water (2×50 mL) and brine. The combined organic layers are dried with MgSO₄ and concentrated to afford 2-hydroxy-2-methylpent-4-enoic acid methyl ester: (M+H)⁺=145.

B. 2,3-Dimethylhex-5-ene-2,3-diol

To a stirring solution of 2-hydroxy-2-methylpent-4-enoic acid methyl ester (1.12 g, 7.77 mmol) in THF (8 mL) at 0° C. is added MeMgBr (10 mL, 30 mmol) drop wise. The mixture is stirred for 3 h at room temperature and then quenched with sat. NH₄Cl. It is then extracted with Et₂O (3×50 mL). The organic layers are washed with water and brine, dried and concentrated to afford 2,3-dimethylhex-5-ene-2,3-diol.

C. 5-[7-(4,5-Dihydroxy-4,5-dimethylhex-1-enyl)-3-hydroxynaphthalen-2-yl]-1,1-dioxo-1,2,5-thiadiazolidin-3-one 5-[7-(4,5-Dihydroxy-4,5-dimethylhex-1-enyl)-3-hydroxynaphthalen-2-yl]-1,1-dioxo-1,2,5-thiadiazolidin-3-one is prepared analogously to Example 25, (M−H)⁻=419.

EXAMPLE 36

5-[7-(4,5-Dihydroxy-4,5-dimethylhexyl)-3-hydroxynaphthalen-2-yl]-1,1-dioxo-1,2,5-thiadiazolidin-3-one

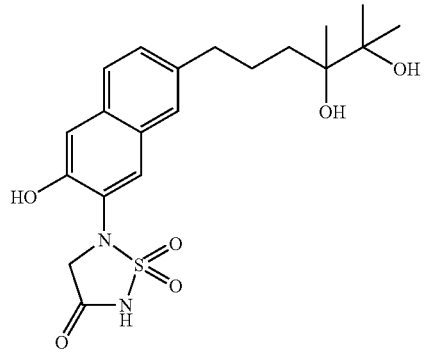

The title compound is prepared analogously to Example 8 starting from 2,3-dimethyl-hex-5-ene-2,3-diol: Retention time=0.94 min (Method A); (M−H)⁻=421.

EXAMPLE 37

5-[7-(4,4-Dimethylpentyl)-3-hydroxynaphthalen-2-yl]-1,1-dioxo-1,2,5-thiadiazolidin-3-one

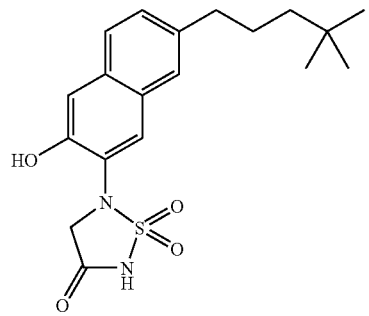

The title compound is prepared analogously to Example 28: Retention time=1.37 min (Method A); (M−H)⁻=375.

EXAMPLE 38

Benzoic acid 6-(3-cyano-3-methylpropyl)-3-(1,1,4-trioxo-1,2,5-thiadiazolidin-2-yl)-naphthalen-2-yl ester

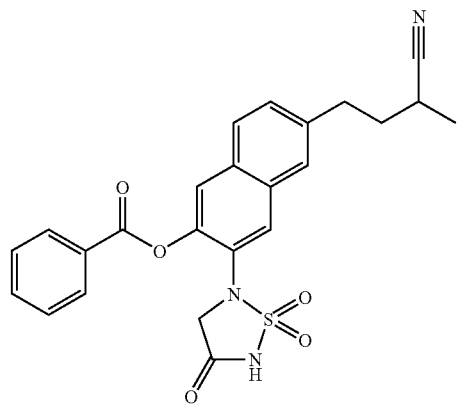

To a solution of 4-[6-hydroxy-7-(1,1,4-trioxo-1,2,5-thiadiazolidin-2-yl)-naphthalen-2-yl]-2-methylbutyronitrile (Example 9-3, 29 mg, 0.08 mmol) in DMF (0.6 mL) is added potassium t-butoxide (0.097 mL, 0.097 mmol) followed by benzoyl chloride. The reaction is stirred at RT until the reaction is completed. The reaction mixture is then purified by HPLC to give the title compound: Retention time 1.23 min (Method A); (M+H)⁺=462.

EXAMPLE 39

The following compounds are prepared analogously to Example 38 using 4-[6-hydroxy-7-(1,1,4-trioxo-1,2,5-thiadiazolidin-2-yl)-naphthalen-2-yl]-2-methylbutyronitrile (Example 9-3) and appropriate reagents.

| Example | Chemical Name | MS (m/z) | Retention time (min) Method |
|---|---|---|---|
| 39-1 | 2,2-Dimethylpropionic acid 6-(3-cyano-3-methylpropyl)-3-(1,1,4-trioxo-1,2,5-thiadiazolidin-2-yl)-naphthalen-2-yl ester | (M − H)⁻ = 442 | |

| Example | Chemical Name | MS (m/z) | Retention time (min) Method |
|---|---|---|---|
| 39-2 | Propionic acid 6-(3-cyano-3-methylpropyl)-3-(1,1,4-trioxo-1,2,5-thiadiazolidin-2-yl)-naphthalen-2-yl ester | (M − H)⁻ = 414 | |
| 39-3 | 2-Ethylbutyric acid 6-(3-cyano-3-methylpropyl)-3-(1,1,4-trioxo-1,2,5-thiadiazolidin-2-yl)-naphthalen-2-yl ester | (M − H)⁻ = 456 | 1.28 A |
| 39-4 | Hexanoic acid 6-(3-cyano-3-methylpropyl)-3-(1,1,4-trioxo-1,2,5-thiadiazolidin-2-yl)-naphthalen-2-yl ester | (M − H)⁻ = 456 | 1.29 A |
| 39-5 | 2-Acetoxy-benzoic acid 6-(3-cyano-3-methylpropyl)-3-(1,1,4-trioxo-1,2,5-thiadiazolidin-2-yl)-naphthalen-2-yl ester | (M − H)⁻ = 520 | 1.11 A |
| 39-6 | Pentanoic acid 6-(3-cyano-3-methylpropyl)-3-(1,1,4-trioxo-1,2,5-thiadiazolidin-2-yl)-naphthalen-2-yl ester | (M − H)⁻ = 442 | 0.38 A |
| 39-7 | Acetic acid 6-(3-cyano-3-methylpropyl)-3-(1,1,4-trioxo-1,2,5-thiadiazolidin-2-yl)-naphthalen-2-yl ester | (M − H)⁻ = 400 | |
| 39-8 | 3-Methylbenzoic acid 6-(3-cyano-3-methylpropyl)-3-(1,1,4-trioxo-1,2,5-thiadiazolidin-2-yl)-naphthalen-2-yl ester | (M − H)⁻ = 476 | 1.29 A |
| 39-9 | 2-Methylbenzoic acid 6-(3-cyano-3-methylpropyl)-3-(1,1,4-trioxo-1,2,5-thiadiazolidin-2-yl)-naphthalen-2-yl ester | (M − H)⁻ = 476 | 0.74 A |
| 39-10 | 4-Butylbenzoic acid 6-(3-cyano-3-methylpropyl)-3-(1,1,4-trioxo-1,2,5-thiadiazolidin-2-yl)-naphthalen-2-yl ester | (M − H)⁻ = 518 | |
| 39-11 | Cyclohexanecarboxylic acid 6-(3-cyano-3-methylpropyl)-3-(1,1,4-trioxo-1,2,5-thiadiazolidin-2-yl)-naphthalen-2-yl ester | (M − H)⁻ = 468 | 1.30 A |
| 39-12 | 4-tert-Butylbenzoic acid 6-(3-cyano-3-methylpropyl)-3-(1,1,4-trioxo-1,2,5-thiadiazolidin-2-yl)-naphthalen-2-yl ester | (M − H)⁻ = 518 | 1.45 A |

EXAMPLE 40

2,2-Dimethylpropionic acid 6-(3-cyanophenyl)-3-(1,1,4-trioxo-1,2,5-thiadiazolidin-2-yl)-naphthalen-2-yl ester

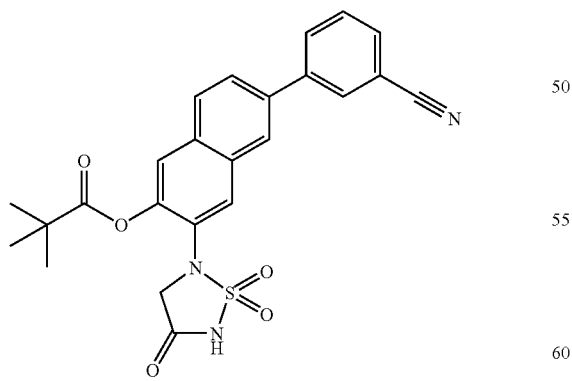

The title compound is prepared analogously to Example 38 from 3-[6-hydroxy-7-(1,1,4-trioxo-1,2,5-thiadiazolidin-2-yl)-naphthalen-2-yl]-benzonitrile (Example 5-13), using pivalic anhydride to replace benzoyl chloride (M−H)⁻=462.

EXAMPLE 41

The following compounds are prepared analogously to Example 38 from appropriate starting materials.

| Example | Chemical Name | MS (m/z) | Retention time (min) Method |
|---|---|---|---|
| 41-1 | Benzoic acid 6-(4-ethoxycarbonylbutyl)-3-(1,1,4-trioxo-1,2,5-thiadiazolidin-2-yl)-naphthalen-2-yl ester | $(M - H)^- = 509$ | 1.27 A |
| 41-2 | Benzoic acid 6-(3-methylbutyl)-3-(1,1,4-trioxo-1,2,5-thiadiazolidin-2-yl)-naphthalen-2-yl ester | $(M - H)^- = 451$ | |
| 41-3 | Benzoic acid 6-((E)-4-hydroxy-4-methylpent-1-enyl)-3-(1,1,4-trioxo-1,2,5-thiadiazolidin-2-yl)-naphthalen-2-yl ester | $(M - H)^- = 479$ | 1.19 |
| 41-4 | Benzoic acid 6-methyl-3-(1,1,4-trioxo-1,2,5-thiadiazolidin-2-yl)-naphthalen-2-yl ester | $(M - H)^- = 395$ | 1.17 |

EXAMPLE 42

Benzoic acid 6-(5-hydroxy-4,4-dimethylpentyl)-3-(1,1,4-trioxo-1,2,5-thiadiazolidin-2-yl)-naphthalen-2-yl ester

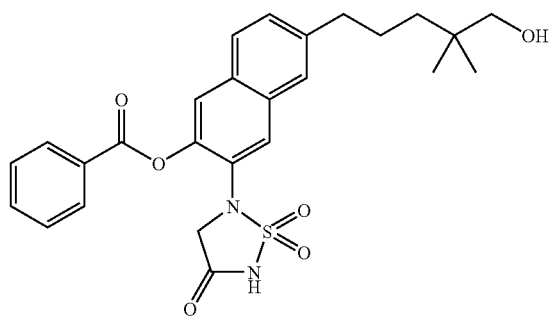

A. Benzoic acid 6-bromo-3-(1,1,4-trioxo-1,2,5-thiadiazolidin-2-yl)-naphthalen-2-yl ester To a solution of 5-(7-bromo-3-hydroxynaphthalen-2-yl)-1,1-dioxo-1,2,5-thiadiazolidin-3-one (3) (0.998 g, 2.8 mmol) in MeOH is added KHCO$_3$ (5.6 mL, 0.5M). To this salt in DMF (25 mL) at 0° C. is added potassium t-butoxide (2.94 mL, 1M). The reaction mixture is stirred for 1 min before benzoyl chloride (0.357 mL, 3.08 mmol) is added and the mixture is stirred for 1 min. Sat. NaHCO$_3$ solution is added and it is acidified with 1 N HCl solution. The mixture is extracted with EtOAc, washed with brine and dried with Na$_2$SO$_4$. The organic layer is concentrated to give the title compound.

B. 2,2-Dimethylpent-4-en-1-ol

To a solution of LAH (17.6 mL, 17.6 mmol, 1 M) in THF (2 mL) is added 2,2-dimethyl-4-pentenoic acid (1.61 mL, 11.7 mmol) at 0° C. The mixture is allowed to warm to RT and stirred for 2 h. The reaction mixture is then cooled to 0° C. and quenched with ice. The mixture is extracted with ether. The ether layer is dried with NaSO$_4$ and concentrated to afford the title compound as a yellow oil.

C. Benzoic acid 6-(5-hydroxy-4,4-dimethylpentyl)-3-(1,1,4-trioxo-1,2,5-thiadiazolidin-2-yl)-naphthalen-2-yl ester The title compound is prepared analogously to Example 8, step A, from benzoic acid 6-bromo-3-(1,1,4-trioxo-1,2,5-thiadiazolidin-2-yl)-naphthalen-2-yl ester and 2,2-dimethylpent-4-en-1-ol: Retention time=1.30 min (Method A); $(M-H)^-=495$.

EXAMPLE 43

5-[3-Hydroxy-7-(5-hydroxy-4,4-dimethylpentyl)-naphthalen-2-yl]-1,1-dioxo-1,2,5-thiadiazolidin-3-one

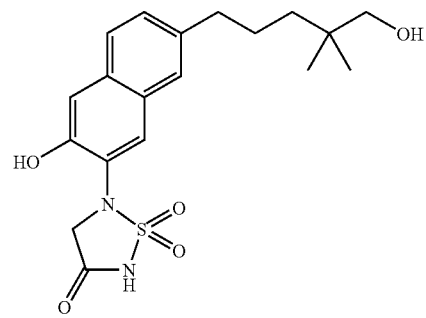

The title compound is prepared analogously to Example 11 from benzoic acid 6-(5-hydroxy-4,4-dimethylpentyl)-3-(1,1,4-trioxo-1,2,5-thiadiazolidin-2-yl)-naphthalen-2-yl ester and 1 N NaOH solution to replace KOH: Retention time=1.05 min (Method A); $(M-H)^-=391$.

EXAMPLE 44

5-(3-Hydroxy-5,6,7,8-tetrahydronapthalen-2-yl)-1,1-dioxo-1,2,5-thiadiazolidin-3-one

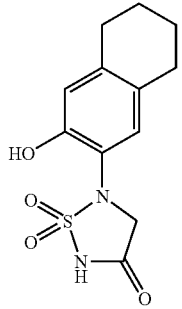

A. 1-Bromo-5,6,7,8-tetrahydronaphthalen-2-ol

To a solution of 5,6,7,8-tetrahydro-2-naphthol (2.50 g, 16.9 mmol) in DMF (5 mL), is added dropswise NBS (3.0 g, 16.9 mmol). The solution is stirred at room temperature for 18 h. The mixture is washed with water, extracted with $CH_2Cl_2$, dried over $MgSO_4$ and concentrated. The crude material is purified via Biotage, eluting with 5-40% EtOAc/hexanes to afford 1-bromo-5,6,7,8-tetrahydronaphthalen-2-ol.

B. 1-Bromo-3-nitro-5,6,7,8-tetrahydronaphthalen-2-ol

The title compound is prepared from 5,6,7,8-tetrahydronaphthalen-2-ol based on the procedure described in *J. Med. Chem.* 46, 1962-1979 (2003).

C. 6-Benzyloxy-5-bromo-7-nitro-1,2,3,4-tetrahydronaphthalene

6-Benzyloxy-5-bromo-7-nitro-1,2,3,4-tetrahydronaphthalene is prepared analogously to Example 1, step B.

D. 3-Benzyloxy-4-bromo-5,6,7,8-tetrahydronaphthalen-2-ylamine

To a solution of 6-benzyloxy-5-bromo-7-nitro-1,2,3,4-tetrahydronaphthalene (0.50 g, 1.38 mmol) in AcOH/EtOH (3:1, 20 mL), is added iron powder (0.50 g, 9.25 mmol). The mixture is heated at 100° C. for 2 h. The precipitate is filtered through Celite. The filtrate is concentrated, extracted with water and $CH_2Cl_2$, and filtered. The crude material is purified via Biotage, eluting with 0-20% EtOAc/hexanes, to afford 3-benzyloxy-4-bromo-5,6,7,8-tetrahydronaphthalen-2-ylamine: (M+H)=333, 334.

E. 5-(3-Hydroxy-5,6,7,8-tetrahydronapthalen-2-yl)-1,1-dioxo-1,2,5-thiadiazolidin-3-one 5-(3-Hydroxy-5,6,7,8-tetrahydronapthalen-2-yl)-1,1-dioxo-1,2,5-thiadiazolidin-3-one is prepared according to the general procedures outlined in Example 1, steps E-1: $^1$H NMR (MeOD) δ 7.18 (s, 1H), 6.74 (s, 1H), 4.58 (s, 2H), 2.79-2.82 (m, 4H), 1.88-1.91 (m, 4H).

EXAMPLE 45

5-(3,6-Dihydroxy-5,6,7,8-tetrahydronaphthalen-2-yl)-1,1-dioxo-1,2,5-thiadiazolidin-3-one

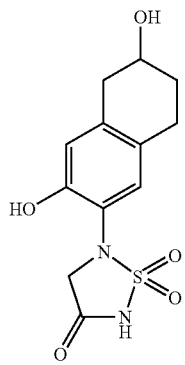

A. 7-Methoxy-1,2,3,4-tetrahydronaphthalen-2-ol

A solution of 7-methoxy-3,4-dihydro-1H-naphthalene (5.00 g, 28.4 mmol) in MeOH (5 mL) is added to a suspension of $NaBH_4$ (2.8 g, 74 mmol) in MeOH (40 mL) at −20° C. The mixture is stirred at −20° C. for 10 min. Solid $NH_4Cl$ is added, and the mixture is concentrated to remove most of the MeOH. The residue is partitioned between EtOAc and, sequentially, aq. $NH_4Cl$ and brine. The organic layer is dried over $MgSO_4$ and concentrated to afford 7-methoxy-1,2,3,4-tetrahydronaphthalen-2-ol as a red solid.

B. Acetic acid 7-methoxy-1,2,3,4-tetrahydronaphthalen-2-yl ester

7-Methoxy-1,2,3,4-tetrahydro-naphthalen-2-ol (4.48 g, from step A) is taken up in AcOH (15 mL) and cooled to 0° C. Concentrated sulfuric acid (10 drops) is added. The mixture is stirred at 0° C. for 20 min and then warmed to room temperature over 10 min. The mixture is partitioned between ice-cold 1 N NaOH and EtOAc. The organic layer is dried over $MgSO_4$ and concentrated to afford acetic acid 7-methoxy-1,2,3,4-tetrahydro-naphthalen-2-yl ester as a red solid: $^1$H NMR ($CDCl_3$) δ 7.01 (d, J=8.0 Hz, 1H), 6.71 (d, J=8.0 Hz, 1H), 6.60 (s, 1H), 5.19 (m, 1H), 3.77 (s, 3H), 3.08 (dd, J=16.0, 8.0 Hz, 1H), 2.90-2.70 (m, 3H), 2.05 (s, 3H), 2.05-1.88 (m, 2H).

C. Acetic acid 7-hydroxy-1,2,3,4-tetrahydronaphthalen-2-yl ester $BCl_3$ (1 M in DCM, 56 mL) is added to a mixture of acetic acid 7-methoxy-1,2,3,4-tetrahydro-naphthalen-2-yl ester (4.94 g, 22.5 mmol) and $Bu_4NI$ (10.8 g, 29.2 mmol) in DCM (112 mL) at −78° C. The mixture is stirred at −78° C. and then warmed to room temperature over 1 h. The mixture is partitioned between EtOAc and ice-cold brine. The organic layer is dried over $MgSO_4$, concentrated and chromatographed to afford acetic acid 7-hydroxy-1,2,3,4-tetrahydronaphthalen-2-yl ester as a yellow oil, which upon standing at room temperature becomes a solid: $^1$H NMR ($CDCl_3$) δ 6.96 (d, J=8.0 Hz, 1H), 6.64 (d, J=8.0 Hz, 1H), 6.55 (s, 1H), 5.18 (m, 1H), 5.00 (m, 1H), 3.05 (dd, J=16.0, 8.0 Hz, 1H), 2.90-2.72 (m, 3H), 2.06 (s, 3H), 2.06-1.89 (m, 2H).

D. Acetic acid 7-benzyloxy-1,2,3,4-tetrahydronaphthalen-2-yl ester

The title compound is prepared analogously to Example 1, step B.

E. Acetic acid 7-benzyloxy-6-nitro-1,2,3,4-tetrahydronaphthalen-2-yl ester

To a solution of acetic acid 7-benzyloxy-1,2,3,4-tetrahydronaphthalen-2-yl ester (5.77 g, 19.5 mmol) in AcOH (30 mL) is added a solution of 90% $HNO_3$ (3.0 mL, ca. 64 mmol) in AcOH (5 mL), copper(II) nitrate hemipentahydrate (3.71 g, 19.8 mmol) and conc. $H_2SO_4$ (3 drops) at room temperature. The mixture is stirred at room temperature for 1.5 h and partitioned between EtOAc and aq. KOH. The organic layer is dried over $MgSO_4$, concentrated and chromatographed to afford acetic acid 7-benzyloxy-6-nitro-1,2,3,4-tetrahydronaphthalen-2-yl ester with some impurities. Crystallization from DCM-hexanes yields a precipitate, which is quickly rinsed with $Et_2O$-hexanes to afford pure acetic acid 7-benzyloxy-6-nitro-1,2,3,4-tetrahydro-naphthalen-2-yl ester: $^1$H NMR ($CDCl_3$) δ 7.66 (s, 1H), 7.48-7.29 (m, 5H), 6.80 (s, 1H), 5.22-5.15 (m, 1H), 5.19 (s, 2H), 3.10 (dd, J=16.0, 8.0 Hz, 1H), 2.95-2.72 (m, 3H), 2.05 (s, 3H), 2.05-1.95 (m, 2H).

F. Acetic acid 6-amino-7-benzyloxy-1,2,3,4-tetrahydronaphthalen-2-yl ester

A mixture of acetic acid 7-benzyloxy-6-nitro-1,2,3,4-tetrahydronaphthalen-2-yl ester (1.01 g, 2.96 mmol) and 5% Pt/C (150 mg) in EtOAc (20 mL) is hydrogenated at 1 atm and at ambient temperature for 18 h. The mixture is filtered through Celite, and the filtrate is concentrated to give the title compound as an oil, which is used directly in the next step.

G. 5-(3,6-Dihydroxy-5,6,7,8-tetrahydro-naphthalen-2-yl)-1,1-dioxo-1,2,5-thiadiazolidin-3-one 5-(3,6-Dihydroxy-5,6,7,8-tetrahydronaphthalen-2-yl)-1,1-dioxo-1,2,5-thiadiazolidin-3-one is prepared analogously to Example 1, steps E to I: MS $(M-H)^-$=297, $(M+NH_4)^+$=316; $^1$H NMR (DMSO-$d_6$) δ 8.72 (s, 1H), 7.06 (s, 1H), 6.50 (s, 1H), 4.72 (d, J=4.0 Hz, 1H), 4.00 (s, 2H), 3.85 (m, 1H), 2.85-2.42 (m, 4H), 1.85 (m, 1H), 1.55 (m, 1H).

EXAMPLE 46

5-(3-Hydroxy-6-methoxy-5,6,7,8-tetrahydronaphthalen-2-yl)-1,1-dioxo-1,2,5-thiadiazolidin-3-one

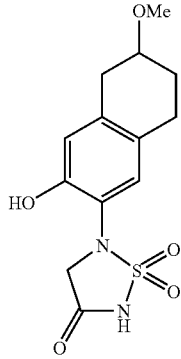

A. 6-(3-Benzyloxy-6-hydroxy-5,6,7,8-tetrahydronaphthalen-2-yl)-2-benzyloxymethyl-1,1-dioxo-1,2,5-thiadiazolidin-3-one A mixture of 5-(3-benzyloxy-6-hydroxy-5,6,7,8-tetrahydronaphthalen-2-yl)-1,1-dioxo-1,2,5-thiadiazolidin-3-one (158 mg, 0.40 mmol), intermediate from Example 45, chloromethoxymethylbenzene (0.068 mL, 0.49 mmol) and potassium carbonate (110 mg, 0.80 mmol) in DMF (4 mL) is stirred at RT for 18 h. The mixture is partitioned between EtOAc and 1 N HCl solution. The organic extract is dried with $MgSO_4$ and concentrated. The residue is purified by chromatography to give the title compound as an oil: $(M+NH_4)^+$=526.

B. 2-Benzyloxymethyl-5-(3-benzyloxy-6-oxo-5,6,7,8-tetrahydronaphthalen-2-yl)-1,1-dioxo-1,2,5-thiadiazolidin-3-one A solution of 5-(3-benzyloxy-6-hydroxy-5,6,7,8-tetrahydronaphthalen-2-yl)-2-benzyloxymethyl-1,1-dioxo-1,2,5-thiadiazolidin-3-one (87.6 mg, 0.17 mmol) in DCM (3 mL) is added to a suspension of Dess-Martin reagent (80 mg, 0.19 mmol) in DCM (1 mL). The mixture is stirred at RT for 30 min and filtered through Celite. The filtrate is concentrated and purified by chromatography to give the title compound as an oil: $^1$H NMR ($CDCl_3$) δ 2.54 (t, J=7 Hz, 2H), 3.01 (t, J=7 Hz, 2H), 3.55 (s, 2H), 4.44 (s, 2H), 4.57 (s, 2H), 5.03 (s, 2H), 5.8 (s, 2H), 6.82 (s, 1H), 7.28-7.36 (m, 11H); $(M+NH_4)^+$=524.

C. 5-(3-Hydroxy-6-methoxy-5,6,7,8-tetrahydronaphthalen-2-yl)-1,1-dioxo-1,2,5-thiadiazolidin-3-one A mixture of 2-benzyloxymethyl-5-(3-benzyloxy-6-oxo-5,6,7,8-tetrahydro-naphthalen-2-yl)-1,1-dioxo-1,2,5-thiadiazolidin-3-one (65.7 mg, 0.130 mmol) and 10% Pd/C (15 mg) in MeOH is hydrogenated at RT and at 1 atm for 18 h. The mixture is filtered through Celite and concentrated and purified via RP-HPLC to give the title compound, which is then converted to a potassium salt with the addition of 0.5N $KHCO_3$ (0.075 mL, 0.038 mmol): $^1$H NMR ($CD_3OD$) δ 1.74-1.79 (m, 1H), 2.00-2.06 (m, 1H), 2.62-2.70 (m, 2H), 2.75-2.90 (m, 1H), 2.97-3.01 (m, 1H), 3.39 (s, 3H), 3.60-3.68 (m, 1H), 4.29 (s, 2H), 6.59 (s, 1H), 7.12 (s, 1H); $(M-H)^-$=311.

EXAMPLE 47

5-(6-Ethoxy-3-hydroxy-5,6,7,8-tetrahydronaphthalen-2-yl)-1,1-dioxo-1,2,5-thiadiazolidin-3-one

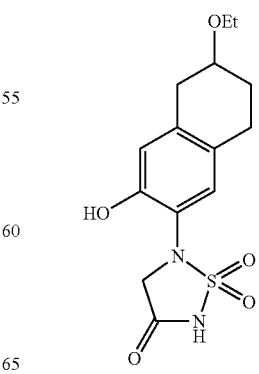

A. 2-Benzyl-5-(3-benzyloxy-6-hydroxy-5,6,7,8-tetrahydronaphthalen-2-yl)-1,1-dioxo-1,2,5-thiadiazolidin-3-one A mixture of 5-(3-benzyloxy-6-hydroxy-5,6,7,8-tetrahydronaphthalen-2-yl)-1,1-dioxo-1,2,5-thiadiazolidin-3-one (90 mg, 0.23 mmol) from preparing Example 45, benzyl bromide (0.033 mL, 0.28 mmol) and potassium carbonate (63 mg, 0.46 mmol) in DMF (2 mL) is stirred at RT for 18 h. The mixture is partitioned between EtOAc and 1 N HCl solution. The organic extract is dried with MgSO$_4$ and concentrated. The residue is purified to give the title compound as an oil: (M+NH$_4$)$^+$=478.

B. 2-Benzyl-5-(3-benzyloxy-6-oxo-5,6,7,8-tetrahydronaphthalen-2-yl)-1,1-dioxo-1,2,5-thiadiazolidin-3-one The title compound is prepared analogously to Example 46, step B.

C. 5-(6-Ethoxy-3-hydroxy-5,6,7,8-tetrahydronaphthalen-2-yl)-1,1-dioxo-1,2,5-thiadiazolidin-3-one The title compound is prepared analogously to Example 46, step C, using EtOH as a solvent to replace MeOH: $^1$H NMR (CD$_3$OD) δ 1.16-1.22 (m, 3H), 1.75-1.81 (m, 1H), 1.98-2.11 (m, 1H), 2.63-2.71 (m, 2H), 2.78-2.84 (m, 1H), 2.96-3.02 (m, 1H), 3.56-3.64 (m, 2H), 3.72-3.79 (m, 1H), 4.46 (s, 2H), 6.63 (s, 1H), 7.08 (s, 1H): (M−H)$^−$=325.

EXAMPLE 48

5-(3-Hydroxy-7-methyl-5,6,7,8-tetrahydronaphthalen-2-yl)-1,1-dioxo-1,2,5-thiadiazolidin-3-one

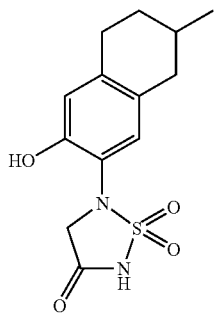

A. 6-Methoxy-2-methyl-3,4-dihydro-2H-naphthalen-1-one

A mixture of 6-methoxy-1-tetralone (5.0 g, 28.4 mmol), methyl iodide (20 mL, 262 mmol) and sodium hydride (60%, 5.5 g, 138 mmol, prewashed twice with hexanes) in toluene is heated at 80° C. for 3 days. The mixture is quenched carefully with water and is partitioned between EtOAc and brine. The organic extract is dried with MgSO$_4$, concentrated and purified via column chromatography to give the title compound as a light yellow oil: $^1$H NMR (CDCl$_3$) δ 1.27 (d, J=7 Hz, 3H), 1.83-1.89 (m, 1H), 2.10-2.15 (m, 1H), 2.51-2.60 (m, 1H), 2.90-3.00 (m, 2H), 3.85 (s, 3H), 6.68 (s, 1H), 6.81 (d, J=8.6 Hz, 1H), 8.01 (d, J=8.6 Hz, 1H).

B. 6-Methoxy-2-methyl-1,2,3,4-tetrahydronaphthalen-1-ol

To an ice-cooled solution of 6-methoxy-2-methyl-3,4-dihydro-2H-naphthalen-1-one (7.0 g, 36.8 mmol) in MeOH (120 mL) is added NaBH$_4$ (2.78 g, 73.6 mmol) portion wise and the mixture is stirred at RT for 20 min. Then the reaction is poured to 120 mL of water and extracted with ether. The organic phase is dried with MgSO$_4$, concentrated to give the title compound as a light yellow oil and it is used in the next step without purification.

C. 6-Methoxy-2-methyl-1,2,3,4-tetrahydronaphthalene

To a solution of 6-methoxy-2-methyl-1,2,3,4-tetrahydronaphthalen-1-ol (8.24 g) and triethylsilane (9.2 mL, 74 mmol) in DCM (100 mL) at 0° C. is added boron trifluoride-diethyl etherate (17.6 mL, 110 mmol) drop wise. After stirring for 10 min, the mixture is warmed to RT and stirred for 30 min. 10% K$_2$CO$_3$ solution is added and it is extracted with EtOAc. The organic layer is washed with brine, dried with MgSO$_4$ and concentrated to give the title compound as a yellow oil, which is then used in the next step without purification.

D. 6-Methyl-5,6,7,8-tetrahydronaphthalen-2-ol

The title compound is prepared analogously to Example 45, step C.

E. 1-Bromo-6-methyl-5,6,7,8-tetrahydronaphthalen-2-ol

The title compound is prepared analogously to Example 44, step A.

F. 1-Bromo-6-methyl-3-nitro-5,6,7,8-tetrahydronaphthalen-2-ol

The title compound is prepared analogously to Example 44, step B.

G. 6-Benzyloxy-5-bromo-2-methyl-7-nitro-1,2,3,4-tetrahydronaphthalene

The title compound is prepared analogously to Example 1, step B.

H. 3-Benzyloxy-4-bromo-7-methyl-5,6,7,8-tetrahydronaphthalen-2-ylamine

The title compound is prepared analogously to Example 45, step F.

I. 5-(3-Hydroxy-7-methyl-5,6,7,8-tetrahydronaphthalen-2-yl)-1,1-dioxo-1,2,5-thiadiazolidin-3-one The title compound is prepared according to the general procedure outlined in Example 1, steps E-1, except using 4M HCl in dioxane to replace TFA for the removal of Boc protecting group in the step of G: $^1$H NMR (CD$_3$OD) δ 1.04 (d, J=7 Hz, 3H), 1.29-1.39 (m, 1H), 1.70-1.93 (m, 2H), 2.16-2.31 (m, 1H), 2.68-2.71 (m, 3H), 4.43 (s, 2H), 6.65 (s, 1H), 7.04 (s, 1H); (M−H)$^−$=295.

EXAMPLE 49

5-(3-Hydroxy-7,7-dimethyl-5,6,7,8-tetrahydronaphthalen-2-yl)-1,1-dioxo-1,2,5-thiadiazolidin-3-one

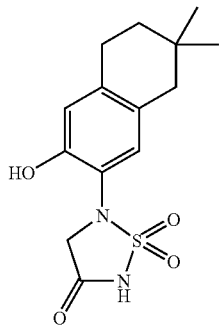

A. 6-Methoxy-2,2-dimethyl-3,4-dihydro-2H-naphthalen-1-one

A mixture of 6-methoxy-1-tetralone (5.0 g, 28.4 mmol), methyl iodide (20 mL, 262 mmol) and sodium hydride (60%, 5.5 g, 138 mmol, prewashed twice with hexanes) in toluene is heated at 80° C. for 3 days. The mixture is quenched carefully with water and is partitioned between EtOAc and brine. The organic extract is dried with $MgSO_4$, concentrated and purified via column chromatography to give the title compound as a light yellow oil: $^1$H NMR ($CDCl_3$) δ 1.26 (s, 6H), 1.96 (t, J=7 Hz, 2H), 2.94 (t, J=8 Hz, 2H), 3.85 (s, 3H), 6.66 (s, 1H), 6.82 (d, J=8.6 Hz, 1H), 8.01 (d, J=8.6 Hz, 1H).

B. 5-(3-Hydroxy-7,7-dimethyl-5,6,7,8-tetrahydronaphthalen-2-yl)-1,1-dioxo-1,2,5-thiadiazolidin-3-one The title compound is prepared analogously to Example 48, steps B-I: $^1$H NMR ($CD_3OD$) δ 0.85 (s, 6H), 1.42 (m, 2H), 2.31 (s, 2H), 2.62 (t, J=7 Hz, 2H), 4.35 (s, 2H), 6.53 (s, 1H), 6.91 (s, 1H); (M−H)⁻=309.

EXAMPLE 50

5-(3-Hydroxy-7-trifluoromethyl-5,6,7,8-tetrahydronaphthalen-2-yl)-1,1-dioxo-1,2,5-thiadiazolidin-3-one

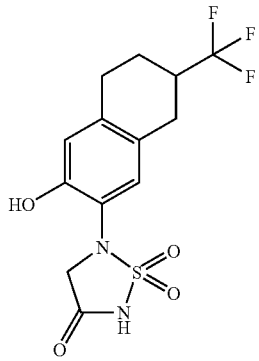

A. (6-Methoxy-3,4-dihydronaphthalen-1-yloxy)-trimethylsilane

To a solution of diisopropylamine (2.42 mL, 17.1 mmol) in THF (50 mL) at 0° C. is added n-BuLi (6.84 mL, 17.1 mmol, 2.5 M in hexane) dropwise. After 40 min, 6-methoxy-1-tetralone (3.0 g, 17.1 mmol) in THF (15 mL) is added at −78° C. It is then stirred at −78° C. for 2.5 h before chloro trimethylsilane (3.2 mL, 25.7 mmol) is added. It is then warmed to RT and stirred for 18 h. Water is added and the reaction mixture is extracted with EtOAc, washed with sat. $NH_4Cl$ solution, dried with $MgSO_4$ and concentrated to give the title compound as a yellow oil. It is used in the next step without purification.

B. 6-Methoxy-2-trifluoromethyl-3,4-dihydro-2H-naphthalen-1-one

To a solution of (6-methoxy-3,4-dihydronaphthalen-1-yloxy)-trimethylsilane (3.00 g, from step A) and 5-trifluoromethyldibenzothiophenium tetrafluoroborate (5.6 g, 16.5 mmol) in DMF (20 mL) is added slowly tetrabutylammonium difluorotriphenylstannate (7.0 g, 11.1 mmol) in DMF (40 mL) by a dropping funnel. After the addition is finished, the suspension is stirred at RT for 72 h. DMF is then removed under vacuum. Water and EtOAc are added. The organic layer is dried with $MgSO_4$, concentrated and purified to give the title compound as a light yellow oil: $^1$H NMR ($CDCl_3$) δ 2.24-2.31 (m, 1H), 2.44-2.50 (m, 1H), 3.01-3.07 (m, 2H), 3.20-3.25 (m, 1H), 3.87 (s, 3H), 6.70 (d, J=2.5 Hz, 1H), 6.86 (dd, J=2.52, 9 Hz, 1H), 8.04 (d, J=9 Hz, 1H).

C. 5-(3-Hydroxy-7-trifluoromethyl-5,6,7,8-tetrahydronaphthalen-2-yl)-1,1-dioxo-1,2,5-thiadiazolidin-3-one The title compound is prepared analogously to Example 48, steps B-I: $^1$H NMR ($CD_3OD$) δ1.62-1.68 (m, 1H), 2.11-2.15 (m, 1H), 2.53-2.54 (m, 1H), 2.68-3.90 (m, 4H), 4.29 (s, 2H), 6.65 (s, 1H), 7.19 (s, 1H); (M−H)⁻=349.

EXAMPLE 51

5-(3-Hydroxy-7-isopropyl-5,6,7,8-tetrahydronaphthalen-2-yl)-1,1-dioxo-1,2,5-thiadiazolidin-3-one

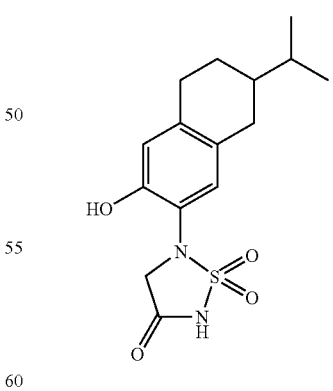

A. 6-Hydroxy-1,2,3,4-tetrahydronaphthalene-2-carboxylic acid ethyl ester

The title compound is prepared as a white solid from 6-methoxy-1,2,3,4-tetrahydronaphthalene-2-carboxylic acid ethyl ester (JP 09255625) analogously to Example 45, step C:

¹H NMR (CDCl₃) δ1.28 (t, J=7 Hz, 3H), 1.78-1.86 (m, 1H), 2.14-2.22 (m, 1H), 2.65-2.72 (m, 1H), 2.76-2.83 (m, 2H), 2.90-2.95 (m, 2H), 4.17 (q, J=7 Hz, 2H), 4.78 (br, 1H), 6.56 (s, 1H), 6.60 (d, J=8 Hz, 1H), 6.95 (d, J=8 Hz, 1H); (M−H)⁻=219.

B. 6-Benzyloxy-1,2,3,4-tetrahydronaphthalene-2-carboxylic acid ethyl ester

The title compound is prepared as a white solid from 6-hydroxy-1,2,3,4-tetrahydronaphthalene-2-carboxylic acid ethyl ester analogously to Example 1, step B: ¹H NMR (CDCl₃) δ1.28 (t, J=7 Hz, 3H), 1.78-1.86 (m, 1H), 2.14-2.22 (m, 1H), 2.65-2.72 (m, 1H), 2.76-2.83 (m, 2H), 2.90-2.95 (m, 2H), 4.17 (q, J=7 Hz, 2H), 5.02 (s, 2H), 6.70 (d, J=2.5 Hz, 1H) 6.76 (dd, J=2.5, 8 Hz, 1H), 7.01 (d, J=8 Hz, 1H), 7.31-7.43 (m, 5H); (M+H)⁺=311.

C. 2-(6-Benzyloxy-1,2,3,4-tetrahydronaphthalen-2-yl)-propan-2-ol

To a solution of 6-benzyloxy-1,2,3,4-tetrahydronaphthalene-2-carboxylic acid ethyl ester (3.50 g, 11.3 mmol) in THF (30 mL) at −78° C. is added methylmagnesium bromide (3M in diethyl ether, 11 mL, 33 mmol) and the mixture is stirred at RT for 1 h. The reaction is not complete and MeLi (1.6 M in diethyl ether, 16 mL, 10 mmol) is added at RT. After 30 min at RT, the reaction is shown to be complete by TLC analysis. The mixture is carefully quenched with water and partitioned between EtOAc and aqueous NH₄Cl. The organic extract is dried with MgSO₄ and concentrated to give the title compound, which is used directly in the next step.

D. 6-Benzyloxy-2-isopropenyl-1,2,3,4-tetrahydronaphthalene and 6-Benzyloxy-2-isopropylidene-1,2,3,4-tetrahydronaphthalene To a solution of 2-(6-benzyloxy-1,2,3,4-tetrahydronaphthalen-2-yl)-propan-2-ol from step C in pyridine (20 mL) is added thionyl chloride (1.5 mL, 20.5 mmol) at 0° C. and the mixture is stirred at RT for 1 h. The mixture is then poured to ice slowly and partitioned between EtOAc and 3M HCl solution. The organic extract is dried with MgSO₄, concentrated and purified by chromatography to give a mixture of the title compounds as an oil; (M+H)⁺=279.

E. 6-Isopropyl-5,6,7,8-tetrahydronaphthalen-2-ol

To the mixture of 6-benzyloxy-2-isopropenyl-1,2,3,4-tetrahydronaphthalene and 6-benzyloxy-2-isopropylidene-1,2,3,4-tetrahydronaphthalene (2.37 g, crude) in EtOH (30 mL) is added 10% Pd/C (550 mg) and it is hydrogenated at RT and at 1 atm for 24 h. The mixture is filtered through Celite, and the filtrate is concentrated and purified to give the title compound: ¹H NMR (CDCl₃) δ 0.95 (d, J=6 Hz, 6H), 1.31-1.41 (m, 1H), 1.42-1.46 (m, 1H), 1.56-1.62 (m, 1H), 1.87-1.92 (m, 1H), 2.39-2.45 (m, 1H), 2.69-2.77 (m, 3H), 4.43 (s, 2H), 6.55 (d, J=2.5 Hz, 1H), 6.58 (d, J=2.5, 8 Hz, 1H), 6.93 (d, J=8 Hz, 1H), 7.31-7.43 (m, 5H); (M−H)⁻=189.

F. 5-(3-Hydroxy-7-isopropyl-5,6,7,8-tetrahydronaphthalen-2-yl)-1,1-dioxo 1,2,5-thiadiazolidin-3-one The title compound as a potassium salt is prepared as a white solid analogously to Example 48, steps E-I from 6-isopropyl-5,6,7,8-tetrahydronaphthalen-2-ol: ¹H NMR (DMSO-d₆) δ 0.92 (dd, J=1.8, 6.8 Hz, 6H), 1.24-1.30 (m, 1H), 1.65-1.82 (m, 1H), 1.51-1.56 (m, 1H), 1.82-1.90 (m, 1H), 2.85-2.33 (m, 1H), 2.59-2.67 (m, 3H), 3.99 (q, J=13 Hz, 2H), 6.52 (s, 1H), 7.70 (s, 1H), 8.63 (s, 1H); (M−H)⁻=323.

EXAMPLE 52

5-(7-Ethyl-3-hydroxy-5,6,7,8-tetrahydronaphthalen-2-yl)-1,1-dioxo-1,2,5-thiadiazolidin-3-one

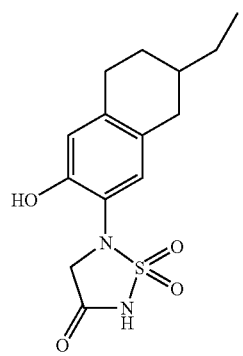

A.
2-Ethyl-6-methoxy-3,4-dihydro-2H-naphthalen-1-one

The title compound is prepared analogously to Example 48, step A using ethyl iodide to replace methyl iodide: ¹H NMR (CDCl₃) δ 0.92 (t, J=7 Hz, 3H), 1.47-1.52 (m, 1H), 1.77-1.92 (m, 2H), 2.10-2.18 (m, 1H), 2.26-2.31 (m, 1H), 2.86-2.92 (m, 2H), 3.78 (s, 3H), 6.60 (d, J=2.5 Hz, 1H), 6.74 (dd, J=2.5, 8.8 Hz, 1H), 7.03 (d, J=8.8 Hz).

B. 3-Ethyl-7-methoxy-1,2-dihydronaphthalene

To a solution of 2-ethyl-6-methoxy-3,4-dihydro-2H-naphthalen-1-one (6.10 g, 29.9 mmol) in MeOH (70 mL) at 0° C. is added NaBH₄ slowly and the mixture is stirred at RT for 30 min. Then 2M HCl solution (200 mL) is added and the mixture is stirred for 10 min before it is extracted with EtOAc and concentrated. The residue is purified to give the title compound as a clear oil: (M+H)⁺=189.

C. 2-Ethyl-6-methoxy-1,2,3,4-tetrahydronaphthalene

To a solution of 3-ethyl-7-methoxy-1,2-dihydronaphthalene (2.6 g, 13.8 mmol) in MeOH (20 mL) is added 10% Pd/C (200 mg) and the mixture is stirred at 1 atm for 18 h. The mixture is filtered through Celite, and the filtrate is concentrated to give the title compound: ¹H NMR (CDCl₃) δ 0.87 (t, J=7 Hz, 3H), 1.19-1.32 (m, 3H), 1.49-1.50 (m, 1H), 1.80-1.82 (m, 1H), 2.19-2.23 (m, 1H), 2.72-2.67 (m, 3H), 3.67 (s, 3H), 6.52 (d, J=2.5 Hz, 1H), 6.57 (dd, J=2.5, 8 Hz, 1H), 6.83 (d, J=8 Hz, 1H).

D. 6-Ethyl-5,6,7,8-tetrahydronaphthalen-2-ol

The title compound is prepared analogously to Example 45, step C from 2-ethyl-6-methoxy-1,2,3,4-tetrahydronaphthalene: ¹H NMR (CDCl₃) δ 0.89 (t, J=7 Hz, 3H), 1.24-1.34 (m, 3H), 1.49-1.53 (m, 1H), 1.81-1.86 (m, 1H), 2.20-2.26 (m, 1H), 2.66-2.69 (m, 3H), 6.48 (d, J=2.5 Hz, 1H), 6.52 (dd, J=2.5, 8 Hz, 1H), 6.85 (d, J=8 Hz, 1H).

E. 6-Ethyl-3-nitro-5,6,7,8-tetrahydronaphthalen-2-ol

To a solution of HNO$_3$ (65%, 1.05 mL, 23.0 mmol) in AcOH (10 mL) at 0° C. is added 6-ethyl-5,6,7,8-tetrahydronaphthalen-2-ol (2.02 g, 11.5 mmol) in AcOH (33 mL) dropwise. It is allowed to warm to ambient temperature and stirred for 1.5 h and then at 40° C. until starting material is completely consumed. Water is added, followed by EtOAc. The organic layer is concentrated and purified by column chromatography to give the title compound as a yellow oil: $^1$H NMR (CDCl$_3$) δ 0.91 (t, J=7 Hz, 3H), 1.28-1.36 (m, 3H), 1.51-1.56 (m, 1H), 1.85-1.90 (m, 1H), 2.24-2.31 (m, 1H), 2.72-2.64 (m, 3H), 6.77 (s, 1H), 7.73 (s, 1H), 10.29 (s, 1H).

F. 6-Benzyloxy-2-ethyl-7-nitro-1,2,3,4-tetrahydronaphthalene

The title compound is prepared analogously to Example 1, step B.

G. 3-Benzyloxy-7-ethyl-5,6,7,8-tetrahydronaphthalen-2-ylamine

To a solution of 6-benzyloxy-2-ethyl-7-nitro-1,2,3,4-tetrahydronaphthalene (490 mg, 1.57 mmol) is added 5% Pt/C (680 mg) and stirred under hydrogen atmosphere (1 atm) for 18 h. It is then filtered through Celite and the filtrate is concentrated. The residue is purified by column chromatography to give the title compound as a brown solid.

H. 5-(7-Ethyl-3-hydroxy-5,6,7,8-tetrahydronaphthalen-2-yl)-1,1-dioxo-1,2,5-thiadiazolidin-3-one The title compound is prepared as a white solid analogously to Example 1, steps E-I, from 3-benzyloxy-7-ethyl-5,6,7,8-tetrahydronaphthalen-2-ylamine: $^1$H NMR (CD$_3$OD) δ 0.96 (t, J=7 Hz, 3H), 1.28-1.41 (m, 3H), 1.53-1.58 (m, 1H), 1.92-1.97 (m, 1H), 2.25-2.32 (m, 1H), 2.72-2.80 (m, 3H), 4.24 (s, 2H), 6.57 (s, 1H), 7.07 (s, 1H); (M−H)$^-$=309.

EXAMPLE 53

5-(7,7-Diethyl-3-hydroxy-5,6,7,8-tetrahydronaphthalen-2-yl)-1,1-dioxo-1,2,5-thiadiazolidin-3-one

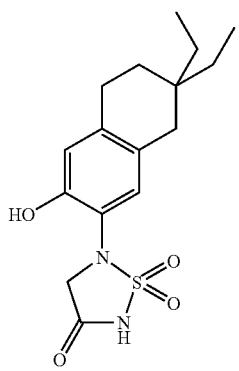

A. 2,2-Diethyl-6-methoxy-3,4-dihydro-2H-naphthalen-1-one

The title compound is prepared analogously to Example 49, step A, using ethyl iodide to replace methyl iodide.

B. 5-(7,7-Diethyl-3-hydroxy-5,6,7,8-tetrahydronaphthalen-2-yl)-1,1-dioxo-1,2,5-thiadiazolidin-3-one The title compound is prepared as a potassium salt analogously to Example 48, steps B-I: $^1$H NMR (CD$_3$OD) δ 0.83-0.86 (t, J=7 Hz, 6H), 1.26-1.39 (m, 4H), 1.54-1.58 (t, J=6.8 Hz, 2H), 2.41 (s, 2H), 2.65-2.70 (m, 2H), 4.30 (s, 2H), 6.58 (s, 1H), 7.07 (s, 1H); (M−H)$^-$=337.

EXAMPLE 54

5-(3-Hydroxy-7,7-dipropyl-5,6,7,8-tetrahydronaphthalen-2-yl)-1,1-dioxo-1,2,5-thiadiazolidin-3-one

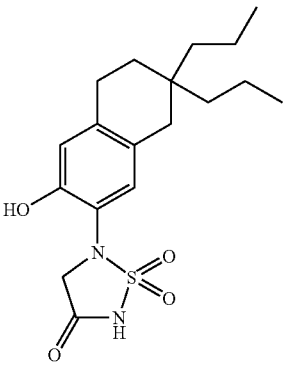

A. 2,2-Diallyl-6-methoxy-3,4-dihydro-2H-naphthalen-1-one

The title compound is prepared analogously to Example 49, step A using allyl bromide to replace methyl iodide.

B. 2,2-Diallyl-6-methoxy-1,2,3,4-tetrahydronaphthalene

The title compound is prepared analogously to Example 48, steps B-C.

C. 5-(3-Hydroxy-7,7-dipropyl-5,6,7,8-tetrahydronaphthalen-2-yl)-1,1-dioxo-1,2,5-thiadiazolidin-3-one The title compound is prepared analogously to Example 52, steps C-H: $^1$H NMR (CD$_3$OD) δ 0.85-0.88 (m, 6H), 1.15-1.32 (m, 8H), 1.52 (t, J=6 Hz, 2H), 2.41 (s, 2H), 2.62-2.65 (m, 2H), 4.25 (s, 2H), 6.65 (s, 1H), 7.05 (s, 1H); (M−H)$^-$=365.

EXAMPLE 55

5-(6'-Hydroxy-3',4'-dihydro-1'H-spiro[cyclopentane-1,2'-naphthalen]-7'-yl)1,2,5-thiadiazolidin-3-one 1,1-dioxide

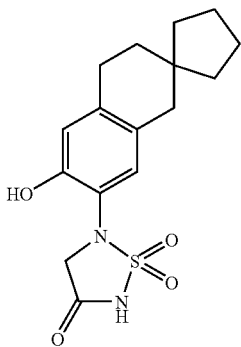

A. 3',4'-Dihydro-1'H-spiro[cyclopent-3-ene-1,2'-naphthalen]-6'-ol

To a solution of 2,2-diallyl-6-methoxy-1,2,3,4-tetrahydronaphthalene (4.00 g, 16.5 mmol) obtained during the preparation of Example 54 in DCM (20 mL) is added Grubbs catalyst (1st generation, 1.4 g, 1.7 mmol) and the purple mixture is stirred at RT for 18 h. The mixture is concentrated and purified to give the title compound as a brown oil: $^1$H NMR (CDCl$_3$) δ 1.78 (t, J=7 Hz, 2H), 2.13-2.18 (m, 2H), 2.23-2.28 (m, 2H), 2.65 (s, 2H), 2.85 (t, J=7 Hz, 2H), 3.77 (s, 3H), 5.65 (s, 2H), 6.63 (d, J=2.5, 1H), 6.66 (dd, J=2.5, 8 Hz, 1H), 6.93 (d, J=8 Hz, 1H).

B. 5-(6'-Hydroxy-3',4'-dihydro-1'H-spiro[cyclopentane-1,2'-naphthalen]-7'-yl)1,2,5-thiadiazolidin-3-one 1,1-dioxide The title compound is prepared analogously to Example 52, steps C-H: $^1$H NMR (CD$_3$OD) δ 1.43-1.46 (m, 4H), 1.66-1.71 (m, 6H), 2.53 (s, 2H), 2.73-2.76 (m, 2H), 4.28 (s, 2H), 6.61 (s, 1H), 7.07 (s, 1H); (M–H)$^-$=335.

EXAMPLE 56

5-((S)-7-Ethyl-3-hydroxy-5,6,7,8-tetrahydronaphthalen-2-yl)-1,1-dioxo-1,2,5-thiadiazolidin-3-one

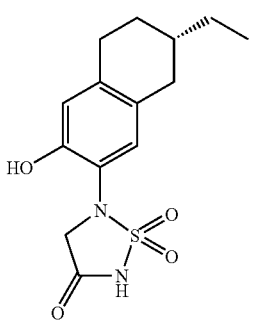

A. (4-Methoxy-2-vinylphenyl)-methanol

The title compound is prepared analogously to Example 45, step A, from 4-methoxy-2-vinyl-benzaldehyde (J. Org. Chem., 1997, 62, page 7850-7857): $^1$H NMR (CDCl$_3$) δ 3.83 (s, 3H), 4.69 (d, J=5.6 Hz, 2H), 5.36 (dd, J=1, 11 Hz, 1H), 5.70 (dd, J=1, 17 Hz, 1H), 6.81 (dd, J=3, 8 Hz, 1H), 7.03 (d, J=2 Hz, 1H), 7.06 (dd, J=11, 17 Hz, 1H), 7.25 (d, J=8 Hz, 1H).

B. 1-Bromomethyl-4-methoxy-2-vinylbenzene

To a solution of (4-methoxy-2-vinylphenyl)-methanol (7.90 g, 48.2 mmol) in diethyl ether (100 mL) at 0° C. is added PBr$_3$ (5.0 mL, 53 mmol) over 1 min. Water is added carefully to destroy excess PBr$_3$. The mixture is partitioned carefully between EtOAc and NaHCO$_3$ (plus a small amount of KOH to adjust pH to 7~8). The organic extract is dried with MgSO$_4$ and concentrated to give the title compound and it is used directly in the next step: $^1$H NMR (CDCl$_3$) δ 3.83 (s, 3H), 4.57 (s, 2H), 5.44 (dd, J=1, 11 Hz, 1H), 5.74 (dd, J=1, 17 Hz, 1H), 6.81 (dd, J=3, 8 Hz, 1H), 7.03 (d, J=2 Hz, 1H), 7.06 (dd, J=11, 17 Hz, 1H), 7.25 (d, J=8 Hz, 1H).

C. (4S,5R)-3-[(R)-2-(4-Methoxy-2-vinylbenzyl)-butyryl]-4-methyl-5-phenyloxazolidin-2-one n-BuLi (21.3 mL, 53.3 mmol, 2.5 M in hexane) is added to a solution of diisopropylamine (8.2 mL, 58.1 mmol) in THF (150 mL) at −78° C. and the mixture is stirred at −78° C. for 10 min. A solution of (4S,5R)-3-butyryl-4-methyl-5-phenyloxazolidin-2-one (11.99 g, 48.5 mmol, prepared from (4S, 5R)-4-methyl-5-phenyloxazolidin-2-one based on the procedure described in Tetrahedron Letters, 1986, 27, page 3311-3314) in THF (50 mL) is added. The mixture is stirred at −78° C. for 30 min. Finally, a solution of 1-bromomethyl-4-methoxy-2-vinylbenzene (11.1 g, crude) in THF (30 mL) is added. The mixture is stirred at −78° C. for 10 min and warmed to RT over 1 h and is continued to be stirred at RT for 15 h. The mixture is partitioned between EtOAc and sat. NH$_4$Cl solution. The organic extract is dried with MgSO$_4$, concentrated and purified by chromatography to give the title compound as an oil: $^1$H NMR (CDCl$_3$) δ 0.68 (d, J=7 Hz, 3H), 0.95 (t, J=7 Hz, 3H), 1.52-1.59 (m, 1H), 1.73-1.79 (m, 1H), 2.80-2.85 (m, 1H), 2.98-3.04 (m, 1H), 3.78 (s, 3H), 4.14-4.20 (m, 1H), 4.70-4.75 (m, 1H), 5.34 (dd, J=1.3, 11 Hz, 1H), 5.57 (d, J=7.3 Hz, 1H), 5.63 (dd, J=1.3, 17 Hz, 1H), 6.72 (dd, J=2.5, 8 Hz, 1H), 6.99 (d, J=2.8 Hz, 1H), 7.04 (dd, J=11, 17 Hz, 1H), 7.13 (d, J=8 Hz, 1H), 7.21-7.24 (m, 2H), 7.35-7.40 (m, 3H).

D. (R)-2-(4-Methoxy-2-vinylbenzyl)-butan-1-ol

LiBH$_4$ (1.66 g, 76.1 mmol) is added to a solution of (4S, 5R)-3-[(R)-2-(4-methoxy-2-vinylbenzyl)-butyryl]-4-methyl-5-phenyloxazolidin-2-one (13.1 g, 33.3 mmol) in THF/MeOH (132 mL, 10:1, v/v) at 0° C. After 5 min at 0° C., the mixture is stirred at RT for 30 min. Water is carefully added, followed by addition of aq. NH$_4$Cl solution. The mixture is partitioned between EtOAc and water layer. The organic extract is dried with MgSO$_4$, concentrated and purified by chromatography to give the title compound as an oil: $^1$H NMR (CDCl$_3$) δ 0.94 (t, J=7.6 Hz, 3H), 1.36-1.43 (m, 2H), 1.62-1.68 (m, 1H), 2.59-2.69 (m, 2H), 3.49-3.55 (m, 2H), 3.81 (s, 3H), 5.30 (dd, J=1, 11 Hz, 1H), 5.64 (dd, J=1, 17 Hz, 1H), 6.76 (dd, J=3, 8 Hz, 1H), 6.99 (dd, J=11, 17 Hz, 1H), 7.02 (d, J=3 Hz, 1H), 7.06 (d, J=8 Hz, 1H).

E. (R)-2-(4-Methoxy-2-vinylbenzyl)-butyraldehyde

DMSO (4.9 mL, 68.8 mml) is added to a solution of oxalyl chloride (4.5 mL, 51.6 mmol) in dry DCM (100 mL) at −78° C. and the mixture is stirred at −78° C. for 10 min. A solution of (R)-2-(4-methoxy-2-vinylbenzyl)-butan-1-ol (5.70, 25.9 mmol) in DCM (30 mL) is added. The mixture is stirred at −78° C. for 15 min and then at −40~−30° C. for 1 h. Triethylamine (18 mL, 129 mmol) is added slowly. The mixture is stirred at −10~0° C. for 15 min. The mixture is partitioned between DCM and aq. NH₄Cl. The organic extract is dried with MgSO₄ and concentrated to give the title compound as an orange oil.

F. 1-((R)-2-Ethyl-but-3-enyl)-4-methoxy-2-vinylbenzene

MeLi (32 mL, 51 mmol, 1.6 M in diethyl ether) is added to a suspension of methyltriphenylphosphonium bromide (27.8 g, 77.8 mmol) in THF (100 mL) at 0° C. The mixture is stirred at 0° C. for 30 min. Then a solution of (R)-2-(4-Methoxy-2-vinylbenzyl)-butyraldehyde (6.12 g) in THF (50 mL) is added. The mixture is stirred at 0° C. for 1 h. The mixture is partitioned between EtOAc and aq. NH₄Cl. The organic extract is dried with MgSO₄, concentrated and purified to give the title compound as an oil: ¹H NMR (CDCl₃) δ 0.85 (t, J=7.3 Hz, 3H), 1.23-1.28 (m, 1H), 1.42-1.47 (m, 1H), 2.09-2.14 (m, 1H), 2.56-2.69 (m, 2H), 3.81 (s, 3H), 4.85 (d, J=17 Hz, 1H), 4.93 (dd, J=2, 10 Hz, 1H), 5.27 (dd, J=1, 11 Hz, 1H), 5.50-5.65 (m, 2H), 6.74 (dd, J=3, 8 Hz, 1H), 6.94 (dd, J=11, 17 Hz, 1H), 6.99 (d, J=8 Hz, 1H), 7.02 (d, J=3 Hz, 1H).

G. (R)-2-Ethyl-6-methoxy-1,2-dihydronaphthalene

The title compound is prepared analogously to Example 55, step A from 1-((R)-2-Ethyl-but-3-enyl)-4-methoxy-2-vinylbenzene: ¹H NMR (CDCl₃) δ 0.96 (t, J=7.6 Hz, 3H), 1.41-1.54 (m, 2H), 2.30-2.35 (m, 1H), 2.49-2.55 (m, 1H), 2.76-2.82 (m, 1H), 3.78 (s, 3H), 5.94 (dd, J=3.5, 10 Hz, 1H), 6.38 (dd, J=2, 10 Hz, 1H), 6.60 (d, J=3 Hz, 0.1H), 6.66 (dd, J=3, 8 Hz, 1H), 7.00 (d, J=8 Hz, 1H).

H. (S)-2-Ethyl-6-methoxy-1,2,3,4-tetrahydronaphthalene

The title compound is prepared analogously to Example 55, step B, from (R)-2-Ethyl-6-methoxy-1,2-dihydronaphthalene: ¹H NMR (CDCl₃) δ 0.97 (t, J=7.6 Hz, 3H), 1.35-1.42 (m, 3H), 1.56-1.62 (m, 1H), 1.89-1.94 (m, 1H), 2.29-2.35 (m, 1H), 2.77-2.82 (m, 3H), 3.76 (s, 3H), 6.61 (d, J=3 Hz, 1H), 6.67 (dd, J=3, 8 Hz, 1H), 6.97 (d, J=8 Hz, 1H).

I. 5-((S)-7-Ethyl-3-hydroxy-5,6,7,8-tetrahydronaphthalen-2-yl)-1,1-dioxo-1,2,5-thiadiazolidin-3-one The title compound as a potassium salt is prepared analogously to Example 48, steps D to I: ¹H NMR (CD₃OD) δ 0.98 (t, J=7.6 Hz, 3H), 1.29-1.42 (m, 1H), 1.50-1.62 (m, 1H), 1.80-1.95 (m, 1H), 2.24-2.31 (m, 1H), 2.69-2.79 (m, 3H), 4.28 (s, 2H), 6.58 (s, 1H), 7.09 (s, 1H); (M−H)⁻=309.

EXAMPLE 57

5-[6-Hydroxy-7-(1,1,4-trioxo-1,2,5-thiadiazolidin-2-yl)-1,2,3,4-tetrahydronaphthalen-2-yl]-2,2-dimethylpentanoic acid methyl ester

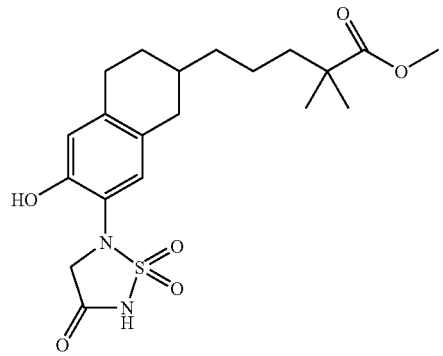

A. (E)-5-(6-Methoxy-3,4-dihydronaphthalen-2-yl)-2,2-dimethylpent-4-enoic acid methyl ester To a solution of 2,2-dimethyl-4-pentenoic acid (3.0 g, 23 mmol) in DCM/MeOH (4:1 v/v, 40 mL) is added (trimethylsilyl)diazomethane (2.0 M in hexane, 17.6 mL) slowly. After it is stirred for 0.5 h, the solvent is removed under vacuum gently to give methyl 2,2-diemethyl-4-pentenoate as a yellow oil: ¹H NMR (CDCl₃) δ 1.16 (s, 6H), 2.25 (d, J=7.33 Hz, 2H), 3.65 (s, 3H), 5.00-5.04 (m, 1H), 5.05 (m, 1H), 5.66-5.77 (m, 1H).

To a solution of trifluoromethanesulfonic acid 6-methoxy-3,4-dihydronaphthlen-2-yl ester (5.6 g, 18.2 mmol, Archiv der Pharmazie, 332, 23-30, 1999) and methyl 2,2-diemethyl-4-pentenoate (2.0 g, 14 mmol) in acetonitrile (10 mL) is added Pd(OAc)₂ (81 mg, 0.364 mmol), tri-o-tolyl phosphine (443 mg, 1.46 mmol) and triethyl amine (3.8 mL, 27.3 mmol) and the mixture is heated at 80° C. for 18 h. The reaction mixture is filtered through Celite, concentrated and extracted with EtOAc. The organic layer is washed with 1 N HCl solution, dried with MgSO₄ and concentrated. The residue is purified by chromatography to give the title compound as a yellow solid: ¹H NMR (CDCl₃) δ1.19 (s, 6H), 2.35-2.42 (m, 4H), 2.79-2.81 (t, J=8 Hz, 2H), 3.67 (s, 3H), 3.78 (s, 3H), 5.61-5.69 (m, 1H), 6.21 (d, J=16 Hz, 1H), 6.29 (s, 1H), 6.65-6.67 (m, 2H), 6.94 (d, J=8 Hz, 1H).

B. 5-(6-Methoxy-1,2,3,4-tetrahydronaphthalen-2-yl)-2,2-dimethylpentanoic acid methyl ester The title compound is prepared analogously to Example 52, step C.

C. 5-[6-Hydroxy-7-(1,1,4-trioxo-1,2,5-thiadiazolidin-2-yl)-1,2,3,4-tetrahydronaphthalen-2-yl]-2,2-dimethylpentanoic acid methyl ester The title compound is prepared analogously to Example 48, steps E-1 except using sodium methoxide to replace potassium t-butoxide for the forming of the heterocyclic ring: ¹H NMR (CD₃OD) δ1.17 (s, 6H), 1.29-1.32 (m, 5H), 1.39-1.41 (m, 2H), 1.60-1.70 (m, 1H), 1.90-1.94 (m, 1H), 2.25-2.35 (m, 1H), 2.69-2.71 (m, 3H), 3.64 (s, 3H), 4.27 (s, 2H), 6.57 (s, 1H), 7.07 (s, 1H); (M−H)⁻=423.

EXAMPLE 58

5-[6-Hydroxy-7-(1,1,4-trioxo-1,2,5-thiadiazolidin-2-yl)-1,2,3,4-tetrahydronaphthalen-2-yl]-2,2-dimethyl-pentanoic acid

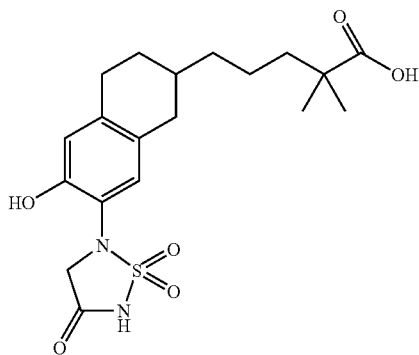

To a solution of 5-[6-Hydroxy-7-(1,1,4-trioxo-1,2,5-thiadiazolidin-2-yl)-1,2,3,4-tetrahydronaphthalen-2-yl]-2,2-dimethylpentanoic acid methyl ester (50 mg, 0.12 mmol) in THF/MeOH/H$_2$O (3:3:1 v/v/v, 1 mL,) is added NaOH (50 mg) and it is heated at 80° C. in microwave for 10 min. The solution is concentrated, dissolved in H$_2$O and neutralized with 1N HCl solution. It is then purified by RP-HPLC to give the title compound as a light yellow solid: $^1$H NMR(CD$_3$OD) δ1.17 (s, 6H), 1.29-1.35 (m, 5H), 1.39-1.41 (m, 2H), 1.60-1.70 (m, 1H), 1.90-1.94 (m 1H), 2.25-2.35 (m, 1H), 2.71-2.75 (m, 3H), 4.27 (s, 2H), 6.59 (s, 1H), 7.09 (s, 1H); (M−H)$^−$=409.

EXAMPLE 59

5-(6-Hydroxy-2-methyl-2,3-dihydrobenzo[b]thiophen-5-yl)-1,1-dioxo-1,2,5-thiadiazolidin-3-one

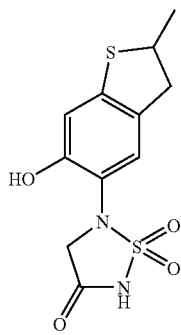

A.
6-Methoxy-2-methyl-2,3-dihydrobenzo[b]thiophene

The title compound is prepared from 6-methoxy-2-methylbenzo[b]thiophene (WO03/106462) based on the procedure described in Tetrahedron Vol 31, 1975, page 311-315.

B.
5-Bromo-2-methyl-2,3-dihydrobenzo[b]thiophen-6-ol

The title compound is prepared analogously to Example 48, steps D-E.

C. 6-Benzyloxy-5-bromo-2-methyl-2,3-dihydrobenzo[b]thiophene

The title compound is prepared analogously to Example 1, steps B.

D. 6-Benzyloxy-2-methyl-2,3-dihydrobenzo[b]thiophen-5-yl-boronic acid

To a solution of 6-benzyloxy-5-bromo-2-methyl-2,3-dihydrobenzo[b]thiophene (1.0 g, 3.0 mmol) in THF at 0° C. is added n-BuLi (1.8 mL, 4.5 mmol, 2.5 M in hexane) and the mixture is stirred for 1.5 h at 0° C. B(OMe)$_3$ (1.67 mL, 15 mmol) is added dropwise and it is warmed to RT and stirred for 1.5 h. 3M HCl solution is added slowly at 0° C. and EtOAc is added to extract the product. The organic phase is dried with MgSO$_4$ and concentrated. The residue is purified by chromatography to give the title compound as a white solid: (M+H)$^+$=301.

E. 5-(6-Benzyloxy-2-methyl-2,3-dihydrobenzo[b]thiophen-5-yl)-2-(2,4-dimethoxybenzyl)-1,1-dioxo-1,2,5-thiadiazolidin-3-one 6-Benzyloxy-2-methyl-2,3-dihydrobenzo[b]thiophen-5-yl-boronic acid (163 mg, 0.54 mmol), 2-(2,4-mimethoxybenzyl)-1,1-dioxo-1,2,5-thiadiazolidin-3-one (296 mg, 1.1 mmol, WO 2003082841), Cu(OAc)$_2$ (198 mg, 1.1 mmol), pyridine (0.09 mL, 1.1 mmol) and 1 scoop of molecular sieves in DCM is stirred at RT for 70 h. The mixture is filtered through Celite and the filtrate is washed with brine, dried with MgSO$_4$ and concentrated. The residue is purified by chromatography to give the title compound: (M+H)$^+$=541.

F. 5-(6-Benzyloxy-2-methyl-2,3-dihydrobenzo[b]thiophen-5-yl)-1,1-dioxo-1,2,5-thiadiazolidin-3-one To a solution of 5-(6-benzyloxy-2-methyl-2,3-dihydrobenzo[b]thiophen-5-yl)-2-(2,4-dimethoxybenzyl)-1,1-dioxo-1,2,5-thiadiazolidin-3-one (71 mg, 0.13 mmol) in DCM (8 mL) is added TFA (10 mL) and the mixture is stirred at RT for 4 h. TFA and DCM are removed under vacuum to give the title compound and it is used directly in the next step: (M+H)$^+$=301.

G. 5-(6-Hydroxy-2-methyl-2,3-dihydrobenzo[b]thiophen-5-yl)-1,1-dioxo-1,2,5-thiadiazolidin-3-one The title compound is prepared analogously to Example 1, step I: (M−H)$^−$=409.

EXAMPLE 60

5-(6-Hydroxyindan-5-yl)-1,1-dioxo-1,2,5-thiadiazolidin-3-one

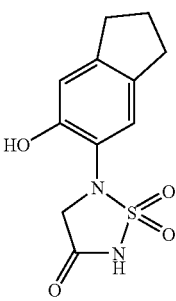

A. 6-Benzyloxy-indan-5-ylamine

6-Benzyloxyindan-5-ylamine is prepared analogously to Example 45, step F, starting with 5-benzyloxy-6-nitro-indan.

B. (6-Benzyloxyindan-5-ylamino)-acetic acid methyl ester

To a stirred solution of 6-benzyloxyindan-5-ylamine (2.00 g, 8.37 mmol) in MeCN (50 mL) is added AcOH (25 mL) followed by ethyl gloxylate (50% in toluene, 2.49 mL, 12.6 mmol). This is stirred for 2 h, then cooled to 0° C. A slurry of sodium triacetoxyborohydride (3.55 g, 16.7 mmol) is added and this is stirred for 10 min, at which time LCMS reveals complete consumption of the starting material. The reaction is diluted with saturated NaHCO$_3$ and DCM, and the organic layer is separated, washed with brine, dried over MgSO$_4$ and concentrated in vacuo to afford (6-benzyloxyindan-5-ylamino)-acetic acid methyl ester as a brown gummy solid.

C. 5-(6-Benzyloxyindan-5-yl)-1,1-dioxo-1,2,5-thiadiazolidin-3-one 5-(6-Benzyloxyindan-5-yl)-1,1-dioxo-1,2,5-thiadiazolidin-3-one is prepared analogously to Example 1, steps F-H.

D. 5-(6-Hydroxyindan-5-yl)-1,1-dioxo-1,2,5-thiadiazolidin-3-one 5-(6-Hydroxyindan-5-yl)-1,1-dioxo-1,2,5-thiadiazolidin-3-one is prepared analogously to Example 4, step B: $^1$H NMR (MeOD) δ 7.23 (s, 1H), 6.76 (s, 1H), 4.31 (s, 2H), 2.82 (q, J=7.49 Hz, 4H), 2.05 (m, 2H).

EXAMPLE 61

5-(6-Hydroxy-2,2-dimethylindan-5-yl)-1,1-dioxo-1,2,5-thiadiazolidin-3-one

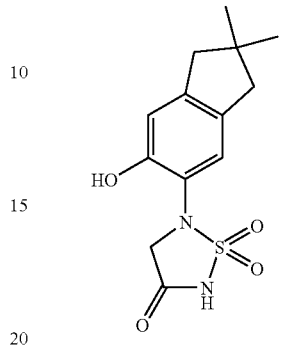

A. 6-Bromo-2,2-dimethylindan-5-ol

The title compound is prepared analogously to Example 48, steps A-E, from 5-methoxy-indan-1-one.

B. 5-Benzyloxy-6-bromo-2,2-dimethylindan

The title compound is prepared analogously to Example 1, step B: $^1$H NMR (CDCl$_3$) δ1.13 (s, 6H), 2.63 (s, 2H), 2.65 (s, 2H), 5.10 (s, 2H), 6.78 (s, 1H), 7.33-7.49 (m, 6H).

C. 5-(6-Benzyloxy-2,2-dimethylindan-5-yl)-2-(2,4-dimethoxybenzyl)-1,1-dioxo-1,2,5-thiadiazolidin-3-one The title compound is prepared analogously to Example 59, steps D-E: (M+H)$^+$=537.

D. 5-(6-Hydroxy-2,2-dimethylindan-5-yl)-1,1-dioxo-1,2,5-thiadiazolidin-3-one The title compound is prepared analogously to Example 1, step I: $^1$H NMR (CD$_3$OD) δ 1.12 (s, 6H), 2.61 (s, 2H), 2.63 (s, 2H), 4.25 (s, 2H), 6.69 (s, 1H), 7.17 (s, 1H); (M−H)$^-$=295.

EXAMPLE 62

5-(6-Hydroxy-2-methylindan-5-yl)-1,1-dioxo-1,2,5-thiadiazolidin-3-one

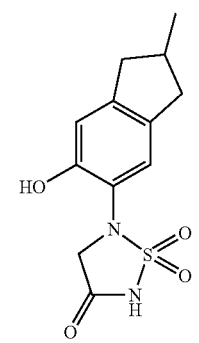

A. 5-Methoxy-2-methylindan-1-one

To a solution of diisopropylamine (5.2 mL, 36.9 mmol), in THF (20 mL) is added n-BuLi (14.8 mL, 36.9 mmol, 2.5 M in hexane) at −78° C. After 30 min, 5-methoxyindan-1-one (5.0 g, 30.8 mmol) in THF (35 mL) is added. After it is stirred at −78° C. for 1 h, the mixture is warmed to 10° C. for 30 min. The mixture is cooled again to −78° C. and methyl iodide (2.3 mL, 36.9 mmol) is added. The mixture is then warmed to RT over 1 h. NH$_4$Cl solution is added and extracted with EtOAc. The organic extract is dried with MgSO$_4$, concentrated and purified by chromatography to give the title compound (2.38 g): (M+H)$^+$=177.

B. 6-Bromo-2-methylindan-5-ol

The title compound is prepared analogously to Example 48, steps B-E.

C. 5-Benzyloxy-6-bromo-2-dimethylindan

The title compound is prepared analogously to Example 1, step B.

D. 5-(6-Hydroxy-2-methylindan-5-yl)-1,1-dioxo-1,2,5-thiadiazolidin-3-one

The title compound is prepared analogously to Example 61, steps B-C: $^1$H NMR (CD$_3$OD) δ1.07 (m, 3H), 2.36-2.48 (m, 3H), 2.89-2.93 (m, 2H), 4.22 (s, 2H), 6.68 (s, 1H), 7.15 (s, 1H); (M−H)$^-$=281.

To a solution of 5-(3-hydroxy-7,7-dimethyl-5,6,7,8-tetrahydronaphthalen-2-yl)-1,1-dioxo-1,2,5-thiadiazolidin-3-one potassium salt (47 mg, 0.14 mmol; prepared from the title compound of Example 49 analogously to procedure as described in Example 1, step I) in DMF (3 mL) at 0° C. is added potassium t-butoxide (1M in THF, 0.13 mL,). After 5 min, benzoyl chloride (0.016 mL, 0.14 mmol) is added. The mixture is stirred at 0° C. for 5 min. The mixture is partitioned between Et$_2$O and aq. K$_2$CO$_3$. The ether layer is removed. The aqueous layer is acidified by adding 3M HCl solution, and Et$_2$O is added to extract the product. The organic residue is purified by HPLC to give the title compound as a solid: $^1$H NMR (CD$_3$OD) δ 1.02 (s, 6H), 1.62 (t, J=7 Hz, 2H), 2.59 (s, 2H), 2.88 (t, J=7 Hz, 2H), 4.43 (s, 2H), 7.11 (s, 1H), 7.23 (s, 1H), 7.52-7.55 (m, 2H), 7.65-7.69 (m, 1H), 8.16-8.19 (m, 2H); (M+H)$^+$=413.

EXAMPLE 64

The following compounds are prepared using appropriate starting materials and general procedures described in Example 63.

EXAMPLE 63

Benzoic acid 6,6-dimethyl-3-(1,1,4-trioxo-1,2,5-thiadiazolidin-2-yl)-5,6,7,8-tetrahydronaphthalen-2-yl ester

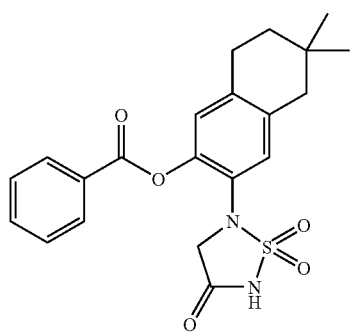

| Example | Chemical Name | MS (m/z) |
|---------|---------------|----------|
| 64-1 | Benzoic acid (S)-6-ethyl-3-(1,1,4-trioxo-1,2,5-thiadiazolidin-2-yl)-5,6,7,8-tetrahydronaphthalen-2-yl ester | (M − H)$^-$ = 413 |
| 64-2 | Benzoic acid 6-ethyl-3-(1,1,4-trioxo-1,2,5-thiadiazolidin-2-yl)-5,6,7,8-tetrahydronaphthalen-2-yl ester | (M − H)$^-$ = 413 |
| 64-3 | Benzoic acid 6,6-diethyl-3-(1,1,4-trioxo-1,2,5-thiadiazolidin-2-yl)-5,6,7,8-tetrahydronaphthalen-2-yl ester | (M − H)$^-$ = 441 |
| 64-4 | Benzoic acid 2,2-dimethyl-6-(1,1,4-trioxo-1,2,5-thiadiazolidin-2-yl)-indan-5-yl ester | (M − H)$^-$ = 399 |

| Example | NMR |
|---------|-----|
| 64-1 | $^1$H NMR (CD$_3$OD) δ 8.08 (d, J = 8 Hz, 2H), 7.55 (t, J = 8 Hz, 1H), 7.42 (t, J = 8 Hz, 2H), 7.23 (s, 1H), 6.90 (s, 1H), 4.10 (s, 2H), 2.89-2.65 (m, 3H), 2.32 (dd, J = 16, 12 Hz, 1H), 1.92-1.85 (m, 1H), 1.60-1.48 (m, 1H), 1.49-1.25 (m, 3H), 0.92 (t, J = 8 Hz, 3H) |
| 64-2 | $^1$H NMR (CD$_3$OD) δ 8.08 (d, J = 8 Hz, 2H), 7.55 (t, J = 8 Hz, 1H), 7.42 (t, J = 8 Hz, 2H), 7.23 (s, 1H), 6.90 (s, 1H), 4.10 (s, 2H), 2.89-2.65 (m, 3H), 2.32 (dd, J = 16, 12 Hz, 1H), 1.92-1.85 (m, 1H), 1.60-1.48 (m, 1H), 1.49-1.25 (m, 3H), 0.92 (t, J = 8 Hz, 3H) |

EXAMPLE 65

5-(3-Allyloxy-6-hydroxybenzo[d]isoxazol-5-yl)-1,1-dioxo-1,2,5-thiadiazolidin-3-one

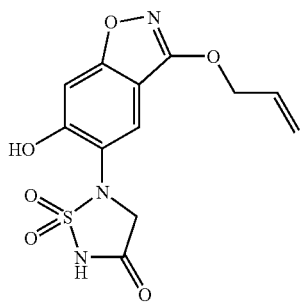

A. 2,4-Dihydroxy-5-nitrobenzoic acid

To an ice cold stirred solution of nitric acid (70%, 28 mL) and AcOH (30 mL), is added portionwise 2,4-dihydroxybenzoic acid (7.7 g, 49.9 mmol). The mixture is stirred at 0° C. for 15 min and then slowly warmed to room temperature. The reaction becomes very exothermic and is cooled again in an ice bath to keep the mixture at approximately room temperature. The mixture is stirred at room temperature for 18 h. The resulting precipitate is filtered, washed with water, air dried, then washed with DCM and dried under reduced pressure to afford 2,4-dihydroxy-5-nitrobenzoic acid as a solid: $(M-H)^-=198.1$.

B. 2,4-Dihydroxy-5-nitrobenzoyl chloride

A mixture of 2,4-dihydroxy-5-nitrobenzoic acid (14.2 g, 92.1 mmol), thionyl chloride (100 mL, 1.15 mol) and dimethylformamide (4 drops) is refluxed for 4 h. The solvents are removed under reduced pressure and the resulting gum is stripped once with toluene and dried under reduced pressure to afford 2,4-dihydroxy-5-nitrobenzoyl chloride as a gum, which is used without further purification.

C. 2,4,N-Trihydroxy-5-nitrobenzamide

A solution of 2,4-dihydroxy-5-nitrobenzoyl chloride (17.0 g, 78.1 mmol) in dioxane (70 mL) is added to an ice cold solution of 50% aqueous hydroxylamine (35 mL) and water (35 mL). After the addition is complete, the ice bath is removed and the mixture is stirred at room temperature for 30 min. The resulting thick precipitate is filtered, washed once with 1:1 water/dioxane and dried to obtain 2,4,N-trihydroxy-5-nitrobenzamide. After standing in the refrigerator for 18 h, the 1:1 water/dioxane solution affords additional 2,4,N-trihydroxy-5-nitrobenzamide: $(M+H)^+=215.1$.

D. 5-Nitrobenzo[d]isoxazole-3,6-diol

Thionyl chloride (20 mL) is added dropwise to a mixture of 2,4,N-trihydroxy-5-nitrobenzamide (6.7 g, 31.3 mmol) in THF (500 mL). The mixture is allowed to come to reflux during the addition and then heated at 55° C. for 18 h. The mixture is allowed to cool to room temperature. The insoluble precipitate is filtered off and the filtrate is concentrated and stripped twice with toluene to a give 4-nitro-6-(2-oxo-[1,3,2,4]dioxathiazol-5-yl)-benzene-1,3-diol as a gummy solid. To a suspension of the solid in dioxane (100 mL) is added dropwise triethylamine (16.9 mL, 121 mmol). After stirring at room temperature for 45 min, ice and water are added and the mixture is acidified with 1N HCl. The mixture is extracted twice with EtOAc and the organic layers are washed with 1N HCl and brine, and dried over MgSO$_4$, filtered and concentrated. The crude material is purified using flash chromatography on silica gel eluting with 1:1 EtOAc/hexanes to afford 5-nitrobenzo[d]isoxazole-3,6-diol as a yellow solid: $(M-H)^-=195.1$.

E. 3,6-Bis-allyloxy-5-nitrobenzo[d]isoxazole

To a suspension of 5-nitrobenzo[d]isoxazole-3,6-diol (1.1 g, 5.61 mmol) and potassium carbonate (3.9 g, 28.2 mmol) in DMF (10 mL) is added dropwise allyl bromide (1.42 mL, 8.30 mmol). The mixture is stirred at room temperature for 18 h. The mixture is diluted with EtOAc, and ice and water are added. The organic phase is separated and washed with water and brine, and dried over MgSO$_4$, filtered and concentrated to afford 3,6-bis-allyloxy-5-nitrobenzo[d]isoxazole as a solid.

F. 3,6-Bis-allyloxybenzo[d]isoxazol-5-ylamine

To a solution of 3,6-bis-allyloxy-5-nitrobenzo[d]isoxazole (0.60 g, 2.17 mmol) in EtOAc (12 mL) is added portionwise tin(II) chloride dihydrate (2.2 g, 9.75 mmol). The mixture is stirred at room temperature for 2 h and then at 60° C. for 1.5 h. The mixture is diluted with EtOAc and saturated NaHCO$_3$ is added dropwise, resulting in the formation of a precipitate. Sodium carbonate (2N) is added and the insoluble precipitate is filtered off. The phases are separated and the aqueous phase is extracted with EtOAc (3×). The organic layers are washed with water and brine, dried over MgSO$_4$, filtered and concentrated. The crude material is purified by flash chromatography on silica gel, eluting with a gradient of hexanes/EtOAc to afford 3,6-bis-allyloxybenzo[d]isoxazol-5-ylamine as a waxy solid: $(M+H)^+=247.2$.

G. 5-(3,6-Bis-allyloxybenzo[d]isoxazol-5-yl)-1,1-dioxo-1,2,5-thiadiazolidin-3-one The 1,1-dioxo-1,2,5-thiadiazolidin-3-one ring is prepared analogously to Example 1, steps E-H, with the exception that methyl bromoacetate is used in place of ethyl bromoacetate in step E, to afford 5-(3,6-bis-allyloxybenzo[d]isoxazol-5-yl)-1,1-dioxo-1,2,5-thiadiazolidin-3-one: $(M-H)^-=364.0$.

H. 5-(3-Allyloxy-6-hydroxybenzo[d]isoxazol-5-yl)-1,1-dioxo-1,2,5-thiadiazolidin-3-one To a solution of 5-(3,6-bis-allyloxybenzo[d]isoxazol-5-yl)-1,1-dioxo-1,2,5-thiadiazolidin-3-one (0.055 g, 0.15 mmol) in EtOH (4 mL) is added tetrakis(triphenylphosphine)palladium(0) (0.005 g, 0.004 mmol). The mixture is stirred for 5 min at room temperature, at which point potassium carbonate (0.056 g, 0.405 mmol) is added. The mixture is stirred at room temperature for 5.5 h. The solvent is removed under reduced pressure and the crude product is purified by chromatography on a Biotage purification system eluting with a gradient of water/CH$_3$CN to afford 5-(3-allyloxy-6-hydroxybenzo[d]isoxazol-5-yl)-1,1-dioxo-1,2,5-thiadiazolidin-3-one as a solid: $(M-H)^-=324.0$.

EXAMPLE 66

5-Hydroxy-6-(1,1,4-trioxo-1,2,5-thiadiazolidin-2-yl)-1H-indole-2-carboxylic acid ethyl ester potassium salt

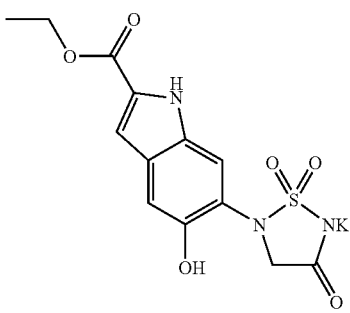

A. N-(2-Hydroxy-5-nitrophenyl)-formamide

To a stirred mixture of formic acid (20.7 g, 0.449 mol), acetic anhydride (32.0 g, 0.313 mol) and pyridine (37 g, 0.468 mol) is added at ambient temperature 2-amino-4-nitrophenol (24.0 g, 0.156 mol) in 15 mL of formic acid. Stirring is continued for 18 h. The solid formed is separated by suction filtration, washed with aqueous sodium bicarbonate, water, DCM and hexanes. After air drying for 18 h, N-(2-hydroxy-5-nitrophenyl)-formamide is obtained as a light green solid: $(M-H)^-=181.1$.

B. N-(2-Benzyloxy-5-nitrophenyl)-formamide

To a solution of N-(2-hydroxy-5-nitrophenyl)-formamide (26 g, 0.143 mol) in DMF (180 mL) is added potassium carbonate (22 g, 0.159-mol), followed by benzyl bromide (27 g, 0.158 mol) at 60° C. The mixture is stirred for 1.25 h. The mixture is diluted with water. The precipitated solid is separated by filtration and washed with 1N HCl, water and hexanes, and air dried for 18 h to afford N-(2-benzyloxy-5-nitrophenyl)-formamide as a white solid: $(M-H)^-=271.1$.

C. N-(5-Amino-2-benzyloxyphenyl)-formamide

A mixture of N-(2-benzyloxy-5-nitrophenyl)-formamide (9.0 g, 33 mmol), 5% Pt/C (3.1 g) and EtOH at 65° C. is stirred under an atmosphere of $H_2$ for 19 h at ambient temperature. The mixture is filtered through Celite, washed with EtOH and the filtrate is concentrated at reduced pressure. The resulting solid is washed with MTBE several times to afford N-(5-amino-2-benzyloxyphenyl)-formamide as a white solid: $(M-H)^-=241.1$.

D. 5-Benzyloxy-6-formylamino-1H-indole-2-carboxylic acid ethyl ester

To a solution of N-(5-amino-2-benzyloxyphenyl)-formamide (3.35 g, 13.8 mmol) in 0.3N HCl (91 mL) is added sodium nitrite (0.285 g, 4.13 mmol) at 0° C. The mixture is stirred for 0.5 h. This mixture is added to a solution prepared by mixing ethyl-2-methylacetoacetate (0.72 g, 4.99 mmol) with potassium hydroxide (0.28 g, 4.99 mmol) at 0° C. The combined mixture is stirred for ~1 h. To the reaction mixture is added saturated aqueous sodium chloride and extracted with EtOAc. The combined organic extracts are washed with water and brine, dried over anhydrous magnesium sulfate, filtered and concentrated to afford a mixture of 2-[(4-benzyloxy-3-formylaminophenyl)-hydrazono]-propionic acid ethyl ester and 2-(4-benzyloxy-3-formylaminophenylazo)-2-methyl-3-oxo-butyric acid ethyl ester as a dark oil. The mixture of 2-[(4-benzyloxy-3-formylaminophenyl)-hydrazono]-propionic acid ethyl ester and 2-(4-benzyloxy-3-formylaminophenylazo)-2-methyl-3-oxo-butyric acid ethyl ester, is dissolved in formic acid (10 mL) and stirred at 80° C. for 4.5 h. The reaction mixture is neutralized with saturated sodium bicarbonate and the resulting mixture is extracted with EtOAc and washed with brine and water. The organic phase is separated and dried over $MgSO_4$ and concentrated to afford 5-benzyloxy-6-formylamino-1H-indole-2-carboxylic acid ethyl ester as a grey solid: $(M-H)^-=337.1$.

E. 6-Amino-5-benzyloxy-1H-indole-2-carboxylic acid ethyl ester

5-Benzyloxy-6-formylamino-1H-indole-2-carboxylic acid ethyl ester (0.2 g, 0.591 mmol) is suspended in a 9:1 mixture of acetone/water (10 mL). The suspension is treated with 1N HCl (1.8 mL) and brought to reflux for 1 h. The separated solid is filtered, washed with saturated aqueous sodium bicarbonate and water, and air dried for 2 h to afford 6-amino-5-benzyloxy-1H-indole-2-carboxylic acid ethyl ester as a grey solid: $(M-H)^-=311$.

F. 5-Hydroxy-6-(1,1,4-trioxo-1,2,5-thiadiazolidin-2-yl)-1H-indole-2-carboxylic acid ethyl ester 5-Hydroxy-6-(1,1,4-trioxo-1,2,5-thiadiazolidin-2-yl)-1H-indole-2-carboxylic acid ethyl ester is prepared following the general procedures outlined in Example 1, steps E-I, with the exception that in step I, the ester is dissolved in a mixture of water/ethanol (1:1): $(M-H)^-=338$.

EXAMPLE 67

5-Hydroxy-6-(1,1,4-trioxo-1,2,5-thiadiazolidin-2-yl)-1H-indole-2-carboxylic acid 3-methyl-butyl ester

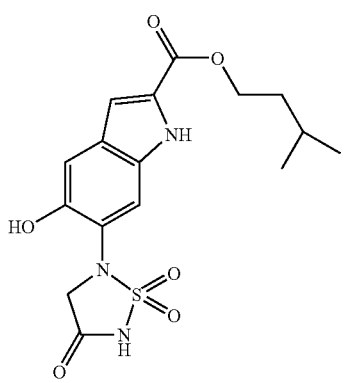

A. 6-Amino-5-benzyloxy-1H-indole-2-carboxylic acid

6-Amino-5-benzyloxy-1H-indole-2-carboxylic acid ethyl ester (65, step E) (500 mg) is suspended in ethanol (15 mL).

Water (10 mL) is added, followed by KOH (1M, 5 mL). The suspension is stirred at 75° C. for 2.5 h. The solvent is evaporated to afford 6-amino-5-benzyloxy-1H-indole-2-carboxylic acid.

B. 6-Amino-5-benzyloxy-1H-indole-2-carboxylic acid 3-methyl-butyl ester

6-Amino-5-benzyloxy-1H-indole-2-carboxylic acid is suspended in isopentanol (10 mL) and concentrated sulfuric acid (10 drops) is added. The mixture is stirred at 115° C. for 10 min and then stirred at 90° C. for 3 h. Ethyl acetate is added and the mixture is neutralized with saturated sodium bicarbonate. The mixture is then washed with saturated NaCl (3×) and water (1×), dried over MgSO$_4$, filtered, and concentrated to afford 6-amino-5-benzyloxy-1H-indole-2-carboxylic acid 3-methyl-butyl ester.

C. 5-Hydroxy-6-(1,1,4-trioxo-1,2,5-thiadiazolidin-2-yl)-1H-indole-2-carboxylic acid 3-methyl-butyl ester The 1,1-dioxo-1,2,5-thiadiazolidin-3-one ring is prepared analogously to Example 65 step F to afford 5-hydroxy-6-(1,1,4-trioxo-1,2,5-thiadiazolidin-2-yl)-1H-indole-2-carboxylic acid 3-methyl-butyl ester: (M−H)$^-$=380.0.

EXAMPLE 68

5-Hydroxy-6-(,1,1,4-trioxo-1,2,5-thiadiazolidin-2-yl)-1H-indole-2-carboxylic acid isobutyl ester

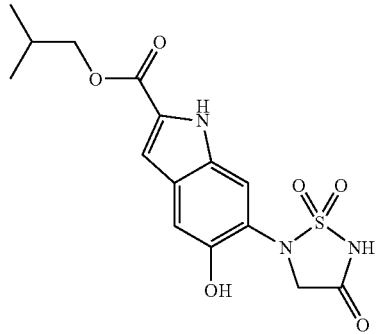

5-Hydroxy-6-(1,1,4-trioxo-1,2,5-thiadiazolidin-2-yl)-1H-indole-2-carboxylic acid isobutyl ester is prepared analogously to Example 66, using 2-methyl-propan-1-ol and heating to 95° C. for step B: (M−H)$^-$=366.

EXAMPLE 69

5-Hydroxy-6-(1,1,4-trioxo-1,2,5-thiadiazolidin-2-yl)-1H-indole-2-carboxylic acid

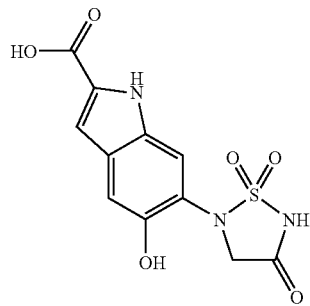

A. 5-Benzyloxy-6-(1,1,4-trioxo-1,2,5-thiadiazolidin-2-yl)-1H-indole-2-carboxylic acid To a solution of 5-benzyloxy-6-(1,1,4-trioxo-1,2,5-thiadiazolidin-2-yl)-1H-indole-2-carboxylic acid ethyl ester (from Example 65) (0.135 g, 0.398 mmol) in water (8 mL) is added 1M KOH (0.29 mL). The solution is stirred at room temperature for 1 h. The reaction product is lyophilized to yield 5-benzyloxy-6-(1,1,4-trioxo-1,2,5-thiadiazolidin-2-yl)-1H-indole-2-carboxylic acid.

B. 5-Hydroxy-6-(1,1,4-trioxo-1,2,5-thiadiazolidin-2-yl)-1H-indole-2-carboxylic acid 5-Hydroxy-6-(1,1,4-trioxo-1,2,5-thiadiazolidin-2-yl)-1H-indole-2-carboxylic acid is prepared analogously to Example 1 step I: (M−H)$^-$=310.1.

EXAMPLE 70

5-(7-Hydroxy-3-methoxy-2-oxo-2H-chromen-6-yl)-1,1-dioxo-1,2,5-thiadiazolidin-3-one

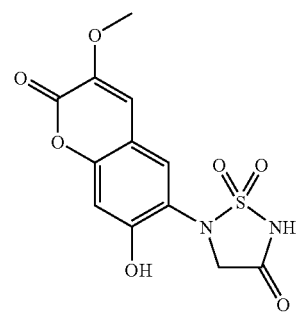

A. 4-Benzyloxy-2-hydroxybenzoic acid methyl ester

To a solution of methyl-2,4-dihydroxybenzoate (10 g, 59.5 mmol) in acetone (200 mL) at 0° C. is added K$_2$CO$_3$ (30 g, 217 mmol), followed by benzyl bromide (7.72 mL, 65 mmol). The solution is warmed to ambient temperature and stirred for 48 h. The mixture is filtered and the solvent removed under reduced pressure. The crude oil is dissolved in EtOAc and washed with water, saturated NaHCO$_3$, and dried over sodium sulfate. The solvent is removed under reduced pressure and the solid purified by flash chromatography using hexane/EtOAc (10:1) to afford 4-benzyloxy-2-hydroxybenzoic acid methyl ester as a white powder: $^1$H NMR (CDCl$_3$) δ 10.93 (s, 1H), 7.73 (d, J=9.09 Hz, 1H), 7.42-7.33 (m, 5H), 6.53-6.49 (m, 2H), 5.07 (s, 2H), 3.90 (s, 3H); (M+H)$^+$=259.

B. 5-Benzyloxy-2-hydroxymethylphenol

To a 1.0M solution of LiAlH$_4$ (22 mL) in THF at 0° C. is added dropwise a solution of 4-(benzyloxy)-2-hydroxybenzoic acid methyl ester (2.84 g, 11 mmol) in THF (15 mL). The mixture is stirred for 2 h, then quenched by the careful addition of 1 mL of saturated Na$_2$SO$_4$ solution. The mixture is warmed to ambient temperature and extracted with Et$_2$O. The organic layer is washed with water, sat. NaCl and dried over sodium sulfate. The solvent is removed under reduced pressure to afford 5-benzyloxy-2-hydroxymethylphenol as a white solid: $^1$H NMR (DMSO-d$_6$) δ 9.28 (s, 1H), 7.42-7.31

(m, 5H), 7.11 (d, J=8.34 Hz, 1H), 6.44-6.40 (m, 2H), 5.01 (s, 2H), 4.75-4.72 (m, 1H), 4.38 (d, J=5.56 Hz, 2H); (M–H)⁻=229.

C. 4-Benzyloxy-2-hydroxybenzaldehyde

To a solution of 5-benzyloxy-2-hydroxymethylphenol (2.39 g, 10.4 mmol) in $CH_2Cl_2$ (52 mL) and MeOH (5 mL) is added $MnO_2$ (9.05 g, 104 mmol). The suspension is stirred at ambient temperature overnight. The mixture is filtered and the solvent removed under reduced pressure. The crude material is purified by flash chromatography using $CH_2Cl_2$ to afford 4-benzyloxy-2-hydroxybenzaldehyde as a pale yellow solid: $^1$H NMR (CDCl$_3$) δ 11.45 (s, 1H), 9.70 (s, 1H), 7.43-7.39 (m, 6H), 6.59 (dd, J=2.28 Hz), 6.50 (d, J=2.27 Hz, 1H), 5.10 (s, 2H); (M+H)⁺=229.

D. 4-Benzyloxy-2-hydroxy-5-nitrobenzaldehyde

To a solution of 4-benzyloxy-2-hydroxybenzaldehyde (0.5 g, 2.2 mmol) in 4.4 mL of acetic acid, at 0° C., is added nitric acid (0.28 mL, 4.4 mmol) dropwise. The mixture is stirred at ambient temperature for 18 h. The mixture is poured into water and extracted with EtOAc. The organic layer is washed with water, sat. NaCl and dried over sodium sulfate. The solvent is removed under reduced pressure and the crude material is purified by flash chromatography using hexane/EtOAc (6:1) to afford 4-benzyloxy-2-hydroxy-5-nitrobenzaldehyde as a yellow solid: $^1$H NMR (acetone-d$_6$) δ 11.84 (s, 1H), 10.08 (s, 1H), 8.59 (s, 1H), 7.64-7.45 (m, 5H), 6.99 (s, 1H), 5.54 (s, 2H); (M–H)⁻=272.

E. 7-Benzyloxy-3-methoxy-6-nitrochromen-2-one

Sodium methoxyacetate (0.739 g, 6.6 mmol), prepared from methoxyacetic acid and NaOH in EtOH, is dissolved in 3.3 mL of DMF and cooled to 0° C. Methoxyacetyl chloride (0.39 mL, 4.0 mmol) is added dropwise. The mixture is stirred for 15 min at ambient temperature. 4-Benzyloxy-2-hydroxy-5-nitrobenzaldehyde (0.360 g, 1.32 mmol) is added and the solution refluxed for 3 h. After cooling to ambient temperature, EtOAc is added and the mixture is washed with 10% aqueous HCl, water, and sat. NaCl, then dried over sodium sulfate. The solvent is removed under reduced pressure and the residue purified by recrystallization from EtOAc to afford 7-benzyloxy-3-methoxy-6-nitrochromen-2-one as a yellow solid: mp=226-228° C.; $^1$H NMR (DMSO-d$_6$) δ 8.27 (s, 1H), 7.48-7.35 (m, 7H), 5.36 (s, 2H), 3.82 (s, 3H); (M–H)⁻=326.

F. 6-Amino-7-benzyloxy-3-methoxychromen-2-one

To a solution of 7-benzyloxy-3-methoxy-6-nitrochromen-2-one (0.20 g, 0.61 mmol) in 20 mL of THF is added a solution of $Na_2S_2O_4$ (1.0 g) in water (6 mL). The mixture is heated at 80° C. for 18 h. Additional $Na_2S_2O_4$ is added until the reaction is complete. After cooling to ambient temperature, EtOAc is added and the mixture is washed with water and sat. NaCl, then dried over sodium sulfate. The solvent is removed under reduced pressure to afford 6-amino-7-benzyloxy-3-methoxychromen-2-one as a pale yellow solid: $^1$H NMR (CDCl$_3$) δ 7.44-7.34 (m, 5H), 6.81 (s, 1H), 6.70 (s, 1H), 6.68 (s, 1H), 5.11 (s, 2H), 3.85 (s, 3H); (M+H)⁺=298.

G. (7-Benzyloxy-3-methoxy-2-oxo-2H-chromen-6-ylamino)-acetic acid methyl ester To a suspension of 6-amino-7-benzyloxy-3-methoxy-chromen-2-one (0.880 g, 2.96 mmol) and $K_2CO_3$ (0.820 g, 5.92 mmol) in DMF (50 mL) is added methyl bromoacetate (0.36 mL, 3.85 mmol). The mixture is stirred at 60° C. for 3 h. Additional methyl bromoacetate (0.14 mL) is added, and after 3 h, the mixture is allowed to cool to ambient temperature and poured into water and extracted with EtOAc. The organic layer is washed with water (3×), sat. NaCl, and dried over sodium sulfate. The solvent is removed under reduced pressure and the residue purified by flash chromatography using hexanes/EtOAc (7:1) to afford (7-benzyloxy-3-methoxy-2-oxo-2H-chromen-6-ylamino)-acetic acid methyl ester as a yellow solid: $^1$H NMR (CDCl$_3$) δ 7.44-7.33 (m, 5H), 6.79 (s, 1H), 6.75 (s, 1H), 6.36 (s, 1H), 5.13 (s, 2H), 3.95 (s, 2H), 3.85 (s, 3H), 3.77 (s, 3H); (M+H)⁺=370.

H. N-(t-Butoxycarbonylsulfamoyl)-N-(7-benzyloxy-3-methoxy-2-oxo-2H-chromen-6-yl)glycine methyl ester To a solution of chlorosulfonyl isocyanate (0.15 mL, 1.75 mmol) in 4 mL of $CH_2Cl_2$, cooled in a ice bath, is added t-butanol (0.17 mL, 1.75 mmol). The mixture is warmed to ambient temperature and stirred for 15 min. The solution is cooled in an ice bath and a solution of (7-benzyloxy-3-methoxy-2-oxo-2H-chromen-6-ylamino)-acetic acid methyl ester (0.430 g, 1.17 mmol) and triethylamine (0.35 mL, 2 mmol) is added dropwise. After addition is complete, the mixture is warmed to ambient temperature and stirred for 1.5 h. To this is added water (1 mL) and the mixture is extracted with EtOAc. The organic layer is washed with water, sat. NaCl and dried over sodium sulfate. The solvent is removed under reduced pressure to afford N-(t-butoxycarbonylsulfamoyl)-N-(7-benzyloxy-3-methoxy-2-oxo-2H-chromen-6-yl)glycine methyl ester as a white solid: $^1$H NMR (CDCl$_3$) δ 7.78 (s, 1H), 7.71 (s, 1H), 7.38-7.30 (m, 5H), 6.82, (s, 1H), 6.78 (s, 1H), 5.18 (s, 2H), 4.55 (s, 2H), 3.83 (s, 3H); 3.66 (s, 3H), 1.41 (s, 9H); (M+H)⁺=549.

I. N-Sulfamoyl-N-(7-benzyloxy-3-methoxy-2-oxo-2H-chromen-6-yl)glycine methyl ester A solution of N-(t-butoxycarbonylsulfamoyl)-N-(7-benzyloxy-3-methoxy-2-oxo-2H-chromen-6-yl)glycine methyl ester (0.550 g, 1 mmol) in 40 mL of $CH_2Cl_2$/TFA (3:1) is stirred for 40 min at ambient temperature. The solvent is removed under reduced pressure. Methylene chloride is added to the residue and the solvent removed under reduced pressure (4×). The residue is purified by flash chromatography using $CH_2Cl_2$/EtOAc (4:1) to afford N-sulfamoyl-N-(7-benzyloxy-3-methoxy-2-oxo-2H-chromen-6-yl)glycine methyl ester as a white solid: mp=178-179° C.; $^1$H NMR (DMSO-d$_6$) δ 7.74 (s, 1H), 7.52-7.32 (m, 5H), 7.29 (s, 1H), 7.13 (s, 1H), 5.22 (s, 2H), 4.30 (s, 2H), 3.80 (s, 3H), 3.58 (s, 3H); (M–H)⁻=447.

J. 5-(7-Benzyloxy-3-methoxy-2-oxo-2H-chromen-6-yl)-1,1-dioxo-1,2,5-thiadiazolidin-3-one potassium salt To a solution of N-sulfamoyl-N-(7-benzyloxy-3-methoxy-2-oxo-2H-chromen-6-yl)glycine methyl ester (0.10 g, 0.22 mmol) in THF (20 mL) is added a 1M solution of potassium t-butoxide solution (0.44 mL, 0.44 mmol) in THF. The mixture is stirred at ambient temperature for 18 h. The solvent is removed under reduced pressure to afford 5-(7-benzyloxy-3-methoxy-2-oxo-2H-chromen-6-yl)-1,1-dioxo-1,2,5-thiadiazolidin-3-one potassium salt as a white solid. This material is used directly in the next step.

K. 5-(7-Hydroxy-3-methoxy-2-oxo-2H-chromen-6-yl)-1,1-dioxo-1,2,5-thiadiazolidin-3-one To a solution of 5-(7-benzyloxy-3-methoxy-2-oxo-2H-chromen-6-yl)-1,1-dioxo-1,2,5-thiadiazolidin-3-one potassium salt in water (10 mL), is added 10% Pd/C (0.014 g). The suspension is stirred under an atmosphere of $H_2$ for 18 h. The aqueous solution is filtered through Celite and the water is removed by lyophilization. The crude solid is purified by preparative HPLC to afford 5-(7-hydroxy-3-methoxy-2-oxo-2H-chromen-6-yl)-1,1-dioxo-1,2,5-thiadiazolidin-3-one as a pale-yellow powder: $^1$H NMR (DMSO-$d_6$) δ 7.66 (s, 1H), 7.27 (s, 1H), 6.77 (d, J=3.54 Hz, 1H), 4.03 (s, 2H), 3.77 (s, 3H); (M–H)$^-$=325.

The table below shows the inhibitory activity (IC50 values) of representative compounds of the invention to human PTP-1B.

| Compound | IC50 (nM) |
| --- | --- |
| Example No. 22 | 85 nM |
| Example No. 23 | 113 nM |

What is claimed is:

1. A compound of the formula

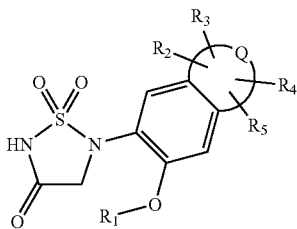

(I)

wherein

Q combined together with the carbon atoms to which it is attached form an aromatic, or a partially or fully saturated nonaromatic 5- to 8-membered carbocyclic or heterocyclic ring;

$R_1$ is hydrogen, —C(O)$R_6$, —C(O)N$R_7R_8$ or —C(O)O$R_9$ in which $R_6$ and $R_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_8$ and $R_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_2$, $R_3$, $R_4$ and $R_5$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or ($C_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_2$ and $R_3$ combined are alkylene which together with the ring atoms to which they are attached form a 3- to 7-membered fused ring; or $R_2$ and $R_3$ combined are alkylene which together with the carbon atom to which they are attached form a 3- to 7-membered spirocyclic ring;

or a pharmaceutically acceptable salt thereof.

2. The compound according to claim 1, wherein

Q combined together with the carbon atoms to which it is attached form an aromatic, or a partially or fully saturated 5- to 6-membered carbocyclic ring;

or a pharmaceutically acceptable salt thereof.

3. The compound according to claim 2 of the formula

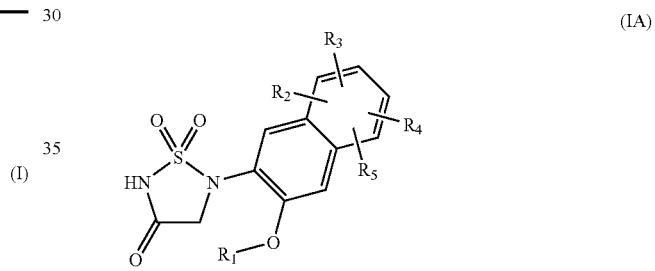

(IA)

wherein $R_1$ is hydrogen, —C(O)$R_6$, —C(O)N$R_7R_8$ or —C(O)O$R_9$ in which $R_6$ and $R_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_8$ and $R_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_2$, $R_3$, $R_4$ and $R_5$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or ($C_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_2$ and $R_3$ combined are alkylene which together with the ring atoms to which they are attached form a 5- to 7-membered fused ring; or or a pharmaceutically acceptable salt thereof.

4. The compound according to claim 3 of the formula

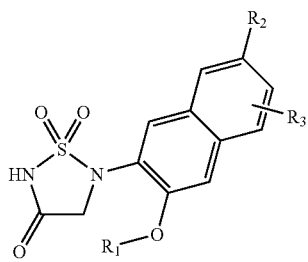

(IB)

wherein $R_1$ is hydrogen, —C(O)$R_6$, —C(O)N$R_7R_8$ or —C(O)O$R_9$ in which $R_6$ and $R_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_8$ and $R_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_2$ and $R_3$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or ($C_{1-8}$)alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy;

or a pharmaceutically acceptable salt thereof.

5. A The compound according to claim 4, wherein $R_2$ is —Y—(CH$_2$)$_n$—CR$_{10}$R$_{11}$—(CH$_2$)$_m$—X in which Y is oxygen or S(O)$_q$ in which q is zero or an integer of 1 or 2; or Y is trans CH=CH; or Y is absent;

n is an integer from 1 to 6;

$R_{10}$ and $R_{11}$ are, independently from each other, hydrogen or lower alkyl; or $R_{10}$ and $R_{11}$ combined are alkylene which together with the carbon atom to which they are attached form a 3- to 7-membered ring;

m is zero or an integer of 1 or 2;

X is hydroxy, alkoxy, cycloalkyl, cycloalkoxy, acyl, acyloxy, carbamoyl, cyano, trifluoromethyl, free or esterified carboxy, monocyclic aryl or heterocyclyl;

or a pharmaceutically acceptable salt thereof.

6. The compound according to claim 4, wherein $R_3$ is hydrogen;

or a pharmaceutically acceptable salt thereof.

7. The compound according to claim 5, wherein n is an integer of 2 or 3;

$R_{10}$ and $R_{11}$ are, independently from each other, hydrogen or lower alkyl;

m is zero or 1;

X is hydroxy, carbamoyl, cyano, trifluoromethyl, free or esterified carboxy, monocyclic aryl or heterocyclyl;

or a pharmaceutically acceptable salt thereof.

8. The compound according to claim 5, wherein

Y is absent;

or a pharmaceutically acceptable salt thereof.

9. The compound according to claim 5, wherein n is 3;

$R_{10}$ and $R_{11}$ are lower alkyl;

m is zero or 1;

X is hydroxy, cyano or free or esterified carboxy;

or a pharmaceutically acceptable salt thereof.

10. The compound according to claim 5, wherein $R_{10}$ and $R_{11}$ are methyl;

or a pharmaceutically acceptable salt thereof.

11. The compound according to any of claim 5, wherein $R_1$ is hydrogen or —C(O)$R_6$ in which $R_6$ is monocyclic aryl;

or a pharmaceutically acceptable salt thereof.

12. The compound according to claim 2 of the formula

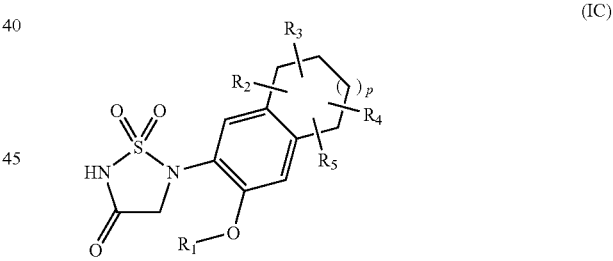

(IC)

wherein $R_1$ is hydrogen or —C(O)$R_6$, —C(O)N$R_7R_8$ or —C(O)O$R_9$ in which $R_6$ and $R_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_8$ and $R_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;

$R_2$, $R_3$, $R_4$ and $R_5$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or ($C_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_2$ and $R_3$ combined are alkylene which together with the ring atoms to which they are attached form a 3- to 7-membered fused ring; or $R_2$ and $R_3$ combined are alkylene which together with the carbon atom to which they are attached form a 3- to 7-membered spirocyclic ring;

p is zero or 1;

or a pharmaceutically acceptable salt thereof.

13. The compound according to claim 12, wherein
$R_2$ and $R_3$ are, independently from each other, hydrogen, halogen or ($C_{1-4}$)alkyl optionally substituted by at least one halogen;

or a pharmaceutically acceptable salt thereof.

14. The compound according to claim 12, wherein
p is 1;

or a pharmaceutically acceptable salt thereof.

15. The compound according to claim 1 of the formula

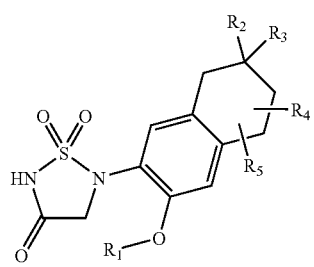

(ID)

wherein
$R_1$ is hydrogen or —C(O)$R_6$, —C(O)N$R_7R_8$ or —C(O)O$R_9$ in which
$R_6$ and $R_7$ are, independently from each other, hydrogen, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
$R_8$ and $R_9$ are, independently from each other, cycloalkyl, aryl, heterocyclyl, aralkyl, heteroaralkyl or alkyl optionally substituted with one to four substituents selected from the group consisting of halogen, cycloalkyl, cycloalkoxy, alkoxy, alkyloxyalkoxy, amino, alkylamino, dialkylamino, aryl, aryloxy and heterocyclyl;
$R_2$, $R_3$, $R_4$ and $R_5$ are, independently from each other, hydrogen, hydroxy, halogen, cyano, nitro, alkoxy, alkylthio, alkylthiono, sulfonyl, free or esterified carboxy, carbamoyl, sulfamoyl, optionally substituted amino, cycloalkyl, aryl, heterocyclyl, alkenyl, alkynyl or ($C_{1-8}$) alkyl optionally substituted with one to four substituents selected from the group consisting of halogen, hydroxy, cycloalkyl, cycloalkoxy, acyl, acyloxy, alkoxy, alkyloxyalkoxy, amino, alkylamino, dialkylamino, acylamino, carbamoyl, thiol, alkylthio, alkylthiono, sulfonyl, sulfonamido, sulfamoyl, nitro, cyano, free or esterified carboxy, aryl, aryloxy, arylthio, alkenyl, alkynyl, aralkoxy, heteroaralkoxy, heterocyclyl and heterocyclyloxy; or $R_2$ and $R_3$ combined are alkylene which together with the carbon atom to which they are attached form a 3- to 7-membered spirocyclic ring;

or a pharmaceutically acceptable salt thereof.

16. The compound according to claim 15, wherein
$R_4$ and $R_5$ are hydrogen;

or a pharmaceutically acceptable salt thereof.

17. The compound according to claim 16, wherein
$R_2$ and $R_3$ are, independently from each other, hydrogen, halogen or ($C_{1-4}$)alkyl optionally substituted by at least one halogen;

or a pharmaceutically acceptable salt thereof.

18. The compound according to claim 17, wherein
$R_1$ is hydrogen or —C(O)$R_6$ in which $R_6$ is monocyclic aryl;

or a pharmaceutically acceptable salt thereof.

19. The compound according to claim 16, wherein
$R_2$ and $R_3$ combined are alkylene which together with the carbon atom to which they are attached form a 3- to 5-membered spirocyclic ring;

or a pharmaceutically acceptable salt thereof.

20. The compound according to claim 19, wherein
$R_1$ is hydrogen or —C(O)$R_6$ in which $R_6$ is monocyclic aryl;

or a pharmaceutically acceptable salt thereof.

21. The compound according to claim 16, wherein
$R_2$ is —Y—(CH$_2$)$_n$—C$R_{10}R_{11}$—(CH$_2$)$_m$—X in which
Y is oxygen or S(O)$_q$ in which q is zero or an integer of 1 or 2; or
Y is trans CH=CH; or
Y is absent;
n is an integer from 1 to 6;
$R_{10}$ and $R_{11}$ are, independently from each other, hydrogen or lower alkyl; or
$R_{10}$ and $R_{11}$ combined are alkylene which together with the carbon atom to which they are attached form a 3- to 7-membered ring;
m is zero or an integer of 1 or 2;
X is hydroxy, alkoxy, cycloalkyl, cycloalkoxy, acyl, acyloxy, carbamoyl, cyano, trifluoromethyl, free or esterified carboxy, monocyclic aryl or heterocyclyl;

or a pharmaceutically acceptable salt thereof.

22. The compound according to claim 21, wherein
$R_3$ is hydrogen;

or a pharmaceutically acceptable salt thereof.

23. The compound according to claim 21, wherein
n is an integer of 2 or 3;
$R_{10}$ and $R_{11}$ are, independently from each other, hydrogen or lower alkyl;
m is zero or 1;
X is hydroxy, carbamoyl, cyano, trifluoromethyl, free or esterified carboxy, monocyclic aryl or heterocyclyl;

or a pharmaceutically acceptable salt thereof.

24. The compound according to claim 21, wherein
Y is absent;

or a pharmaceutically acceptable salt thereof.

25. The compound according to claim 21, wherein
n is 3;
$R_{10}$ and $R_{11}$ are lower alkyl;
m is zero or 1;
X is hydroxy, cyano or free or esterified carboxy;
or a pharmaceutically acceptable salt thereof.

26. The compound according to claim 25, wherein
$R_{10}$ and $R_{11}$ are methyl;
or a pharmaceutically acceptable salt thereof.

27. The compound according to claim 25, wherein
$R_1$ is hydrogen or —C(O)$R_6$ in which $R_6$ is monocyclic aryl;
or a pharmaceutically acceptable salt thereof.

28. The compound according to claim 1 selected from the group consisting of:
 5-(3,6-Dihydroxynaphthalen-2-yl)-1,1-dioxo-1,2,5-thiadiazolidin-3-one;
 5-(3,7-Dihydroxynaphthalen-2-yl)-1,1-dioxo-1,2,5-thiadiazolidin-3-one potassium salt;
 5-(7-Bromo-3-hydroxynaphthalen-2-yl)-1,1-dioxo-1,2,5-thiadiazolidin-3-one;
 5-(7-Ethyl-3-hydroxynaphthalen-2-yl)-1,1-dioxo-1,2,5-thiadiazolidin-3-one;
 5-{3-Hydroxy-7-[2-(4-methoxyphenyl)-ethyl]-naphthalen-2-yl}-1,1-dioxo-1,2,5-thiadiazolidin-3-one;
 5-{3-Hydroxy-7-[2-(4-trifluoromethylphenyl)-ethyl]-naphthalen-2-yl}-1,1-dioxo-1,2,5-thiadiazolidin-3-one;
 5-{3-Hydroxy-7-[2-(3-methoxyphenyl)-ethyl]-naphthalen-2-yl}-1,1-dioxo-1,2,5-thiadiazolidin-3-one;
 5-[3-Hydroxy-7-(4-methylpentyl)-naphthalen-2-yl]-1,1-dioxo-1,2,5-thiadiazolidin-3-one;
 {3-[6-Hydroxy-7-(1,1,4-trioxo-1,2,5-thiadiazolidin-2-yl)naphthalen-2-yl]-phenyl}-acetic acid;
 5-(3-Hydroxy-7-phenylnaphthalen-2-yl)-1,1-dioxo-1,2,5-thiadiazolidin-3-one;
 3-[6-Hydroxy-7-(1,1,4-trioxo-1,2,5-thiadiazolidin-2-yl)-naphthalen-2-yl]-benzoic acid;
 5-[3-Hydroxy-7-(3-trifluoromethoxyphenyl)-naphthalen-2-yl]-1,1-dioxo-1,2,5-thiadiazolidin-3-one;
 {3-[6-Hydroxy-7-(1,1,4-trioxo-1,2,5-thiadiazolidin-2-yl)-naphthalen-2-yl]-phenyl}acetonitrile;
 5-[3-Hydroxy-7-(3-hydroxymethylphenyl)-naphthalen-2-yl]-1,1-dioxo-1,2,5-thiadiazolidin-3-one;
 3-{3-[6-Hydroxy-7-(1,1,4-trioxo-thiadiazolidin-2-yl)-naphthalen-2-yl]-phenyl}-propionic acid;
 6-Hydroxy-7-(1,1,4-trioxo-1,2,5-thiadiazolidin-2-yl)-naphthalene-2-carbonitrile;
 3-[6-Hydroxy-7-(1,1,4-trioxo-1,2,5-thiadiazolidin-2-yl)-naphthalen-2-yl]-benzonitrile;
 5-[7-(3,3-Dimethylbutyl)-3-hydroxynaphthalen-2-yl]-1,1-dioxo-1,2,5-thiadiazolidin-3-one;
 5-[3-Hydroxy-7-(3-trifluoromethylphenyl)-naphthalen-2-yl]-1,1-dioxo-1,2,5-thiadiazolidin-3-one;
 3-[6-Hydroxy-7-(1,1,4-trioxo-1,2,5-thiadiazolidin-2-yl)-naphthalen-2-yl]-benzoic acid ethyl ester;
 5-[3-Hydroxy-7-(3-methanesulfonylphenyl)-naphthalen-2-yl]-1,1-dioxo-1,2,5-thiadiazolidin-3-one;
 3-{3-[6-Hydroxy-7-(1,1,4-trioxo-1,2,5-thiadiazolidin-2-yl)-naphthalen-2-yl]-phenyl}-propionitrile;
 5-[3-Hydroxy-7-(3-methoxymethylphenyl)-naphthalen-2-yl]-1,1-dioxo-1,2,5-thiadiazolidin-3-one;
 5-(7-Furan-3-yl-3-hydroxynaphthalen-2-yl)-1,1-dioxo-1,2,5-thiadiazolidin-3-one;
 N-{3-[6-Hydroxy-7-(1,1,4-trioxo-1,2,5-thiadiazolidin-2-yl)-naphthalen-2-yl]-phenyl}-methanesulfonamide;
 5-[7-(2-Fluorophenyl)-3-hydroxynaphthalen-2-yl]-1,1-dioxo-1,2,5-thiadiazolidin-3-one;
 5-(3-Hydroxy-7-o-tolylnaphthalen-2-yl)-1,1-dioxo-1,2,5-thiadiazolidin-3-one;
 5-(3-Hydroxy-7-pentylnaphthalen-2-yl)-1,1-dioxo-1,2,5-thiadiazolidin-3-one;
 5-(3-Hydroxy-7-propylnaphthalen-2-yl)-1,1-dioxo-1,2,5-thiadiazolidin-3-one;
 5-[3-Hydroxy-7-(tetrahydrofuran-3-yl)-naphthalen-2-yl]-1,1-dioxo-1,2,5-thiadiazolidin-3-one;
 {3-[6-Hydroxy-7-(1,1,4-trioxo-1,2,5-thiadiazolidin-2-yl)-naphthalen-2-yl]-phenyl}-acetic acid ethyl ester;
 3-{3-[6-Hydroxy-7-(1,1,4-trioxo-1,2,5-thiadiazolidin-2-yl)-naphthalen-2-yl]-phenyl}-propionic acid ethyl ester;
 5-[6-Hydroxy-7-(1,1,4-trioxo-1,2,5-thiadiazolidin-2-yl)-naphthalen-2-yl]-pentanoic acid ethyl ester;
 4-[6-Hydroxy-7-(1,1,4-trioxo-1,2,5-thiadiazolidin-2-yl)-naphthalen-2-yl]-2,2-dimethyl-butyric acid;
 5-[3-Hydroxy-7-((S)-4-hydroxypentyl)-naphthalen-2-yl]-1,1-dioxo-1,2,5-thiadiazolidin-3-one;
 4-[6-Hydroxy-7-(1,1,4-trioxo-1,2,5-thiadiazolidin-2-yl)-naphthalen-2-yl]-2-methylbutyronitrile;
 5-[6-Hydroxy-7-(1,1,4-trioxo-1,2,5-thiadiazolidin-2-yl)-naphthalen-2-yl]-2-methylpentanoic acid ethyl ester;
 5-[3-Hydroxy-7-(3-methylbutyl)-naphthalen-2-yl]-1,1-dioxo-1,2,5-thiadiazolidin-3-one;
 5-[6-Hydroxy-7-(1,1,4-trioxo-1,2,5-thiadiazolidin-2-yl)-naphthalen-2-yl]-2,2-dimethylpentanenitrile;
 5-[6-Hydroxy-7-(1,1,4-trioxo-1,2,5-thiadiazolidin-2-yl)-naphthalen-2-yl]-pentanoic acid;
 5-[3-Hydroxy-7-(5-hydroxypentyl)-naphthalen-2-yl]-1,1-dioxo-1,2,5-thiadiazolidin-3-one;
 2-Hydroxy-6-{2-[6-hydroxy-7-(1,1,4-trioxo-1,2,5-thiadiazolidin-2-yl)-naphthalen-2-yloxy]-ethoxy}-N,N-dimethylbenzamide;
 2-Hydroxy-6-{4-[6-hydroxy-7-(1,1,4-trioxo-1,2,5-thiadiazolidin-2-yl)-naphthalen-2-yl]-butoxy}-N,N-dimethylbenzamide;
 5-{3-Hydroxy-7-[3-(2-hydroxyethoxy)-propyl]-naphthalen-2-yl}-1,1-dioxo-1,2,5-thiadiazolidin-3-one;
 5-{3-Hydroxy-7-[2-(2-methoxyphenyl)-ethyl]-naphthalen-2-yl}-1,1-dioxo-1,2,5-thiadiazolidin-3-one;
 5-[3-Hydroxy-7-(5-oxohexyl)-naphthalen-2-yl]-1,1-dioxo-1,2,5-thiadiazolidin-3-one;
 5-{7-[3-(3,5-Dimethylpyrazol-1-yl)-propyl]-3-hydroxynaphthalen-2-yl}-1,1-dioxo-1,2,5-thiadiazolidin-3-one;
 5-{3-Hydroxy-7-[3-(2-oxocyclohexyl)-propyl]-naphthalen-2-yl}-1,1-dioxo-1,2,5-thiadiazolidin-3-one;
 5-{3-Hydroxy-7-[4-hydroxy-4-(tetrahydrofuran-2-yl)-butyl]-naphthalen-2-yl}-1,1-dioxo-1,2,5-thiadiazolidin-3-one;
 5-{3-Hydroxy-7-[1-(2-oxopyrrolidin-1-yl)-ethyl]naphthalen-2-yl}-1,1-dioxo-1,2,5-thiadiazolidin-3-one;
 5-[3-Hydroxy-7-(3-phenylpropyl)-naphthalen-2-yl]-1,1-dioxo-1,2,5-thiadiazolidin-3-one;
 5-[3-Hydroxy-7-(3-pentafluorophenylpropyl)-naphthalen-2-yl]-1,1-dioxo-1,2,5-thiadiazolidin-3-one;
 2-{3-[6-Hydroxy-7-(1,1,4-trioxo-1,2,5-thiadiazolidin-2-yl)-naphthalen-2-yl]-propyl}benzonitrile;
 5-[3-Hydroxy-7-((R)-4-hydroxypentyl)-naphthalen-2-yl]-1,1-dioxo-1,2,5-thiadiazolidin-3-one;
 5-[3-Hydroxy-7-(4-hydroxypentyl)-naphthalen-2-yl]-1,1-dioxo-1,2,5-thiadiazolidin-3-one;
 5-[3-Hydroxy-7-(4-hydroxy-3-methylbutyl)-naphthalen-2-yl]-1,1-dioxo-1,2,5-thiadiazolidin-3-one;

5-[7-(4-Ethyl-4-hydroxyhexyl)-3-hydroxynaphthalen-2-yl]-1,1-dioxo-1,2,5-thiadiazolidin-3-one;
5-[3-Hydroxy-7-(4-hydroxyheptyl)-naphthalen-2-yl]-1,1-dioxo-1,2,5-thiadiazolidin-3-one;
5-{3-Hydroxy-7-[3-(1-hydroxycyclohexyl)-propyl]-naphthalen-2-yl}-1,1-1,2,5-thiadiazolidin-3-one;
5-[6-Hydroxy-7-(1,1,4-trioxo-1,2,5-thiadiazolidin-2-yl)-naphthalen-2-yl]-2,2-dimethylpentanoic acid;
5-{3-Hydroxy-7-[2-((1S,2R)-2-hydroxycyclopentyl)-ethyl]-naphthalen-2-yl}-1,1-dioxo-1,2,5-thiadiazolidin-3-one;
5-[6-Hydroxy-7-(1,1,4-trioxo-1,2,5-thiadiazolidin-2-yl)-naphthalen-2-yl]-pentanenitrile;
5-{3-Hydroxy-7-[3-(2-hydroxycyclohexyl)-propyl]-naphthalen-2-yl}-1,1-dioxo-1,2,5-thiadiazolidin-3-one;
5-[6-Hydroxy-7-(1,1,4-trioxo-1,2,5-thiadiazolidin-2-yl)-naphthalen-2-yl]-2,2-dimethylpentanoic acid methyl ester;
5-[3-Hydroxy-7-(5,5,5-trifluoro-4-hydroxy-4-methylpentyl)-naphthalen-2-yl]-1,1-dioxo-1,2,5-thiadiazolidin-3-one;
Acetic acid 4-[6-hydroxy-7-(1,1,4-trioxo-1,2,5-thiadiazolidin-2-yl)-naphthalen-2-yl]-2-methyl butyl ester;
5-[3-Hydroxy-7-(5,5,5-trifluoro-4-hydroxypentyl)-naphthalen-2-yl]-1,1-dioxo-1,2,5-thiadiazolidin-3-one;
5-[3-Hydroxy-7-(4-hydroxy-4-methylpentyl)-naphthalen-2-yl]-1,1-dioxo-1,2,5-thiadiazolidin-3-one;
5-(7-Cyclopentyl-3-hydroxynaphthalen-2-yl)-1,1-dioxo-1,2,5-thiadiazolidin-3-one;
5-(7-Cyclohexyl-3-hydroxynaphthalen-2-yl)-1,1-dioxo-1,2,5-thiadiazolidin-3-one;
5-[3-Hydroxy-7-(3-methylsulfanylphenyl)-naphthalen-2-yl]-1,1-dioxo-1,2,5-thiadiazolidin-3-one;
5-[3-Hydroxy-7-((E)-4-hydroxy-4-methylpent-1-enyl)-naphthalen-2-yl]-1,1-dioxo-1,2,5-thiadiazolidin-3-one;
5-[6-Hydroxy-7-(1,1,4-trioxo-1,2,5-thiadiazolidin-2-yl)-naphthalen-2-yl]-thiophene-2-carbonitrile;
{3-[6-Hydroxy-7-(1,1,4-trioxo-1,2,5-thiadiazolidin-2-yl)-naphthalen-2-yl]-benzyl}-carbamic acid methyl ester;
(E)-5-[6-Hydroxy-7-(1,1,4-trioxo-1,2,5-thiadiazolidin-2-yl)-naphthalen-2-yl]-pent-4-enenitrile;
(E)-5-[6-Hydroxy-7-(1,1,4-trioxo-1,2,5-thiadiazolidin-2-yl)-naphthalen-2-yl]-2-methylpent-4-enoic acid ethyl ester;
(E)-5-[6-Hydroxy-7-(1,1,4-trioxo-1,2,5-thiadiazolidin-2-yl)naphthalen-2-yl]-2-methylpent-4-enoic acid;
(E)-5-[6-Hydroxy-7-(1,1,4-trioxo-1,2,5-thiadiazolidin-2-yl)-naphthalen-2-yl]-pent-4-enoic acid;
5-[6-Hydroxy-7-(1,1,4-trioxo-1,2,5-thiadiazolidin-2-yl)-naphthalen-2-yl]-pentanoic acid isopropyl ester;
5-[6-Hydroxy-7-(1,1,4-trioxo-1,2,5-thiadiazolidin-2-yl)-naphthalen-2-yl]-2-methylpentanoic acid methyl ester;
5-[6-Hydroxy-7-(1,1,4-trioxo-1,2,5-thiadiazolidin-2-yl)-naphthalen-2-yl]-2-methylpentanoic acid;
5-[7-(4,5-Dihydroxy-4,5-dimethylhex-1-enyl)-3-hydroxynaphthalen-2-yl]-1,1-dioxo-1,2,5-thiadiazolidin-3-one;
5-[7-(4,5-Dihydroxy-4,5-dimethylhexyl)-3-hydroxynaphthalen-2-yl]-1,1-dioxo-1,2,5-thiadiazolidin-3-one;
5-[7-(4,4-Dimethylpentyl)-3-hydroxynaphthalen-2-yl]-1,1-dioxo-1,2,5-thiadiazolidin-3-one;
Benzoic acid 6-(3-cyano-3-methylpropyl)-3-(1,1,4-trioxo-1,2,5-thiadiazolidin-2-yl)-naphthalen-2-yl ester;
2,2-Dimethylpropionic acid 6-(3-cyano-3-methylpropyl)-3-(1,1,4-trioxo-1,2,5-thiadiazolidin-2-yl)-naphthalen-2-yl ester;
Propionic acid 6-(3-cyano-3-methylpropyl)-3-(1,1,4-trioxo-1,2,5-thiadiazolidin-2-yl)-naphthalen-2-yl ester;
2-Ethylbutyric acid 6-(3-cyano-3-methylpropyl)-3-(1,1,4-trioxo-1,2,5-thiadiazolidin-2-yl)-naphthalen-2-yl ester;
Hexanoic acid 6-(3-cyano-3-methylpropyl)-3-(1,1,4-trioxo-1,2,5-thiadiazolidin-2-yl)-naphthalen-2-yl ester;
2-Acetoxy-benzoic acid 6-(3-cyano-3-methylpropyl)-3-(1,1,4-trioxo-1,2,5-thiadiazolidin-2-yl)-naphthalen-2-yl ester;
Pentanoic acid 6-(3-cyano-3-methylpropyl)-3-(1,1,4-trioxo-1,2,5-thiadiazolidin-2-yl)-naphthalen-2-yl ester;
Acetic acid 6-(3-cyano-3-methylpropyl)-3-(1,1,4-trioxo-1,2,5-thiadiazolidin-2-yl)-naphthalen-2-yl ester;
3-Methylbenzoic acid 6-(3-cyano-3-methylpropyl)-3-(1,1,4-trioxo-1,2,5-thiadiazolidin-2-yl)-naphthalen-2-yl ester;
2-Methylbenzoic acid 6-(3-cyano-3-methylpropyl)-3-(1,1,4-trioxo-1,2,5-thiadiazolidin-2-yl)-naphthalen-2-yl ester;
4-Butylbenzoic acid 6-(3-cyano-3-methylpropyl)-3-(1,1,4-trioxo-1,2,5-thiadiazolidin-2-yl)-naphthalen-2-yl ester;
Cyclohexanecarboxylic acid 6-(3-cyano-3-methylpropyl)-3-(1,1,4-trioxo-1,2,5-thiadiazolidin-2-yl)-naphthalen-2-yl ester;
4-tert-Butylbenzoic acid 6-(3-cyano-3-methylpropyl)-3-(1,1,4-trioxo-1,2,5-thiadiazolidin-2-yl)-naphthalen-2-yl ester;
2,2-Dimethylpropionic acid 6-(3-cyanophenyl)-3-(1,1,4-trioxo-1,2,5-thiadiazolidin-2-yl)-naphthalen-2-yl ester;
Benzoic acid 6-(4-ethoxycarbonylbutyl)-3-(1,1,4-trioxo-1,2,5-thiadiazolidin-2-yl)-naphthalen-2-yl ester;
Benzoic acid 6-(3-methylbutyl)-3-(1,1,4-trioxo-1,2,5-thiadiazolidin-2-yl)-naphthalen-2-yl ester;
Benzoic acid 6-((E)-4-hydroxy-4-methylpent-1-enyl)-3-(1,1,4-trioxo-1,2,5-thiadiazolidin-2-yl)-naphthalen-2-yl ester;
Benzoic acid 6-methyl-3-(1,1,4-trioxo-1,2,5-thiadiazolidin-2-yl)-naphthalen-2-yl ester;
Benzoic acid 6-(5-hydroxy-4,4-dimethylpentyl)-3-(1,1,4-trioxo-1,2,5-thiadiazolidin-2-yl)-naphthalen-2-yl ester;
5-[3-Hydroxy-7-(5-hydroxy-4,4-dimethylpentyl)-naphthalen-2-yl]-1,1-dioxo-1,2,5-thiadiazolidin-3-one;
5-(3-Hydroxy-5,6,7,8-tetrahydronapthalen-2-yl)-1,1-dioxo-1,2,5-thiadiazolidin-3-one;
5-(3,6-Dihydroxy-5,6,7,8-tetrahydronaphthalen-2-yl)-1,1-dioxo-1,2,5-thiadiazolidin-3-one;
5-(3-Hydroxy-6-methoxy-5,6,7,8-tetrahydronaphthalen-2-yl)-1,1-dioxo-1,2,5-thiadiazolidin-3-one;
5-(6-Ethoxy-3-hydroxy-5,6,7,8-tetrahydronaphthalen-2-yl)-1,1-dioxo-1,2,5-thiadiazolidin-3-one;
5-(3-Hydroxy-7-methyl-5,6,7,8-tetrahydronaphthalen-2-yl)-1,1-dioxo-1,2,5-thiadiazolidin-3-one;
5-(3-Hydroxy-7,7-dimethyl-5,6,7,8-tetrahydronaphthalen-2-yl)-1,1-dioxo-1,2,5-thiadiazolidin-3-one;
5-(3-Hydroxy-7-trifluoromethyl-5,6,7,8-tetrahydronaphthalen-2-yl)-1,1-dioxo-1,2,5-thiadiazolidin-3-one;
5-(3-Hydroxy-7-isopropyl-5,6,7,8-tetrahydronaphthalen-2-yl)-1,1-dioxo-1,2,5-thiadiazolidin-3-one;
5-(7-Ethyl-3-hydroxy-5,6,7,8-tetrahydronaphthalen-2-yl)-1,1-dioxo-1,2,5-thiadiazolidin-3-one;
5-(7,7-Diethyl-3-hydroxy-5,6,7,8-tetrahydronaphthalen-2-yl)-1,1-dioxo-1,2,5-thiadiazolidin-3-one;

5-(3-Hydroxy-7,7-dipropyl-5,6,7,8-tetrahydronaphthalen-2-yl)-1,1-dioxo-1,2,5-thiadiazolidin-3-one;
5-(6'-Hydroxy-3',4'-dihydro-1'H-spiro[cyclopentane-1,2'-naphthalen]-7'-yl)1,2,5-thiadiazolidin-3-one 1,1-dioxide;
5-((S)-7-Ethyl-3-hydroxy-5,6,7,8-tetrahydronaphthalen-2-yl)-1,1-dioxo-1,2,5-thiadiazolidin-3-one;
5-[6-Hydroxy-7-(1,1,4-trioxo-1,2,5-thiadiazolidin-2-yl)-1,2,3,4-tetrahydronaphthalen-2-yl]-2,2-dimethylpentanoic acid methyl ester;
5-[6-Hydroxy-7-(1,1,4-trioxo-1,2,5-thiadiazolidin-2-yl)-1,2,3,4-tetrahydronaphthalen-2-yl]-2,2-dimethylpentanoic acid;
5-(6-Hydroxy-2-methyl-2,3-dihydrobenzo[b]thiophen-5-yl)-1,1-dioxo-1,2,5-thiadiazolidin-3-one;
5-(6-Hydroxyindan-5-yl)-1,1-dioxo-1,2,5-thiadiazolidin-3-one;
5-(6-Hydroxy-2,2-dimethylindan-5-yl)-1,1-dioxo-1,2,5-thiadiazolidin-3-one;
5-(6-Hydroxy-2-methylindan-5-yl)-1,1-dioxo-1,2,5-thiadiazolidin-3-one;
Benzoic acid 6,6-dimethyl-3-(1,1,4-trioxo-1,2,5-thiadiazolidin-2-yl)-5,6,7,8-tetrahydronaphthalen-2-yl ester;
Benzoic acid (S)-6-ethyl-3-(1,1,4-trioxo-1,2,5-thiadiazolidin-2-yl)-5,6,7,8-tetrahydronaphthalen-2-yl ester;
Benzoic acid 6-ethyl-3-(1,1,4-trioxo-1,2,5-thiadiazolidin-2-yl)-5,6,7,8-tetrahydronaphthalen-2-yl ester;
Benzoic acid 6,6-diethyl-3-(1,1,4-trioxo-1,2,5-thiadiazolidin-2-yl)-5,6,7,8-tetrahydronaphthalen-2-yl ester;
Benzoic acid 2,2-dimethyl-6-(1,1,4-trioxo-1,2,5-thiadiazolidin-2-yl)-indan-5-yl ester;
5-(3-Allyloxy-6-hydroxybenzo[d]isoxazol-5-yl)-1,1-dioxo-1,2,5-thiadiazolidin-3-one;
5-Hydroxy-6-(1,1,4-trioxo-1,2,5-thiadiazolidin-2-yl)-1H-indole-2-carboxylic acid ethyl ester potassium salt;
5-Hydroxy-6-(1,1,4-trioxo-1,2,5-thiadiazolidin-2-yl)-1H-indole-2-carboxylic acid 3-methyl-butyl ester;
5-Hydroxy-6-(1,1,4-trioxo-1,2,5-thiadiazolidin-2-yl)-1H-indole-2-carboxylic acid isobutyl ester;
5-Hydroxy-6-(1,1,4-trioxo-1,2,5-thiadiazolidin-2-yl)-1H-indole-2-carboxylic acid; and
5-(7-Hydroxy-3-methoxy-2-oxo-2H-chromen-6-yl)-1,1-dioxo-1,2,5-thiadiazolidin-3-one;
5-[3-Hydroxy-7-((E)-propenyl)-naphthalen-2-yl]-1,1-dioxo-[1,2,5]thiadiazolidin-3-one;
5-(3-Hydroxy-7-vinyl-naphthalen-2-yl)-1,1-dioxo-[1,2,5]thiadiazolidin-3-one;
4-[6-Hydroxy-7-(1,1,4-trioxo-[1,2,5]thiadiazolidin-2-yl)-naphthalen-2-yl]-butyric acid methyl ester;
5-{3-Hydroxy-7-[3-(2,2,2-trifluoro-ethoxy)-propyl]-naphthalen-2-yl}-1,1-dioxo-[1,2,5]thiadiazolidin-3-one;
4-[6-Hydroxy-7-(1,1,4-trioxo-[1,2,5]thiadiazolidin-2-yl)-naphthalen-2-yl]-butyric acid;
5-[3-Hydroxy-7-(3-phenyl-propyl)-naphthalen-2-yl]-1,1-dioxo-[1,2,5]thiadiazolidin-3-one;
3-{3-[6-Hydroxy-7-(1,1,4-trioxo-thiadiazolidin-2-yl)-naphthalen-2-yl]-phenyl}-propionic acid;
or a pharmaceutically acceptable salt thereof.

29. A method for the inhibition of PTPase activity, comprising:
a administering to a mammal in need thereof a therapeutically effective amount of a compound of claim 1, or a pharmaceutically acceptable salt thereof.

30. A method for reducing glucose levels in mammals, comprising:
administering to a mammal in need thereof a therapeutically effective amount of a compound of claim 1, or a pharmaceutically acceptable salt thereof.

31. A method for the treatment of insulin resistance, glucose intolerance, type 2 diabetes, diabetic renal insufficiency diabetic nephropathy, diabetic retinopathy, or obesity comprising:
administering to a mammal in need thereof a therapeutically effective amount of a compound of claim 1, or a pharmaceutically acceptable salt thereof.

32. A pharmaceutical composition, comprising:
a therapeutically effective amount of a compound according to claim 1, or a pharmaceutically acceptable salt thereof, in combination with one or more pharmaceutically acceptable carriers.

33. A pharmaceutical composition, comprising:
a jointly therapeutically effective amount of a compound according to claim 1, or a pharmaceutically acceptable salt thereof, in combination with an anti-diabetic agents, a hypolipidemic agent, an anti-obesity agent or an anti-hypertensive agent.

* * * * *